(12) United States Patent
Fonge et al.

(10) Patent No.: US 12,151,004 B2
(45) Date of Patent: Nov. 26, 2024

(54) METHODS AND COMPOSITIONS FOR TARGETING DISEASE RELATED CELL SURFACE RECEPTORS USING RADIOLABELED AND/OR CYTOTOXIN LABELLED ANTIBODIES

(71) Applicant: University of Saskatchewan, Saskatoon (CA)

(72) Inventors: Humphrey Fonge, Saskatoon (CA); Clarence Ronald Geyer, Saskatoon (CA); Siddesh Vrushabendra swamy Hartimath, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 392 days.

(21) Appl. No.: 17/163,145

(22) Filed: Jan. 29, 2021

(65) Prior Publication Data
US 2021/0236667 A1 Aug. 5, 2021

Related U.S. Application Data

(60) Provisional application No. 62/968,701, filed on Jan. 31, 2020.

(51) Int. Cl.
| | | |
|---|---|---|
| *A61K 51/10* | (2006.01) | |
| *A61K 39/00* | (2006.01) | |
| *A61K 47/60* | (2017.01) | |
| *A61K 47/64* | (2017.01) | |
| *A61K 47/68* | (2017.01) | |
| *A61P 35/00* | (2006.01) | |
| *C07K 16/28* | (2006.01) | |
| *C07K 16/32* | (2006.01) | |

(52) U.S. Cl.
CPC ............ *A61K 51/109* (2013.01); *A61K 47/60* (2017.08); *A61K 47/6415* (2017.08); *A61K 47/6849* (2017.08); *A61K 47/6851* (2017.08); *A61K 51/103* (2013.01); *A61K 51/1045* (2013.01); *A61P 35/00* (2018.01); *C07K 16/2863* (2013.01); *C07K 16/32* (2013.01); *A61K 2039/505* (2013.01); *C07K 2317/31* (2013.01); *C07K 2317/622* (2013.01); *C07K 2317/92* (2013.01)

(58) Field of Classification Search
CPC .. A61K 51/109; A61K 47/60; A61K 47/6415; A61K 47/6849; A61K 47/6851; A61K 51/1045; A61K 2039/505; C07K 16/2863; C07K 16/32; C07K 2317/31; C07K 2317/622; C07K 2317/92
See application file for complete search history.

(56) References Cited

U.S. PATENT DOCUMENTS

2011/0200595 A1* 8/2011 Gerdes .............. C07K 16/2863
424/133.1

FOREIGN PATENT DOCUMENTS

WO WO2016201051 * 12/2016 ........... A61K 39/395

OTHER PUBLICATIONS

Edwards et al., The Remarkable Flexibility of the Human Antibody Repertoire; Isolation of Over One Thousand Different Antibodies to a Single Protein, BLyS. J Mol Biol. Nov. 14, 2003;334(1): 103-18. (Year: 2003).*
Lloyd et al. Modelling the human immune response: performance of a 1011 human antibody repertoire against a broad panel of therapeutically relevant antigens. Protein Eng. Des. Sel., Mar;22(3): 159-68, 2009. (Year: 2009).*
Goel et al., Plasticity within the Antigen-Combining Site May Manifest as Molecular Mimicry in the Humoral Immune Response. J. Immunol.173(12):7358-67, 2004. (Year: 2004).*
Kanyavuz et al., Breaking the law: unconventional strategies for antibody diversification. Nat Rev Immunol. 19(6):355-368, 2019. (Year: 2019).*
Tsai et al., Aligning physics and physiology: Engineering antibodies for radionuclide delivery. J. Labelled Comp. Radiopharm. 61, 693-714, 2018. (Year: 2018).*
Khongorzul et al. Antibody-Drug Conjugates: A Comprehensive Review. Mol. Cancer Res. 18(1), 3-19, 2020. (Year: 2020).*
Ferraro et al., Inhibition of triple-negative breast cancer models by combinations of antibodies to EGFR. Proc. Natl. Acad. Sci. 110, 1815-1820, 2013. (Year: 2013).*
Cai et al., Differential binding patterns of monoclonal antibody 2C4 to the ErbB3-p185her2/neu and the EGFR-p185her2/neu complexes. Oncogene, 27, 3870-3874, 2008. (Year: 2008).*
Keir et al., Sym004-induced EGFR elimination is associated with profound antitumor activity in EGFRvIII patient-derived glioblastoma models. J. Neuro-oncology, 138, 489-498, 2018. (Year: 2018).*
Capelan et al. Pertuzumab: new hope for patients with HER2-positive breast cancer Annals of Oncology, 24,273-282, 2013. (Year: 2013).*
Carey, L.A., et al., "Race, breast cancer subtypes, and survival in the Carolina Breast Cancer Study," JAMA. 2006, vol. 295, No. 21, pp. 2492-2502.
Changavi, A.A., et al., "Epidermal Growth Factor Receptor Expression in Triple Negative and Nontriple Negative Breast Carcinomas", J Lab Physicians, 2015, vol. 7, issue 2, pp. 79-83.

(Continued)

*Primary Examiner* — Elly-Gerald Stoica
(74) *Attorney, Agent, or Firm* — SMART & BIGGAR LP Ainslie Parsons

(57) ABSTRACT

The disclosure provides radiolabeled and/or cytotoxin labelled antibodies and methods and uses of these antibodies. In one embodiment, provided is a cytotoxic agent comprising an antibody that specifically binds a target disease cell surface receptor, a cytotoxin, and a radiolabel, wherein the cytotoxin is linked directly or indirectly to the antibody, and wherein the radiolabel comprises a radionuclide and optionally a scaffold, wherein the scaffold is directly or indirectly coupled to the antibody. Also provided are methods of preparing the cytotoxic agent and methods of treating disease using the cytotoxic agent.

4 Claims, 44 Drawing Sheets

Specification includes a Sequence Listing.

(56) References Cited

OTHER PUBLICATIONS

Corkery, B., et al., "Epidermal growth factor receptor as a potential therapeutic target in triple-negative breast cancer", Annals of Oncol. 2009, vol. 20, No. 5, pp. 862-867.
Tanei, T., et al., "Antitumor activity of Cetuximab in combination with Ixabepilone on triple negative breast cancer stem cells", Breast Cancer Res. 2016;18(1), pp. 1-9.
Baselga, J. et al., "Randomized Phase II Study of the Anti-Epidermal Growth Factor Receptor Monoclonal Antibody Cetuximab With Cisplatin Versus Cisplatin Alone in Patients With Metastatic Triple-Negative Breast Cancer", Journal of Clinical Oncology, 2013, vol. 31, issue 20, pp. 2586-2592.
Wykosky, J., et al., "The EphA2 receptor and ephrinA1 ligand in solid tumors: function and therapeutic targeting", Mol Cancer Res. 2008;6(12), pp. 1795-1806.
Song, W., et al., "Targeting EphA2 impairs cell cycle progression and growth of basal-like/triple-negative breast cancers", Oncogene, 2017, vol. 36(40), pp. 5620-5630.
Sharkey, R.M., et al. "Combination radioimmunotherapy and chemoimmunotherapy involving different or the same targets improves therapy of human pancreatic carcinoma xenograft models", Mol Cancer Ther, 2011, 10(6), pp. 1072-1081.
Crozier, J.A., et al., "N0436 (Alliance): A Phase II Trial of Irinotecan With Cetuximab in Patients With Metastatic Breast Cancer Previously Exposed to Anthracycline and/or Taxane-Containing Therapy", Clinical Breast Cancer, 2016, vol. 16, issue 1, pp. 23-30, doi: 10.1016/j.clbc.2015.08.002.
Baselga, J., et al., "Randomized phase II study of the anti-epidermal growth factor receptor monoclonal antibody cetuximab with cisplatin versus cisplatin alone in patients with metastatic triple-negative breast cancer", J Clin Oncol. 2013, vol. 31,No. 20, pp. 2586-2592.
Parker, C., et al., "Alpha emitter radium-223 and survival in metastatic prostate cancer", N Engl J Med. 2013, vol. 369, No. 3, pp. 213-223.
Kratochwil, C. et al., "225Ac-PSMA-617 for PSMA-Targeted alpha-Radiation Therapy of Metastatic Castration-Resistant Prostate Cancer", J Nucl Med. 2016, vol. 57, No. 12, pp. 1941-1944.
Meredith, R., et al., "Dose escalation and dosimetry of first-in-human alpha radioimmunotherapy with 212Pb-TCMC-trastuzumab", J Nucl Med. 2014, vol. 55, No. 10, pp. 1636-1642.
Robinson D.R. et al., "The protein tyrosine kinase family of the human genome", Oncogene 2000, 19(49):5548-5557.
Chung C.H. et al., "Increased epidermal growth factor receptor gene copy number is associated with poor prognosis in head and neck squamous cell carcinomas", Journal of clinical oncology : official journal of the American Society of Clinical Oncology 2006, 24(25):4170-4176.
Alshenawy, H. A., "Immunohistochemical expression of epidermal growth factor receptor, E-cadherin, and matrix metalloproteinase-9 in ovarian epithelial cancer and relation to patient deaths", Annals of diagnostic pathology 2010, 14(6):387-395.
Cunningham D., et al., "Cetuximab monotherapy and cetuximab plus irinotecan in irinotecan-refractory metastatic colorectal cancer", The New England journal of medicine 2004, 351(4):337-345.
Giltnane, J.M., et al., "Quantitative measurement of epidermal growth factor receptor is a negative predictive factor for tamoxifen response in hormone receptor positive premenopausal breast cancer", Journal of clinical oncology : official journal of the American Society of Clinical Oncology 2007, 25(21):3007-3014.
Bellone S., et al., "Overexpression of epidermal growth factor type-1 receptor (EGF-R1) in cervical cancer: implications for Cetuximab-mediated therapy in recurrent/metastatic disease", Gynecologic oncology 2007, 106(3):513-520.
Siwak, D.R., et al., "Targeting the epidermal growth factor receptor in epithelial ovarian cancer: current knowledge and future challenges", Journal of oncology 2010, 2010:568938, pp. 1-20.
Bonner, J.A., et al., "Radiotherapy plus cetuximab for squamous-cell carcinoma of the head and neck", The New England journal of medicine 2006, 354(6), pp. 567-578.
Addeo, R., et al., "Panitumumab: a new frontier of target therapy for the treatment of metastatic colorectal cancer", Expert review of anticancer therapy 2010, 10(4):499-505.
Ramos, T.C., et al., "Treatment of high-grade glioma patients with the humanized anti-epidermal growth factor receptor (EGFR) antibody h-R3: report from a phase I/II trial", Cancer biology & therapy 2006, 5(4), pp. 375-379.
Crombet, T., et al., "Use of the humanized anti-epidermal growth factor receptor monoclonal antibody h-R3 in combination with radiotherapy in the treatment of locally advanced head and neck cancer patients", Journal of clinical oncology : official journal of the American Society of Clinical Oncology 2004, 22(9), pp. 1646-1654.
Patel, D., et al., "Monoclonal antibody cetuximab binds to and down-regulates constitutively activated epidermal growth factor receptor vIII on the cell surface", Anticancer research 2007, 27(5a), pp. 3355-3366.
Sickmier, E.A., et al., "The Panitumumab EGFR Complex Reveals a Binding Mechanism That Overcomes Cetuximab Induced Resistance", PloS one 2016, 11(9):e0163366, pp. 1-11.
Keating, G.M., "Panitumumab: a review of its use in metastatic colorectal cancer", Drugs 2010, 70(8), pp. 1059-1078.
Molinari, E. et.al., "Cetuximab-induced acne", Dermatology (Basel, Switzerland) 2005, 211(4), pp. 330-333.
Lacouture, M. E., et al. "Mechanisms of cutaneous toxicities to EGFR inhibitors", Nature reviews Cancer 2006, 6(10), pp. 803-812.
Rojo, F., et al.,"Pharmacodynamic trial of nimotuzumab in unresectable squamous cell carcinoma of the head and neck: a Sendo Foundation study", Clinical cancer research : an official journal of the American Association for Cancer Research 2010, 16(8), pp. 2474-2482.
Miersch, S., et al., "Structure-Directed and Tailored Diversity Synthetic Antibody Libraries Yield Novel Anti-EGFR Antagonists", ACS chemical biology 2017, 12(5), pp. 1381-1389.
Bernhard, W., et al., "Near infrared imaging of epidermal growth factor receptor positive xenografts in mice with domain I/II specific antibody fragments", Theranostics 2019, 9(4), pp. 974-985.
Nakai, K., et al., "A perspective on anti-EGFR therapies targeting triple-negative breast cancer", American journal of cancer research 2016, 6(8), pp. 1609-1623.
Hamblett, K.J., et al., "AMG 595, an Anti-EGFRvIII Antibody-Drug Conjugate, Induces Potent Antitumor Activity against EGFRvIII-Expressing Glioblastoma", Molecular cancer therapeutics 2015, 14(7), pp. 1614-1624.
LoRusso, P.M., et al., "Trastuzumab emtansine: a unique antibody-drug conjugate in development for human epidermal growth factor receptor 2-positive cancer", Clinical cancer research : an official journal of the American Association for Cancer Research 2011, 17(20), pp. 6437-6447.
Verma, S., et al., "Trastuzumab emtansine for HER2-positive advanced breast cancer", N Engl J Med 2012, 367(19), pp. 1783-1791.
Holland, J.P., et al., "Standardized methods for the production of high specific-activity zirconium-89", Nuclear medicine and biology 2009, 36(7), pp. 729-739.
Sharma, P., et al., "Primary, Adaptive, and Acquired Resistance to Cancer Immunotherapy", Cell 2017, 168(4), pp. 707-723.
Babina, I.S., et al., "Advances and challenges in targeting FGFR signalling in cancer", Nature reviews Cancer 2017, 17(5), pp. 318-332.
Ritter, C.A., et al., "Human breast cancer cells selected for resistance to trastuzumab in vivo overexpress epidermal growth factor receptor and ErbB ligands and remain dependent on the ErbB receptor network", Clinical cancer research : an official journal of the American Association for Cancer Research 2007, 13(16), pp. 4909-4919.
Barok, M., et al., "Trastuzumab emtansine: mechanisms of action and drug resistance", Breast cancer research : BCR 2014, 16(2): 209, pp. 1-12.
Shefet-Carasso, L., et al., "Antibody-targeted drugs and drug resistance—challenges and solutions", Drug resistance updates : reviews and commentaries in antimicrobial and anticancer chemotherapy 2015, 18:36-46.

(56) References Cited

OTHER PUBLICATIONS

Kovtun, Y.V., et al.,"Antibody-maytansinoid conjugates designed to bypass multidrug resistance", Cancer research 2010, 70(6), pp. 2528-2537.

Zhao, R.Y., et al., "Synthesis and evaluation of hydrophilic linkers for antibody-maytansinoid conjugates.", Journal of medicinal chemistry 2011, 54(10), pp. 3606-3623.

Hartimath, S.V. et al., "Therapeutic potential of nimotuzumab PEGylated-maytansine antibody drug conjugates against EGFR positive xenograft." Oncotarget, Feb. 1, 2019, vol. 10, No. 10, pp. 1031-1044. doi:10.18632/oncotarget.26613.

Thiele, N.A. et al., "An Eighteen-Membered Macrocyclic Ligand for Actinium-225 Targeted Alpha Therapy", Angew. Chem. Int. Ed., 2017, 56, pp. 14712-14717.

Erickson, H.K., et al., "Antibody-maytansinoid conjugates are activated in targeted cancer cells by lysosomal degradation and linker-dependent intracellular processing", Cancer research 2006, 66(8), pp. 4426-4433.

Hartimath, S.V., et al., "Preclinical Evaluation of (111)In-labeled PEGylated Maytansine Nimotuzumab Drug Conjugates in EGFR-positive Cancer Models", J Nucl Med 2019, vol. 60, pp. 1103-1110, doi: 10.2967/jnumed.118.220095.

Mazorra, Z. et al., "Nimotuzumab Induces NK Cell Activation, Cytotoxicity, Dendritic Cell Maturation and Expansion of EGFR-Specific T Cells in Head and Neck Cancer Patients", Front Pharmacol 2017, vol. 8, article 382, pp. 1-13.

Queern, S.L., et al., "Production of Zr-89 using sputtered yttrium coin targets (89)Zr using sputtered yttrium coin targets", Nuclear medicine and biology 2017, 50, pp. 11-16.

Chekol, R., et al., "(89)Zr-nimotuzumab for immunoPET imaging of epidermal growth factor receptor I", Oncotarget 2018, 9(24), pp. 17117-17132.

Lindmo, T., et al., "Determination of the true immunoreactive fraction of monoclonal antibodies after radiolabeling", Methods in enzymology 1986, 121, pp. 678-691.

Fasih, A. et al., "(1)(1)(1)In-Bn-DTPA-nimotuzumab with/without modification with nuclear translocation sequence (NLS) peptides: an Auger electron-emitting radioimmunotherapeutic agent for EGFR-positive and trastuzumab (Herceptin)-resistant breast cancer", Breast Cancer Res Treat 2012, 135(1), pp. 189-200.

Li J.Y., et al.,"A Biparatopic HER2-Targeting Antibody-Drug Conjugate Induces Tumor Regression in Primary Models Refractory to or Ineligible for HER2-Targeted Therapy", Cancer Cell 2016, vol. 29(1), pp. 117-129.

Oganesyan, V. et al., "Structural insights into the mechanism of action of a biparatopic anti-HER2 antibody", J Biol Chem 2018, 293(22), pp. 8439-8448.

Bradley, M. E. et al., "Potent and efficacious inhibition of CXCR2 signaling by biparatopic nanobodies combining two distinct modes of action", Mol Pharmacol 2015, 87(2), pp. 251-262.

Thiele N.A. et al., "Actinium-225 for Targeted α Therapy: Coordination Chemistry and Current Chelation Approaches", Cancer Biother Radiopharm. 2018;33(8):336-348. doi:10.1089/cbr.2018.2494.

\* cited by examiner

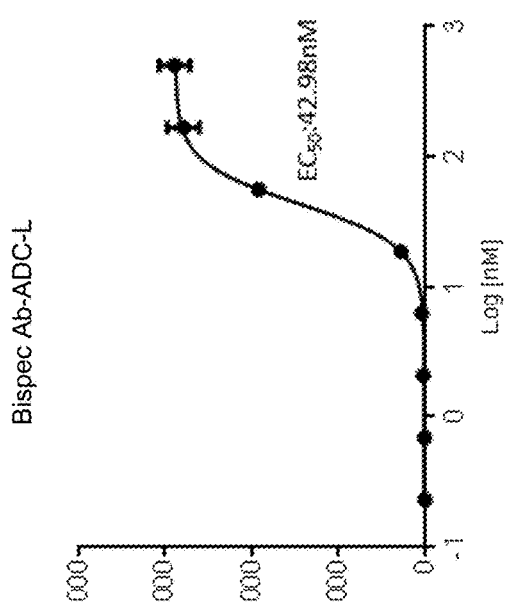
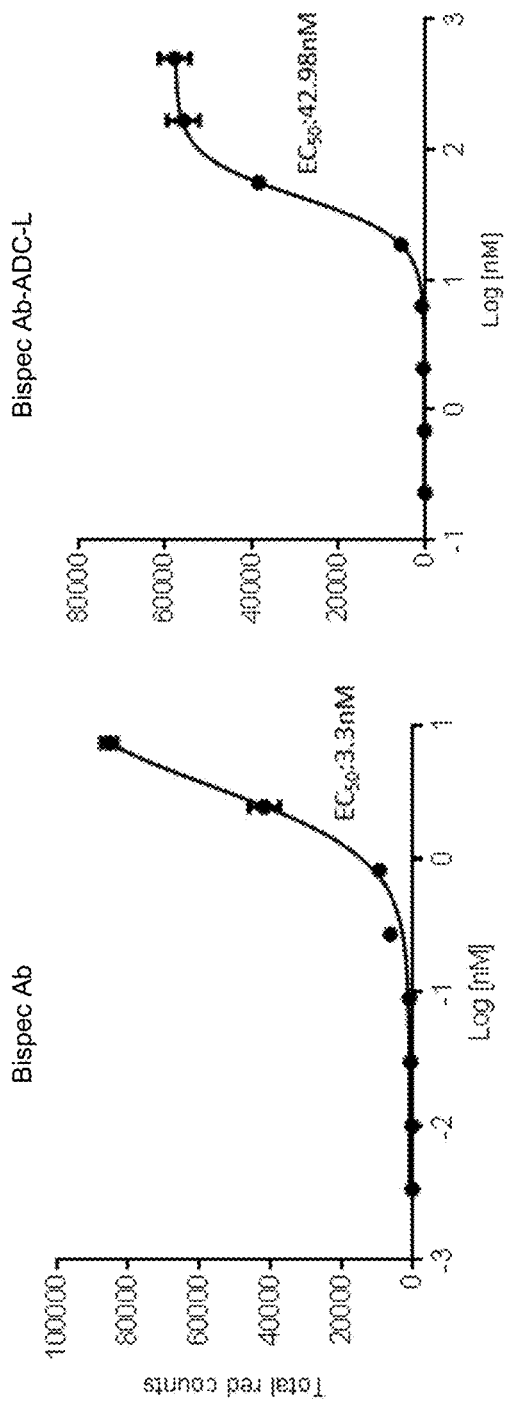
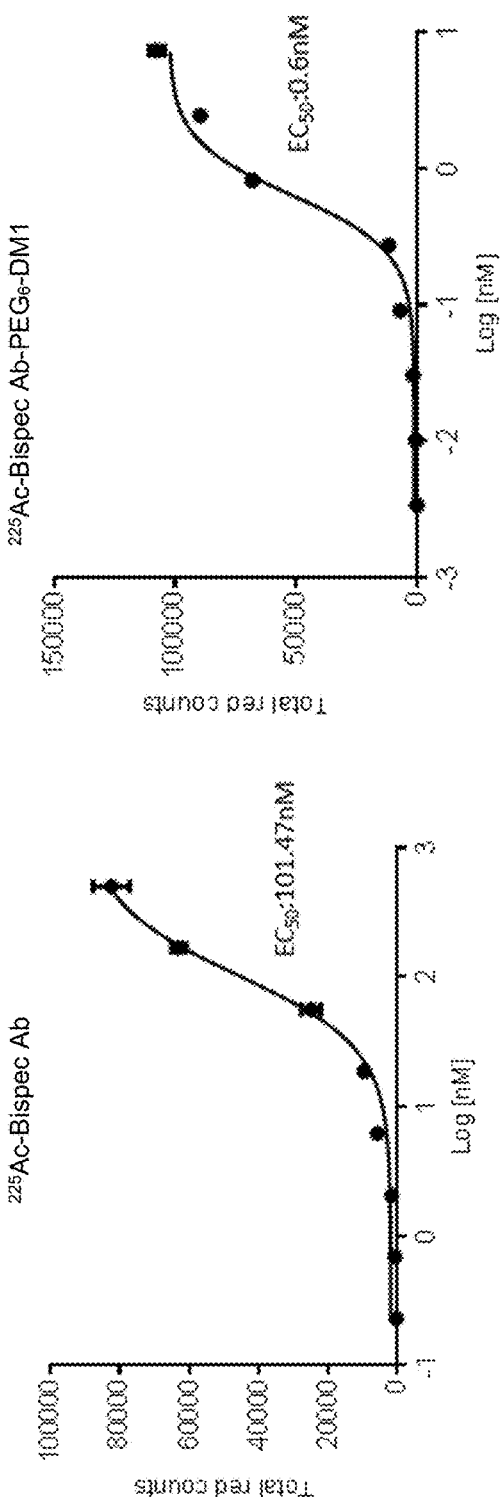

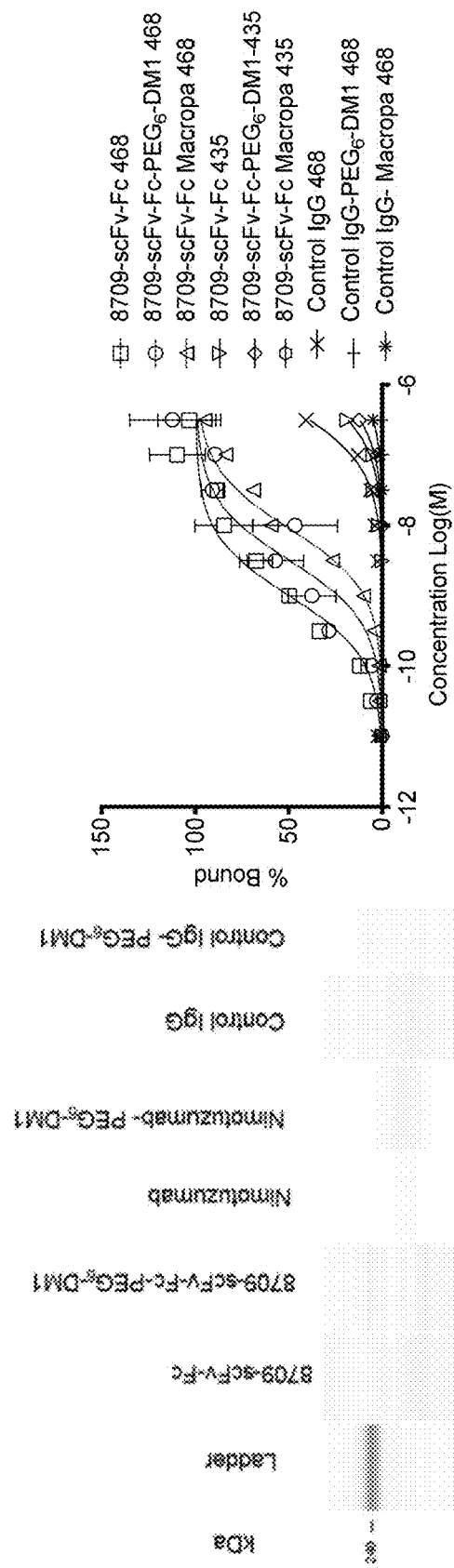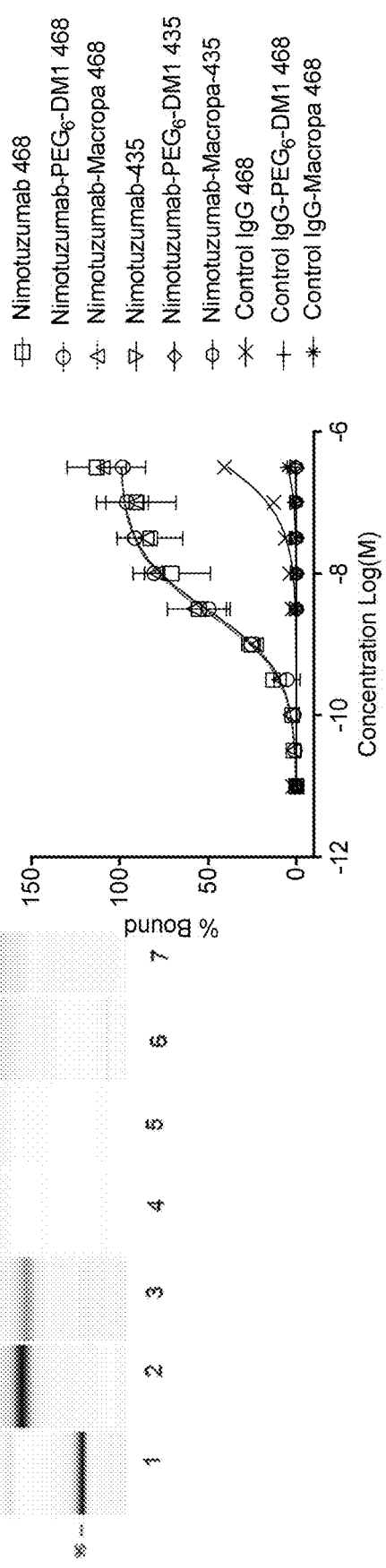
Fig. 16A
Fig. 16B
Fig. 16C

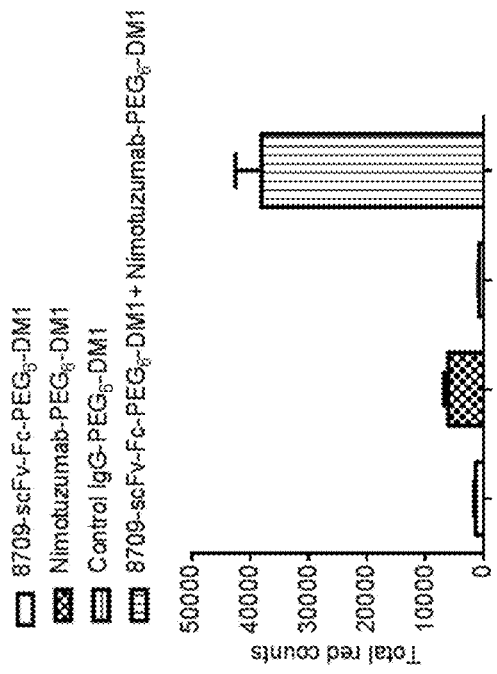
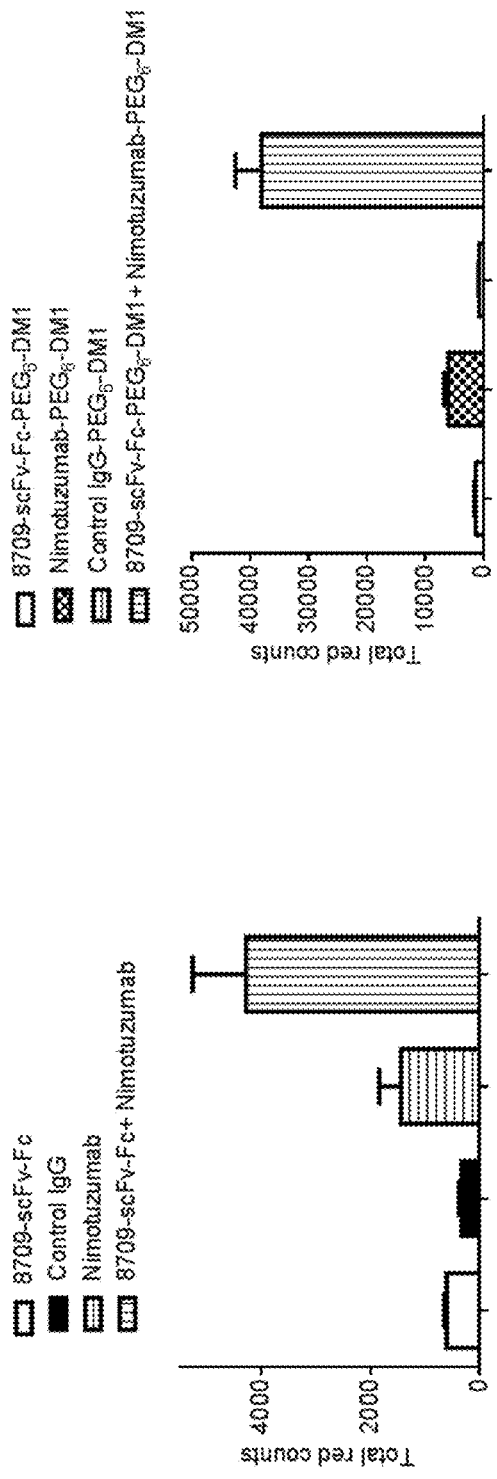
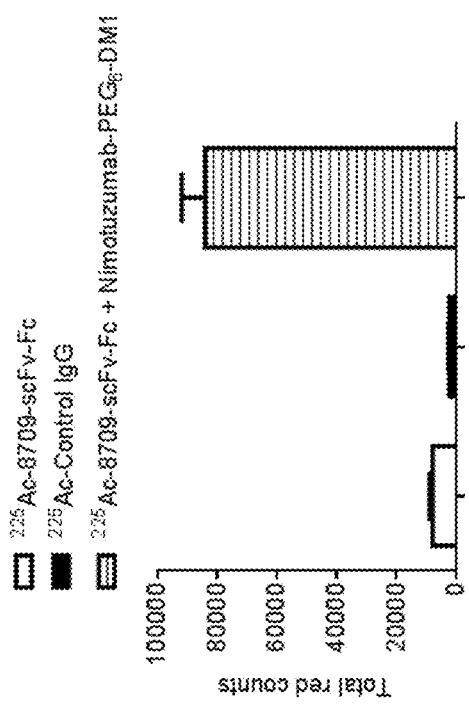

Fig. 23
Nimotuzumab radiolabeled using DOTA (commercial chelator) as chelator for $^{225}$Ac
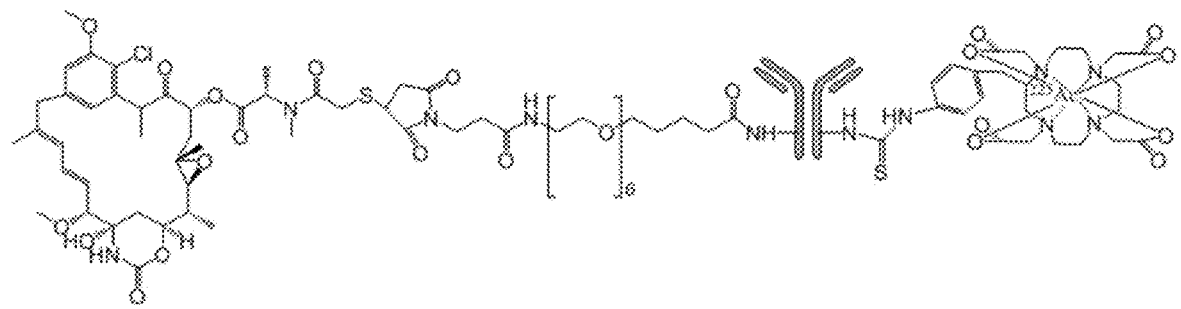
$^{225}$Ac-nimotuzumab-PEG$_6$-DM1
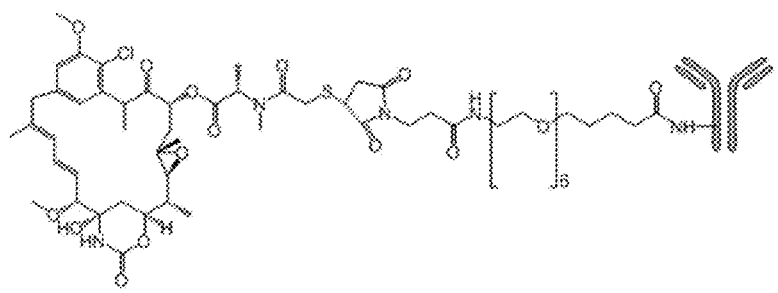
nimotuzumab-PEG$_6$-DM1
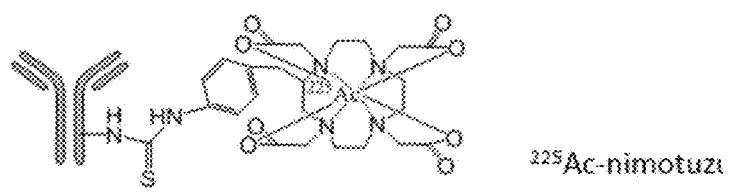
$^{225}$Ac-nimotuzu

METHODS AND COMPOSITIONS FOR TARGETING DISEASE RELATED CELL SURFACE RECEPTORS USING RADIOLABELED AND/OR CYTOTOXIN LABELLED ANTIBODIES

RELATED APPLICATIONS

The present application claims the benefit of priority to U.S. Provisional Patent Application Ser. No. 62/968,701 filed Jan. 31, 2020, the entire contents of which are hereby incorporated by reference.

INCORPORATION OF SEQUENCE LISTING

A computer readable form of the Sequence Listing "13764-P60861US01_SequenceListing.txt" (8,192 bytes), submitted via EFS-WEB and created on Jan. 27, 2021, is herein incorporated by reference.

FIELD

This disclosure relates generally to radiolabeled and/or cytotoxin labelled antibodies for targeting cell surface receptors, and to methods and uses of these antibodies.

BACKGROUND

The presence and/or overexpression of receptors on the cell surface is a hallmark of many disease associated cells including cancer cells. As such, cell surface receptors are an attractive antibody target. However, many antibodies to cell surface receptors have shown low efficacy and patients frequently develop resistance.

New agents and methods for targeting cell surface receptors and delivering cytotoxins to target cells are desired.

SUMMARY

The disclosure provides a cytotoxic agent comprising an antibody that specifically binds a target cell surface receptor, a cytotoxin, and a radiolabel, wherein the cytotoxin is linked directly or indirectly to the antibody and wherein the radiolabel comprises a radionuclide and optionally a scaffold, wherein the scaffold is directly or indirectly coupled to the antibody.

As shown herein, antibody immunoconjugates and combinations of immunoconjugates comprising either an antibody comprising a combination of cytotoxicities—cytotoxin and radionuclide—in one cytotoxic agent or separately in two cytotoxic agents targeting different domains of a target receptor as a combination therapy, exhibited increased internalization and synergistic therapeutic effect. In addition, it was found that preparing the radiolabeled conjugates using a method where the cytotoxin is conjugated to the antibody prior to addition of the radiolabel produced better cytotoxic agents compared to a cytotoxic agent prepared using a method where the radiolabel is added prior to conjugation of the cytotoxin to the antibody. For example, as shown in Example 2, addition of $^{225}$Ac ($^{225}$Ac-cixutumumab-PEG6-DM1) to the antibody drug conjugate had >6000 fold increase in the cytotoxicity in the tested cell lines. Further as shown in Example 3, the combination of an EGFR domain I/II antibody-PEG$_6$-DM1 conjugate and an EGFR domain III antibody-PEG$_6$-DM1 conjugate enhanced the cytotoxicity compared with single agents and demonstrated a significant synergistic advantage of the combination. This cytotoxicity is several fold enhanced when these constructs carry multiple payloads such as a cytotoxic drug and a therapeutic isotope.

Accordingly, one aspect of the present disclosure provides cytotoxic agent comprising an antibody that specifically binds a target disease cell surface receptor, a cytotoxin, and a radiolabel, wherein the cytotoxin is linked directly or indirectly to the antibody, and wherein the radiolabel comprises a radionuclide and optionally a scaffold, wherein the scaffold is directly or indirectly coupled to the antibody. The cytotoxic agent can further comprise a linker linking the antibody and the cytotoxin.

In one embodiment, the radionuclide is an alpha emitter and the specific activity of the cytotoxic agent is at least 3, 4, 5 or 6 kBq/microgram of the antibody. In another embodiment, the radionuclide is a beta or gamma emitter and the specific activity of the cytotoxic agent is at least 0.2, 0.4, 0.6, 0.8 or 1.0 kBq/microgram of the antibody.

In another embodiment, the cytotoxic agent has a radionuclide loss of less than 50, 40, 30, 25, 20, 15, 10, 5 or 1% in 7 days. In another embodiment, the cytotoxic agent has a radionuclide loss of less than 50, 40, 30, 25, 20, 15, 10, 5 or 1% in 48 hours. In one embodiment, the scaffold is derived from a bifunctional chelator and is attached to the antibody by an isopeptide linkage with an amino group of the antibody.

In another embodiment, the antibody is an IgG molecule and/or a monoclonal antibody. In another embodiment, the antibody is selected from the group consisting of a fragment antigen-binding Fab, a single-chain Fv (scFv), a (svFv)2, a scFv-CH3, a scFv-Fc, a diabody, a bispecific antibody, a phage-Fab and a phage-scFv.

In another embodiment, the ratio of cytotoxin to antibody is 2-5:1, optionally 3-4:1.

In another embodiment, the disease is cancer.

In another embodiment, the cell surface receptor is a member of the epidermal growth factor receptor family, optionally EGFR, HER2, HER3 or HER4, or the cell surface receptor is EphA2 or IGF-1R.

In another embodiment, the antibody is a bispecific antibody, optionally an antibody that specifically binds EphA2 and a second disease cell surface receptor. The second disease cell surface receptor can be, for example, a member of the epidermal growth factor receptor family, optionally EGFR, HER2, HER3 or HER4.

In another embodiment, the radionuclide is an alpha-particle emitter or a beta-particle emitter.

In another embodiment, the radionuclide is selected from the group consisting of $^{131}$I, $^{67}$Cu, $^{177}$Lu, $^{213}$Bi, $^{90}$Y, $^{188}$Re, $^{47}$Sc, $^{211}$At, $^{225}$Ac, $^{89}$Zr, $^{227}$Th, $^{212}$Pb, and $^{223}$Ra. In a further Embodiment, the radionuclide is $^{225}$Ac.

In another embodiment, the cytotoxin is a microtubule disruptor.

In another embodiment, the cytotoxin is selected from the group consisting of maytansine and derivatives thereof (maytansinoids), auristatins, calicheamicins, duocarmycins, doxorubicin, anthracyclines, amanitins and camptothecins.

In another embodiment, the cytotoxin is N(2')-deacetyl-N(2')-(3-mercapto-1-oxopropyl)-maytansine (DM1).

Another aspect of the disclosure provides a package or composition comprising the cytotoxic agent as described herein and optionally one or more of a carrier and a second cytotoxic agent, the second cytotoxic agent comprising a second antibody that specifically binds the target cell surface receptor, wherein the second cytotoxic agent comprises a second cytotoxin, wherein the second cytotoxin is linked directly or indirectly to the second antibody or, and/or a second radiolabel, wherein the second radiolabel comprises a second radionuclide and a second scaffold, wherein the second scaffold is directly or indirectly coupled to the second antibody, and optionally wherein the two antibodies each bind different epitopes of the target disease cell surface receptor. In one embodiment, each epitope is on a different extracellular domain of the target disease cell surface receptor.

In one embodiment, in the package the cytotoxic agent is comprised in a first composition and the second cytotoxic agent is comprised in a second composition, each composition provided in separate vials.

In another embodiment, the package or composition comprises the second cytotoxic agent.

In another embodiment, the composition, the first composition and/or the second composition is an intravenous formulation.

Another aspect of the disclosure provides a method of treating a disease comprising administering an effective amount of the cytotoxic agent as described herein or the composition as described herein to a subject in need thereof.

In one embodiment, the disease is cancer, optionally a solid tumour.

In another embodiment, the cell surface receptor is EGFR and the cancer is a cancer of epithelial origin, optionally squamous cell head & neck, glioma, non-small cell lung, colorectal, breast or cervical cancer.

In another embodiment, the cell surface receptor is HER2 and the cancer is a HER2 positive cancer, optionally a breast cancer.

In another embodiment, the cell surface receptor is IGF-1R and the cancer is an IGF-1R positive cancer.

In another embodiment, the cytotoxic agent is administered intravenously.

Another aspect of the disclosure provides a composition comprising:
 (a) a first cytotoxic agent comprising a first antibody that specifically binds a first epitope of a target disease cell surface receptor, and
 (b) a second cytotoxic agent comprising a second antibody that specifically binds a second epitope of the target disease cell surface receptor,
 wherein at least one of the first and second cytotoxic agent comprises a cytotoxin, wherein the cytotoxin is linked directly or indirectly to the antibody,
 wherein at least one of the first and second cytotoxic agent comprises a radiolabel, wherein the radiolabel comprises a radionuclide and a scaffold, wherein the scaffold is directly or indirectly coupled to the antibody,
 and wherein the first epitope is on a first extracellular domain of the target disease cell surface receptor and the second epitope is on a second extracellular domain of the target disease cell surface receptor.

In one embodiment, the cytotoxin is linked directly or indirectly to the antibody by a linker.

In another embodiment, the scaffold is derived from a bifunctional chelator and is attached to the antibody by an isopeptide linkage with an amino group of the antibody.

In another embodiment, the disease is cancer.

In another embodiment, the cell surface receptor is a member of the epidermal growth factor receptor family, optionally EGFR, HER2, HER3 or HER4.

In another embodiment, the cell surface receptor is EGFR and the first antibody specifically binds extracellular domain III of EGFR and the second antibody specifically binds extracellular domain III of EGFR.

In another embodiment, the cell surface receptor is HER2 and the first antibody specifically binds extracellular domain IV of HER2 and the second antibody specifically binds extracellular domain II of HER2, optionally wherein the first antibody is trastuzumab and the second antibody is pertuzumab.

In another embodiment, the radionuclide is an alpha-particle emitter or a beta-particle emitter.

In another embodiment, the radionuclide is selected from the group consisting of $^{131}$I, $^{67}$Cu, $^{177}$Lu, $^{213}$Bi, $^{90}$Y, $^{188}$Re, $^{47}$Sc, $^{211}$AT, $^{225}$Ac, $^{89}$Zr, $^{227}$Th, $^{212}$Pb, and $^{223}$Ra. In another embodiment, the radionuclide is $^{225}$Ac.

In another embodiment, the cytotoxin is a microtubule disruptor, optionally a maytansine or a derivative thereof.

In another embodiment, the cytotoxin is selected from the group consisting of maytansine and derivatives thereof (maytansinoids), auristatins calicheamicins, duocarmycins, doxorubicin, anthracyclines, amanitins, camptothecins.

In another embodiment, wherein the cytotoxin is N(2')-deacetyl-N(2')-(3-mercapto-1-oxopropyl)-maytansine (DM1)

In another embodiment, the antibody is selected from the group consisting of a fragment antigen-binding Fab, a single-chain Fv (scFv), a (svFv)2, a scFv-CH3, a scFv-Fc, a diabody, a bispecific antibody, a phage-Fab and a phage-scFv.

In another embodiment, the antibody is an IgG molecule and/or a monoclonal antibody.

In another embodiment, the ratio of cytotoxin to antibody is 2-8:1, preferably 3-4:1.

Another aspect of the disclosure provides a method of treating a disease comprising administering an effective amount of:
 (a) a first cytotoxic agent comprising a first antibody thereof that specifically binds a first epitope of a target disease cell surface receptor, and
 (b) a second cytotoxic agent comprising a second antibody that specifically binds a second epitope of the target disease cell surface receptor,
 wherein at least one of the first and second cytotoxic agent comprises a cytotoxin, wherein the cytotoxin is linked directly or indirectly to the antibody,
 wherein at least one of the first and second cytotoxic agent comprises a radiolabel, wherein the radiolabel comprises a radionuclide and optionally a scaffold, wherein the scaffold is directly or indirectly coupled to the antibody,
 and wherein the first epitope is on a first extracellular domain of the target disease cell surface receptor and the second epitope is on a second extracellular domain of the target disease cell surface receptor.

In one embodiment, the first binding and second cytotoxic agent are administered simultaneously, sequentially or separately.

In another embodiment, the disease is cancer, optionally a solid tumour.

In another embodiment, the cell surface receptor is EGFR and the cancer is a cancer of epithelial origin, optionally squamous cell head & neck, glioma, non-small cell lung, colorectal, breast or cervical cancer.

In another embodiment, the cell surface receptor is HER2 and the cancer is a HER2 positive cancer, optionally a breast cancer.

In another embodiment, the first cytotoxic agent and/or the second cytotoxic agent are administered intravenously.

Another aspect of the disclosure provides a method of making a cytotoxic agent comprising:

coupling an antibody specific for a disease associated cell surface receptor with a cytotoxin to produce antibody drug conjugate (ADC);

optionally reacting the ADC with a bifunctional radionuclide chelator to produce a ADC-scaffold wherein the scaffold is conjugated to the antibody of the ADC;

radiolabeling the ADC or optionally the ADC-scaffold to produce the cytotoxic agent.

In another embodiment, the antibody is monoclonal antibody, optionally an antibody fragment or single chain antibody.

In another embodiment, the disease associated cell surface receptor is selected from an EGFR family member, EphA2 and IGF-1R.

In another embodiment, the cytotoxin is first reacted with a bifunctional linker, to produce a cytotoxin-linker and the cytotoxin-linker is reacted with the antibody to couple the antibody with the cytotoxin, optionally wherein the cytotoxin linker is reacted with the antibody using a 5-50 mole excess equivalent of cytotoxin linker.

In another embodiment, the coupling step is carried out under conditions to produce a cytotoxin to antibody ratio of approximately 3-4:1.

In another embodiment, the steps of reacting the ADC with a bifunctional radionuclide chelator and radiolabeling the ADC or optionally the ADC-scaffold are carried out under conditions to produce an antibody to radionuclide ratio of 1:1 to 1:3.

In another embodiment, the cytotoxin is selected from the group consisting of maytansine and derivatives thereof (maytansinoids), auristatins, calicheamicins, duocarmycins, doxorubicin, anthracyclines, amanitins and camptothecins.

In another embodiment, the bifunctional radionuclide chelator is p-SCN-Bz-DOTA.

In another embodiment, the method further comprises purifying the cytotoxic agent.

In another embodiment, the method comprises one or more steps described in Examples 6 to 8.

DRAWINGS

Embodiments are described below in relation to the drawings in which:

FIG. 1A is a schematic representation of an example of a radiolabeled immunoconjugate comprising a DOTA scaffold to chelate $^{225}$Ac and PEG6-DM1. The molecule can be referred to as $^{225}$Ac-antibody-PEG$_6$-DM1 radiolabeled immunoconjugate. Although the schematic shows only one cytotoxin attached to the antibody, the cytotoxic agent typically comprises 3-8 cytotoxins per antibody molecule. Cytotoxic agents comprising 3-4 DM1 cytotoxins per antibody molecule and $^{225}$Ac radionuclide, can be referred to as $^{225}$Ac-antibody-PEG$_6$-DM1-Low and cytotoxic agents comprising 7-8 DM1 cytotoxins per antibody molecule and $^{225}$Ac radionuclide can be referred to as $^{225}$Ac-antibody-PEG$_6$-DM1-High.

FIG. 2 (A-D) shows a flow cytometry analysis. A and B represent data for an MDA-MB-231 cell line; C and D represent data for an MCF-7 control Cell line.

Figure 1A:
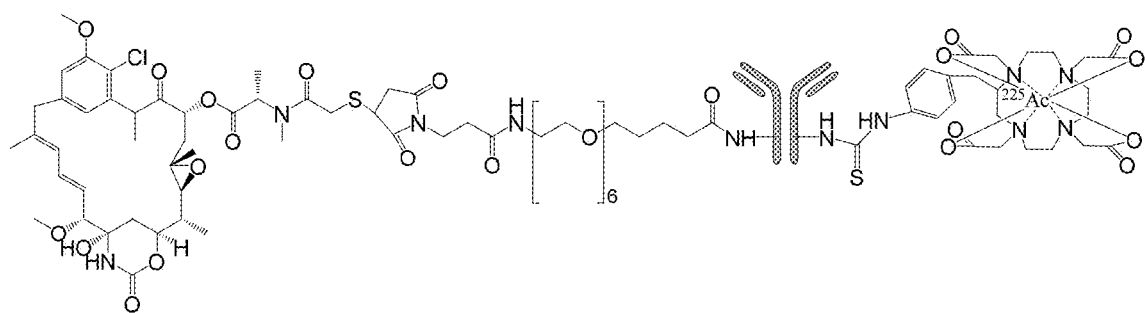
FIG. 1B is a schematic of $^{225}$Ac-antibody.
FIG. 1D is a schematic of $^{225}$Ac-antibody-PEG$_6$-DM1 using macropa-NCS to chelate the $^{225}$Ac.
FIG. 1E is a schematic of an antibody-PEG$_6$-DM1.
FIG. 1F is a schematic of $^{225}$Ac-antibody using macropa-NHS to chelate the $^{225}$A.
Figure 1B:
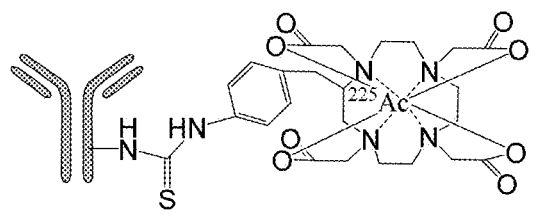
Figure 1C:
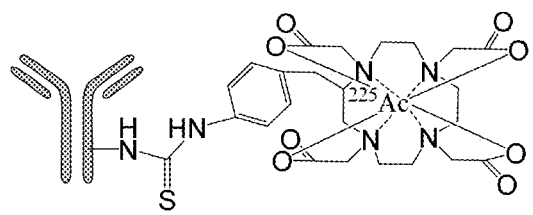
Figure 1D:
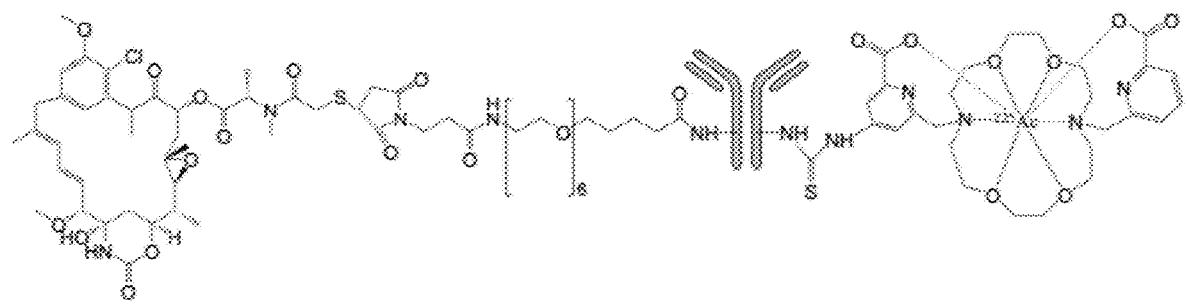
Figure 1E:
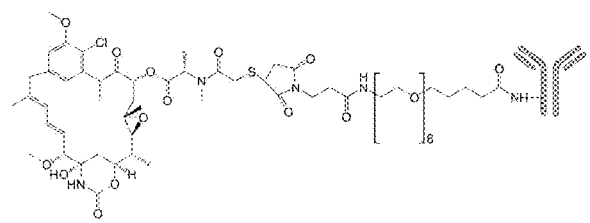
Figure 1F:
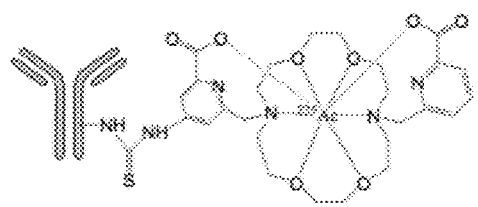
Figure 2A:
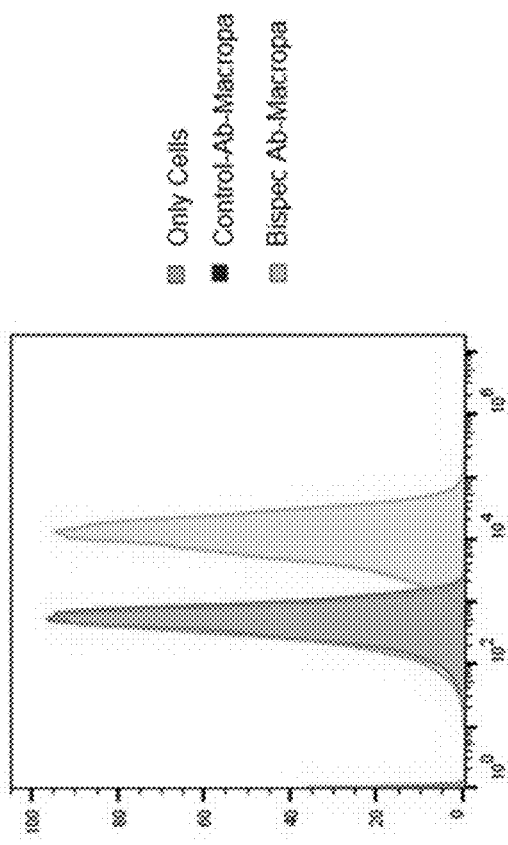
Figure 2B:
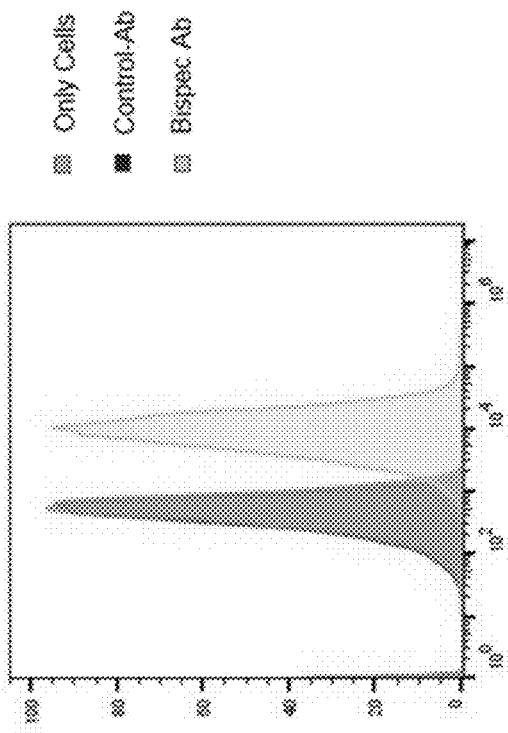
Figure 2C:
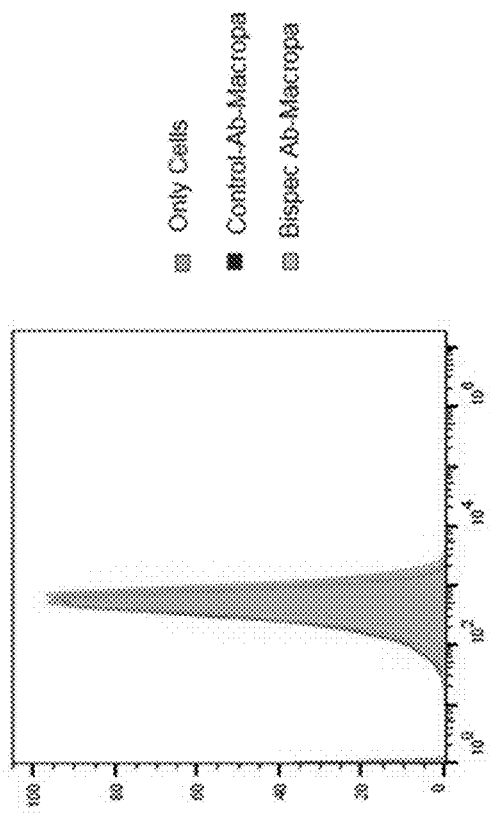
Figure 2D:
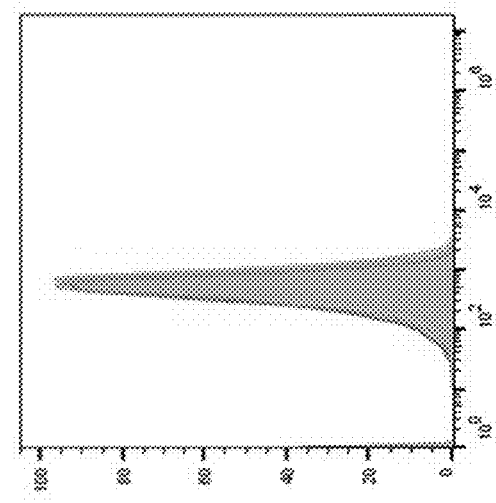
Figure 3A:
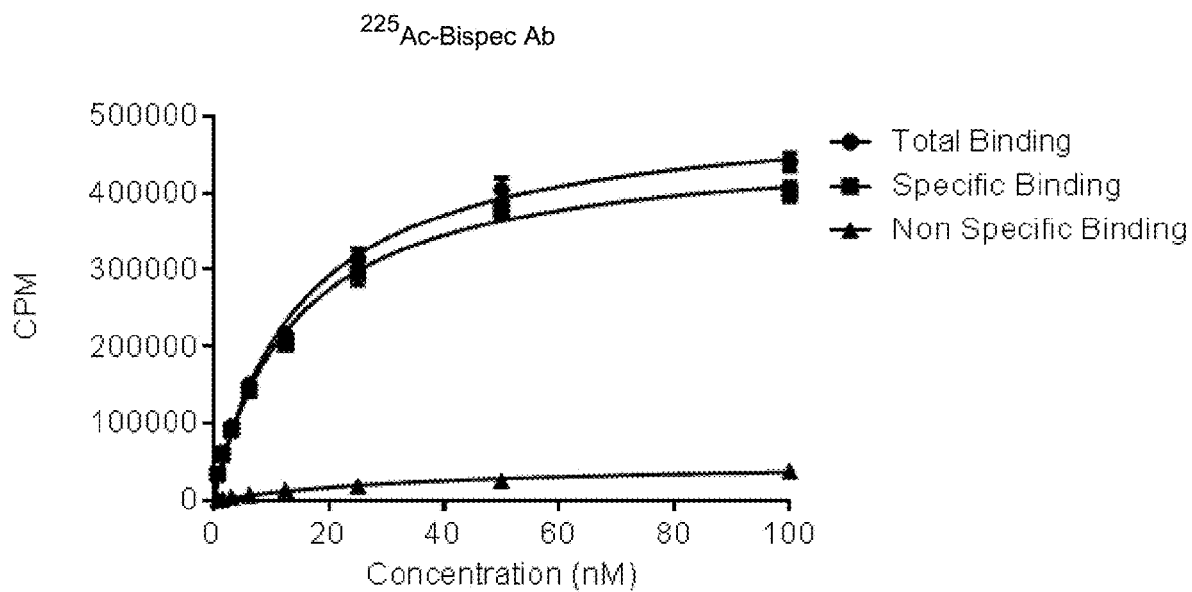
Figure 3B:
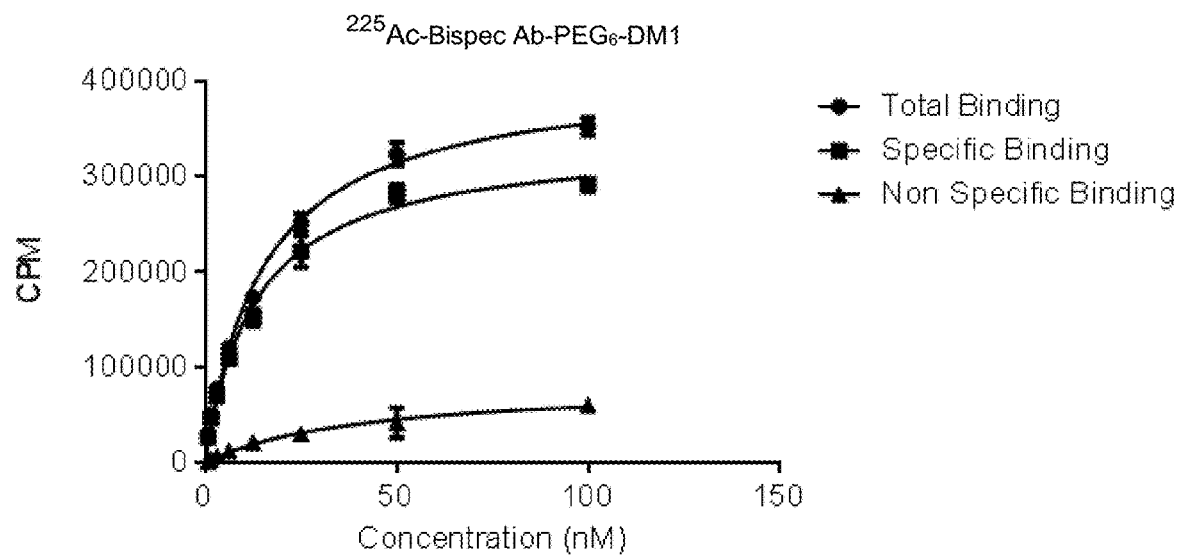

FIG. 3 (A, B) shows a radioligand binding assay for A) $^{225}$Ac-Bispec Ab and B) $^{225}$Ac-Bispec Ab-PEG$_6$-DM1 towards MDA-MB-231 cells.

FIG. 4 (A-D) shows an internalization assay performed with MDA-MB-231 cells treated with A) Bispec Ab, B) Bispec Ab-PEG$_6$-DM1, C) $^{225}$Ac-Bispec Ab and D) $^{225}$Ac-Bispec Ab-PEG$_6$-DM1.

Figure 5:
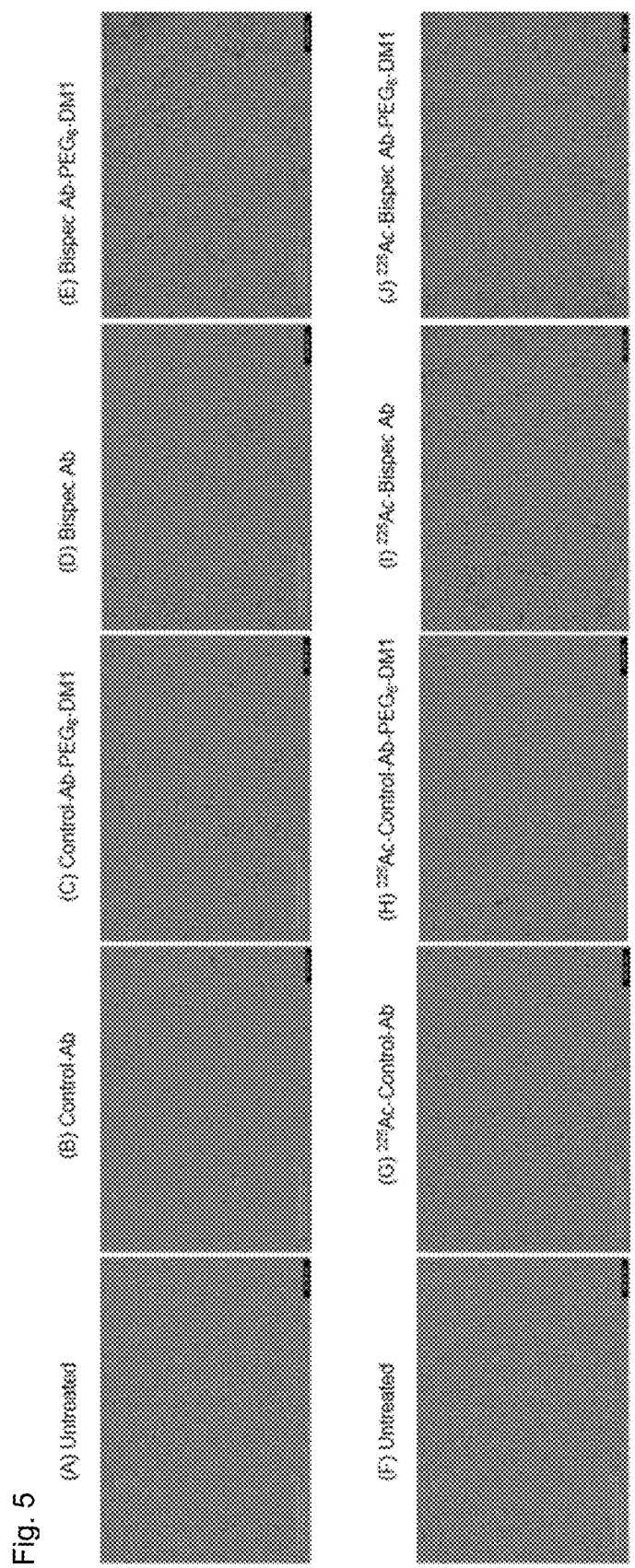

FIG. 5 (A-J) shows microscopic images for internalization of radiolabelled and non-radiolabelled immunoconjugate.

Figure 6A:
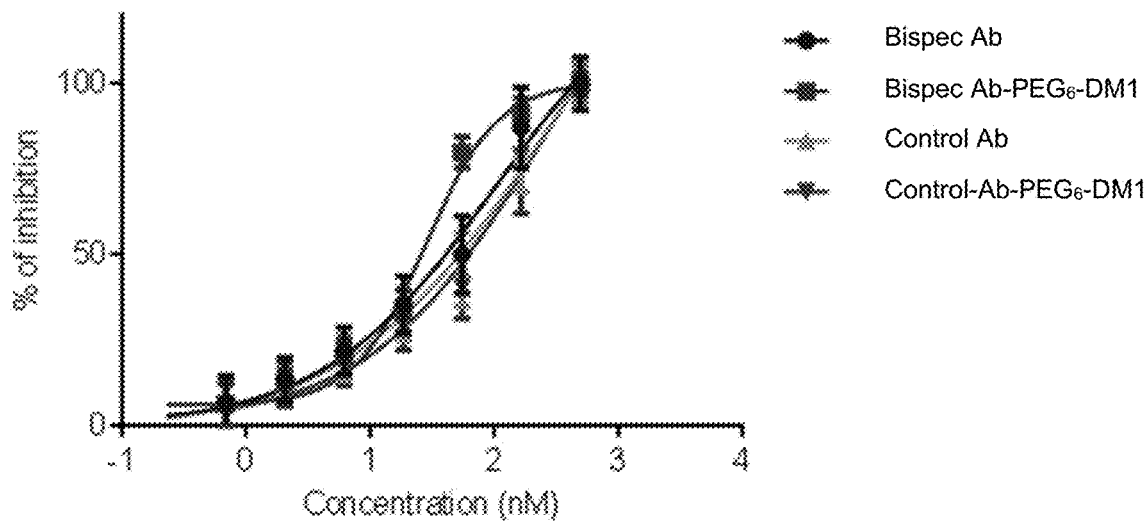
Figure 6B:
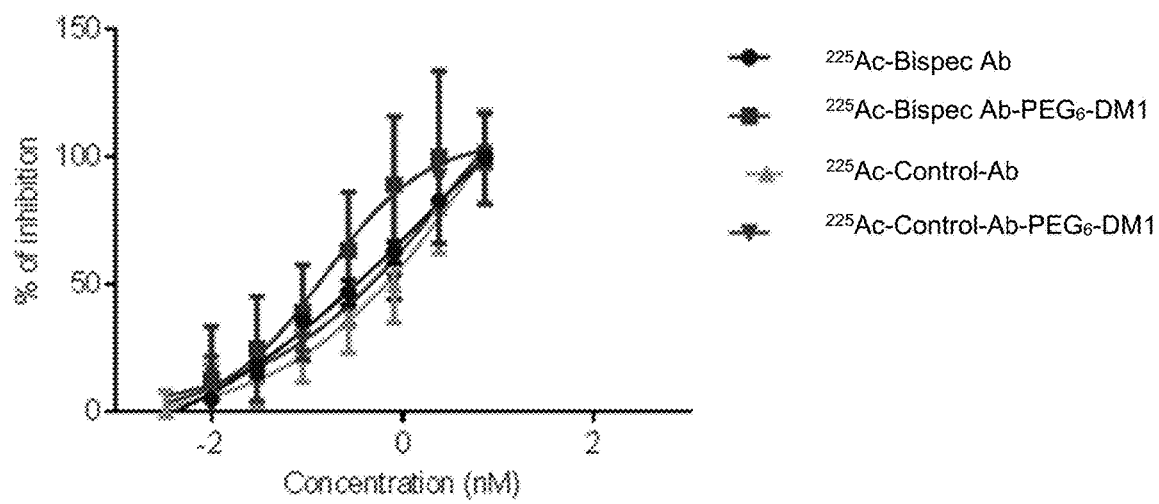
Figure 7:
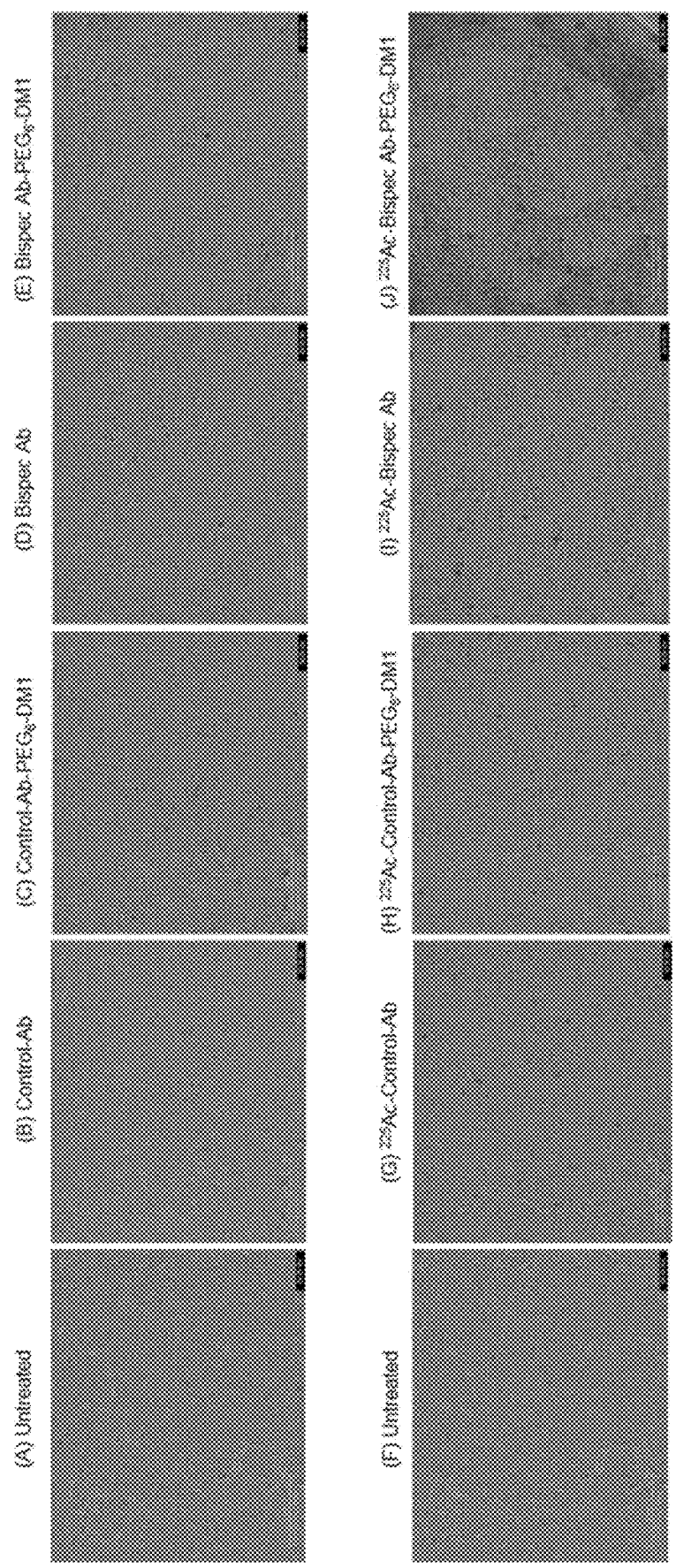

FIG. 6 (A, B) shows in vitro cytotoxicity of radiolabelled and non radiolabelled immunoconjugate towards MDA-MB-231 cells FIG. 7 shows microscopic images for in vitro cytotoxicity of radiolabelled and non-radiolabelled immunoconjugate.

Figure 8A:
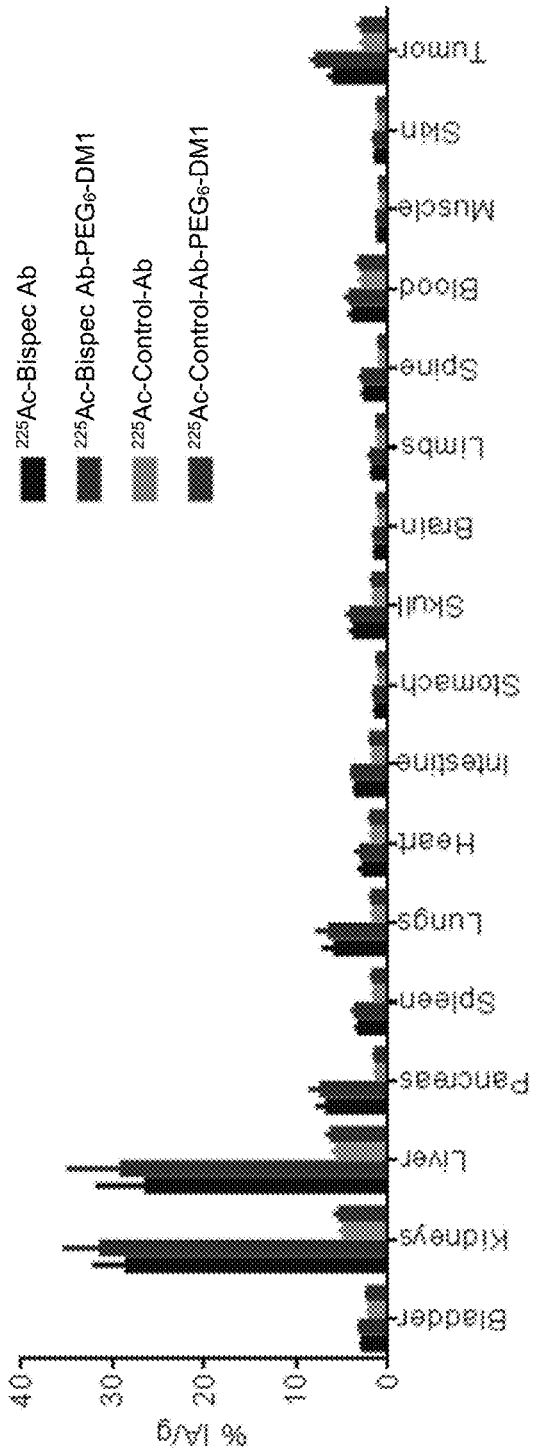
Figure 8B:
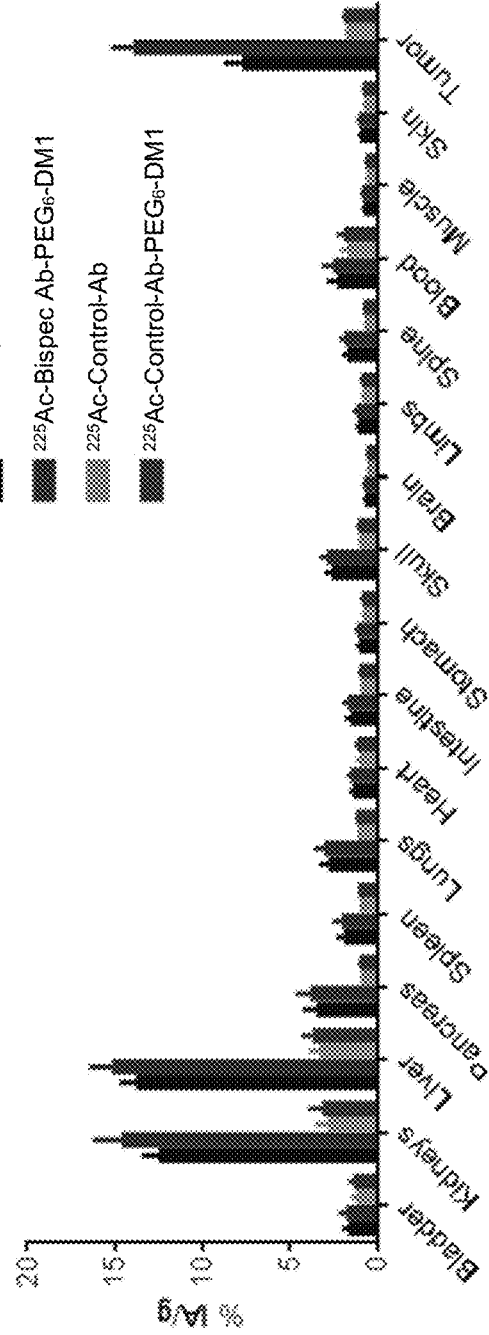

FIG. 8 (A, B) shows biodistribution studies performed in CD-1 nude mice bearing MDA-MB-231 tumor at A) 24 h, B) 168 h p.i.

FIG. 9 (A-H) shows in vivo efficacy of Bispec Ab and its conjugates in MDA-MB-231 xenograft model in CD-1 nude mice. Tumor volumes of individual mice (represented by the different colors), A) $^{225}$Ac-Bispec Ab, B) $^{225}$Ac-Bispec Ab-PEG$_6$-DM1, C) $^{225}$Ac-Control Ab, D) $^{225}$Ac-Control Ab-PEG$_6$-DM1, E) Bispec Ab, F) Bispec Ab-PEG$_6$-DM1, G) PBS and H) Kaplan-Meier curves for overall survival in CD-1 mice bearing MDA-MB-231 xenografts. When xenografts reached the appropriate size, mice were randomized into 8 mice per group and treated on day 0, 14 and 26. The endpoint was when xenograft volume reached 2500 mm3. Log-rank test analysis demonstrated that the survival of the PBS group was significantly different from other groups ($p<0.0001$).

Figure 10:
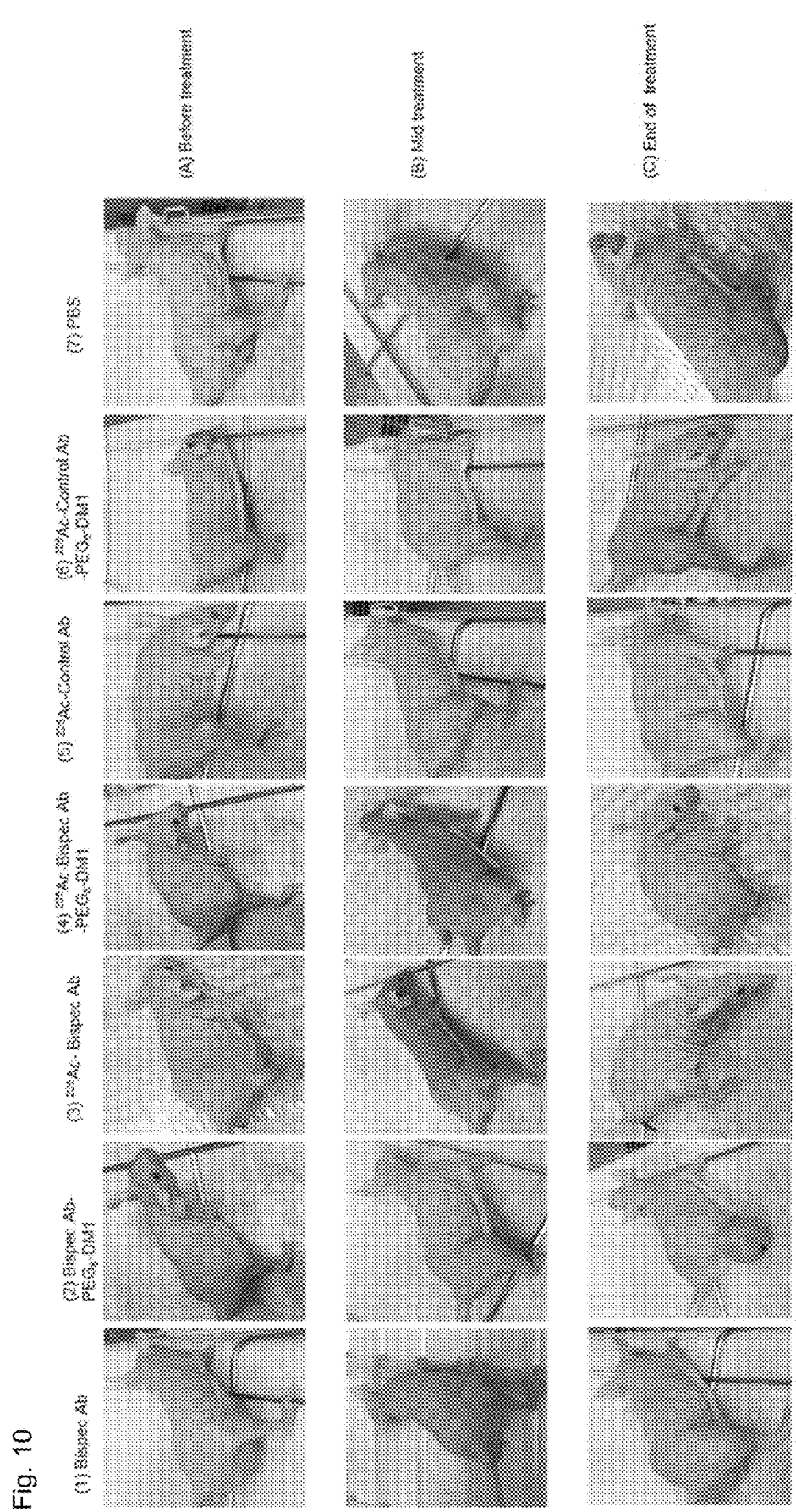
FIG. 10 is a schematic of an antibody drug conjugate (ADC). Although the schematic shows only one cytotoxin attached to the antibody, the cytotoxic agent typically comprises 3-8 cytotoxins per antibody molecule.

FIG. 10 shows pictures of representative mice before and at the end of the study following treatment with $^{225}$Ac-Bispec Ab-PEG$_6$-DM1 and other groups including controls.

Figure 11:
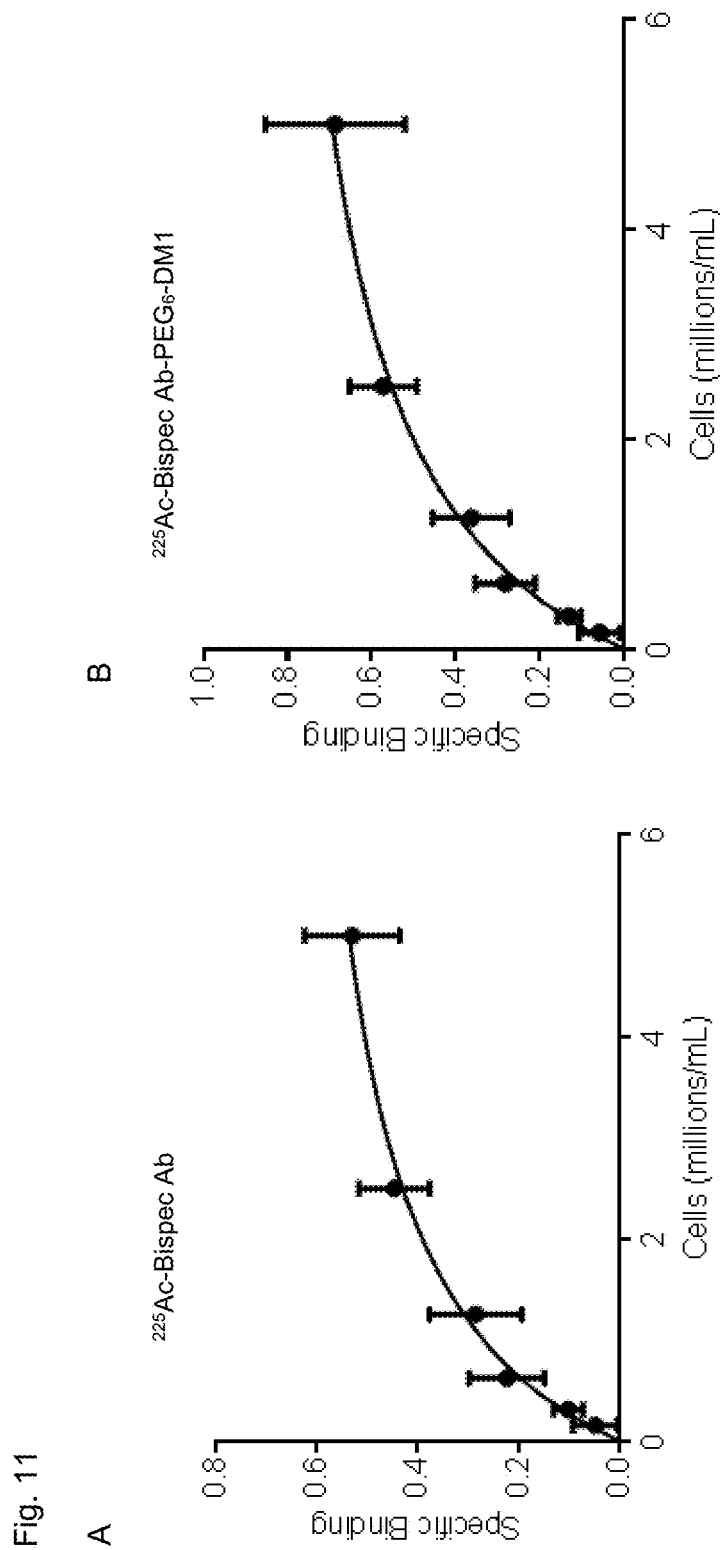

FIG. 11 shows a Lindmo Assay (immunoreactivity of the radioimmunoconjugates) A) $^{225}$Ac-Bispec Ab, B) $^{225}$Ac-Bispec Ab-PEG$_6$-DM1-Low towards MDA-MB-231 cells.

Figure 12:
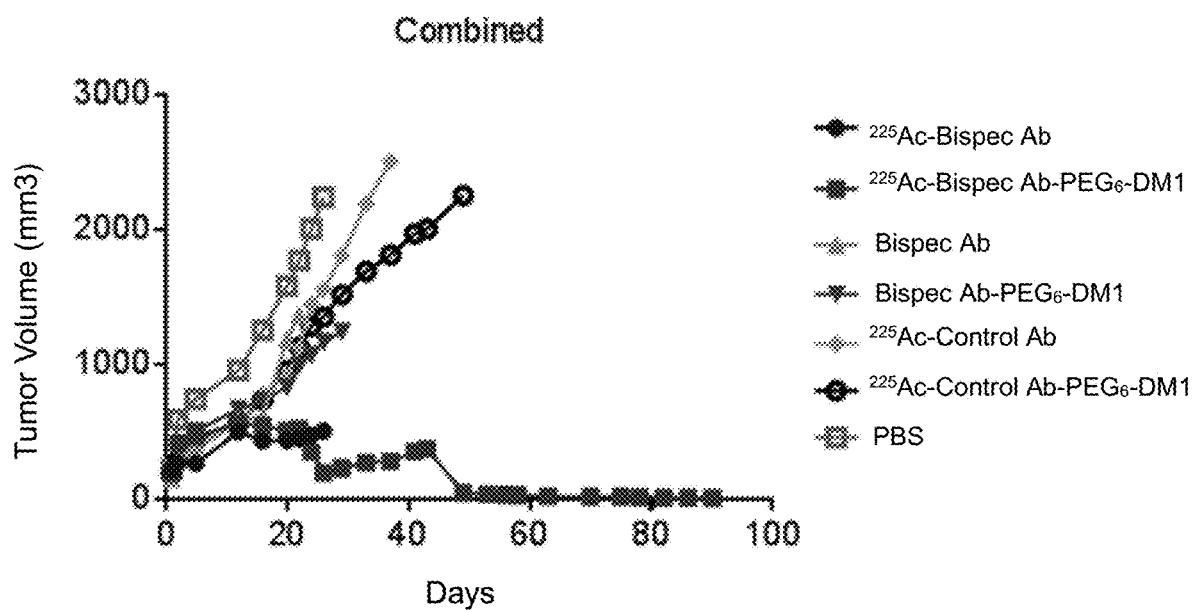

FIG. 12 shows tumor growth curves of the different treatment groups. 6/7 mice were cured without any signs of recovery for >3 months after the end of the study.

Figure 13:
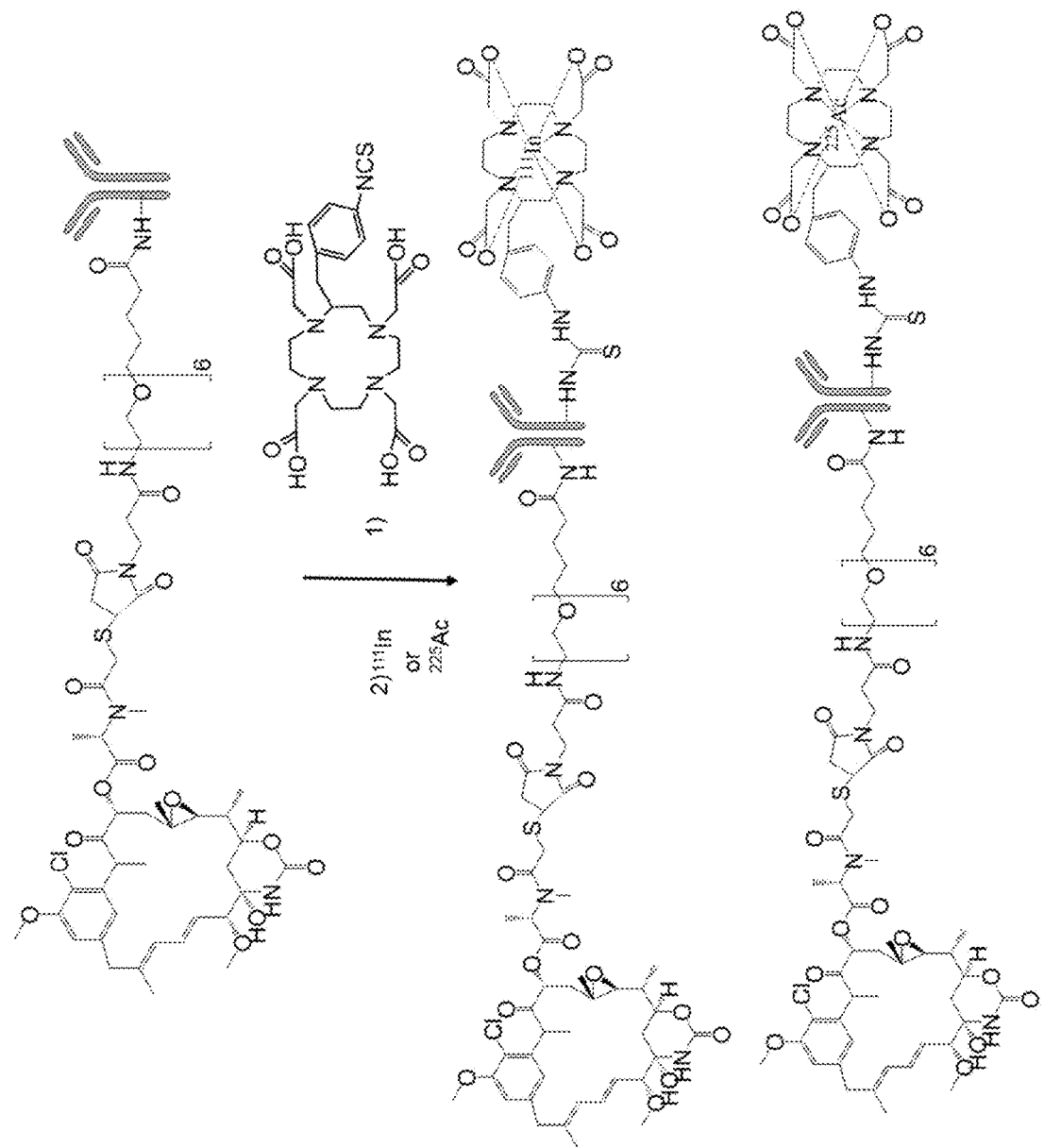

FIG. 13 shows anti-IGF-1R antibody cixutumumab linked to DM1 and radiolabeled with $^{225}$Ac using DOTA as a chelator ($^{225}$Ac-cixutumumab-PEG6-DM1).

Figure 14:
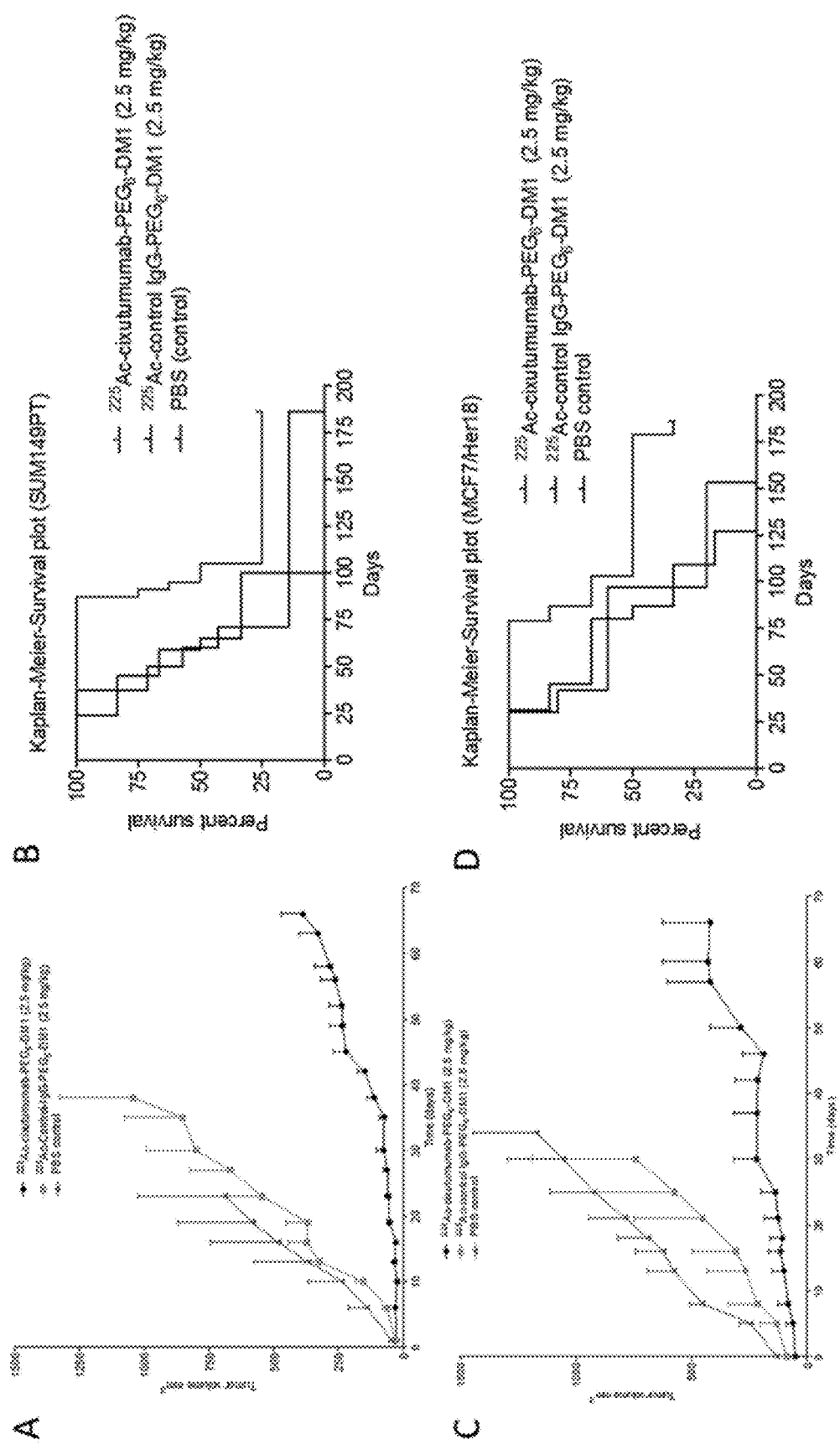

FIG. 14 shows the efficacy of cixutumumab-PEG$_6$-DM1 drug conjugates in IGF-1R positive SUM149PT and MCF7/Her-18 mouse xenograft. A) SUM149PT tumor growth curves of each mouse treated with PBS, 50 µg dose of $^{225}$Ac-cixutumumab-PEG$_6$-DM1 (2×, 225 nCi, 0 and 14 days interval, 2.5 mg/kg) and $^{225}$Ac-control-IgG-PEG$_6$-DM1 (2×, 225 nCi, 0 and 14 days interval, 2.5 mg/kg). B) Kaplan-Meier SUM149PT xenograft survival curves. Study endpoint occurred when xenograft volume reached 2000 mm$^3$. C) MCF7/Her18 tumor growth curves of each mouse treated with PBS, 50 µg dose of $^{225}$Ac-cixutumumab-PEG$_6$-DM1 (2×, 225 nCi, 0 and 14 days interval, 2.5 mg/kg) and $^{225}$Ac-control-IgG-PEG$_6$-DM1 (2×, 225 nCi, 0 and 14 days interval, 2.5 mg/kg). D) Kaplan-Meier MCF7/Her18 xenograft survival curves. Study endpoint occurred when xenograft volume reached 2000 mm3.

Figure 15:
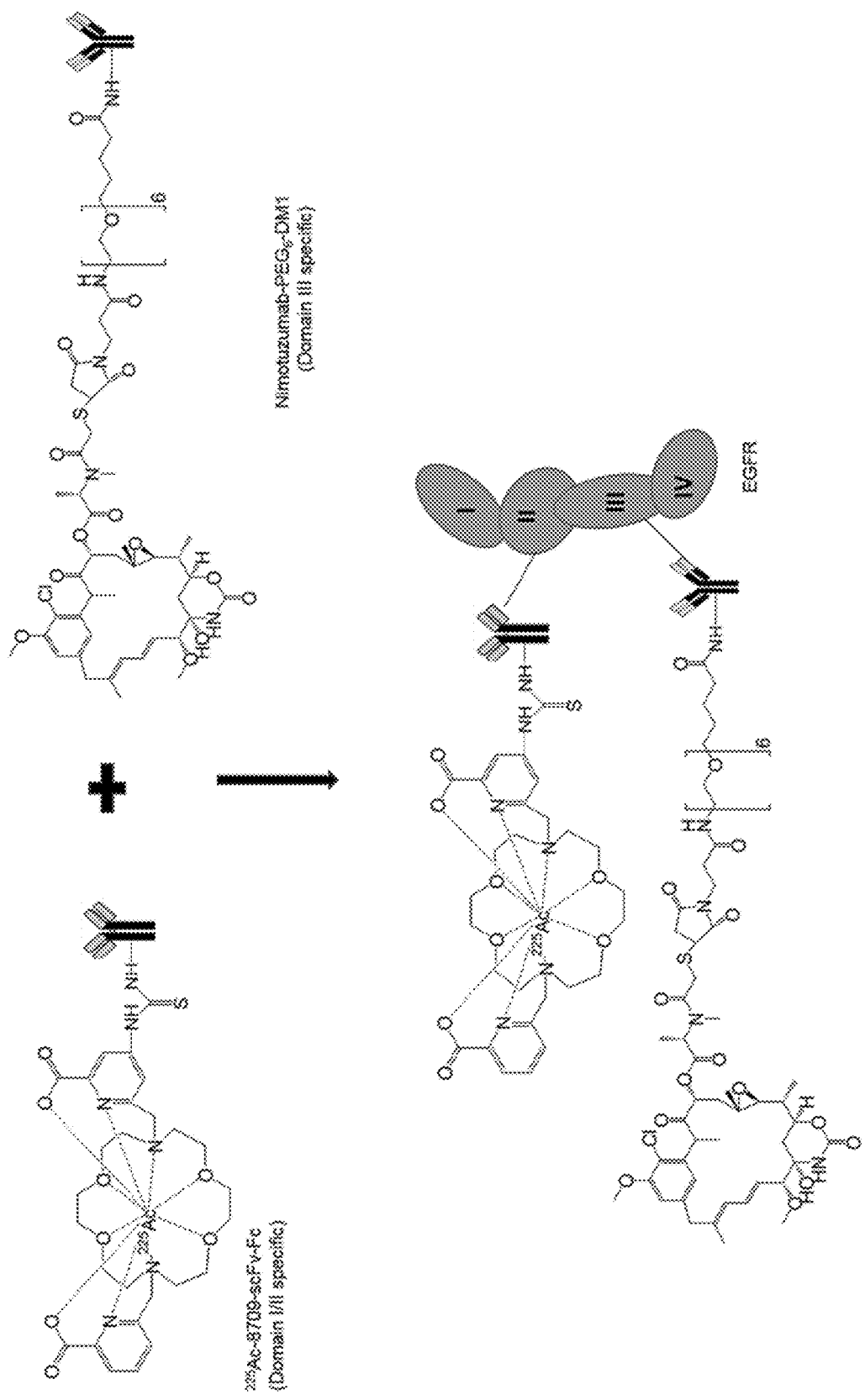

FIG. 15 shows $^{225}$Ac-8709-scFv-Fc and Nimotuzumab-PEG6-DM1.

FIG. 16A shows bioanalyzer data used to determine molecular weights and purities of ADCs. FIGS. 16B and C show saturation binding curves used to determine the binding constants $K_D$ at which immunoconjugates bind to the cell.

Figure 17B:
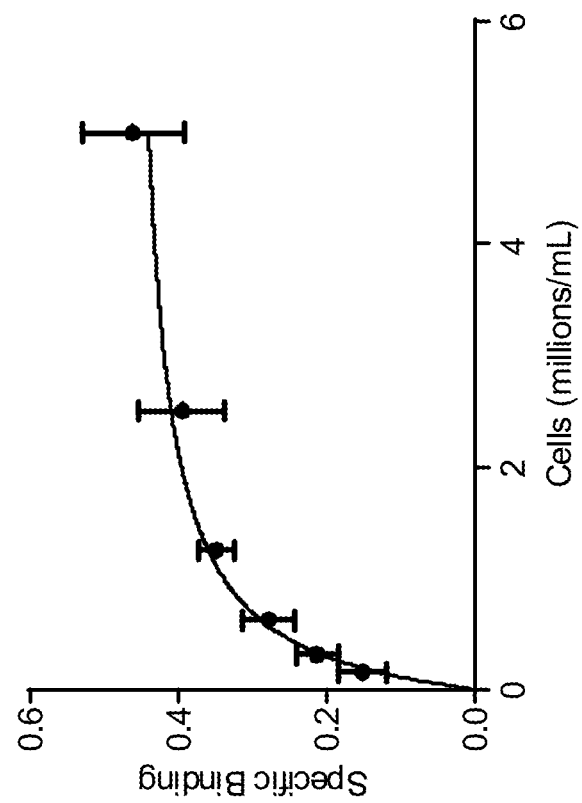

FIG. 17 (A, B) shows a radioligand binding assay towards MDA-MB-468 cells.

Figure 18:
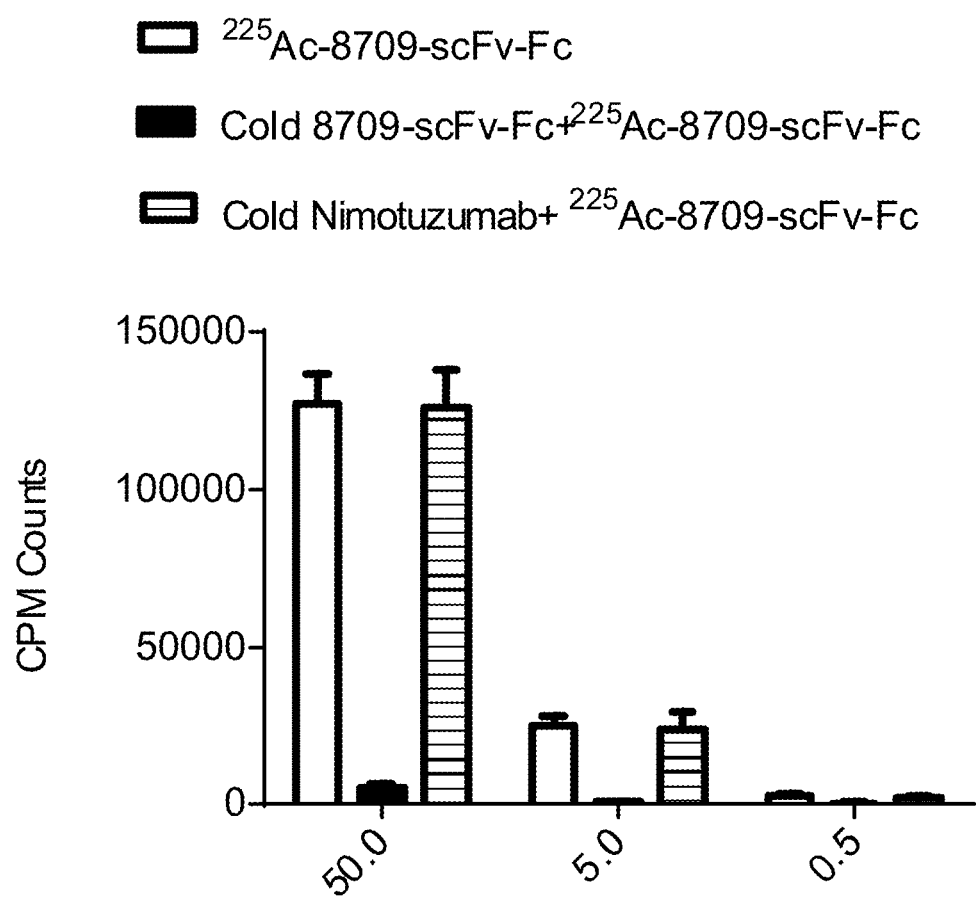

FIG. 18 shows a competitive binding experiment studying binding of 8709-scFv-Fc to EGFR domain II.

Figure 19D:
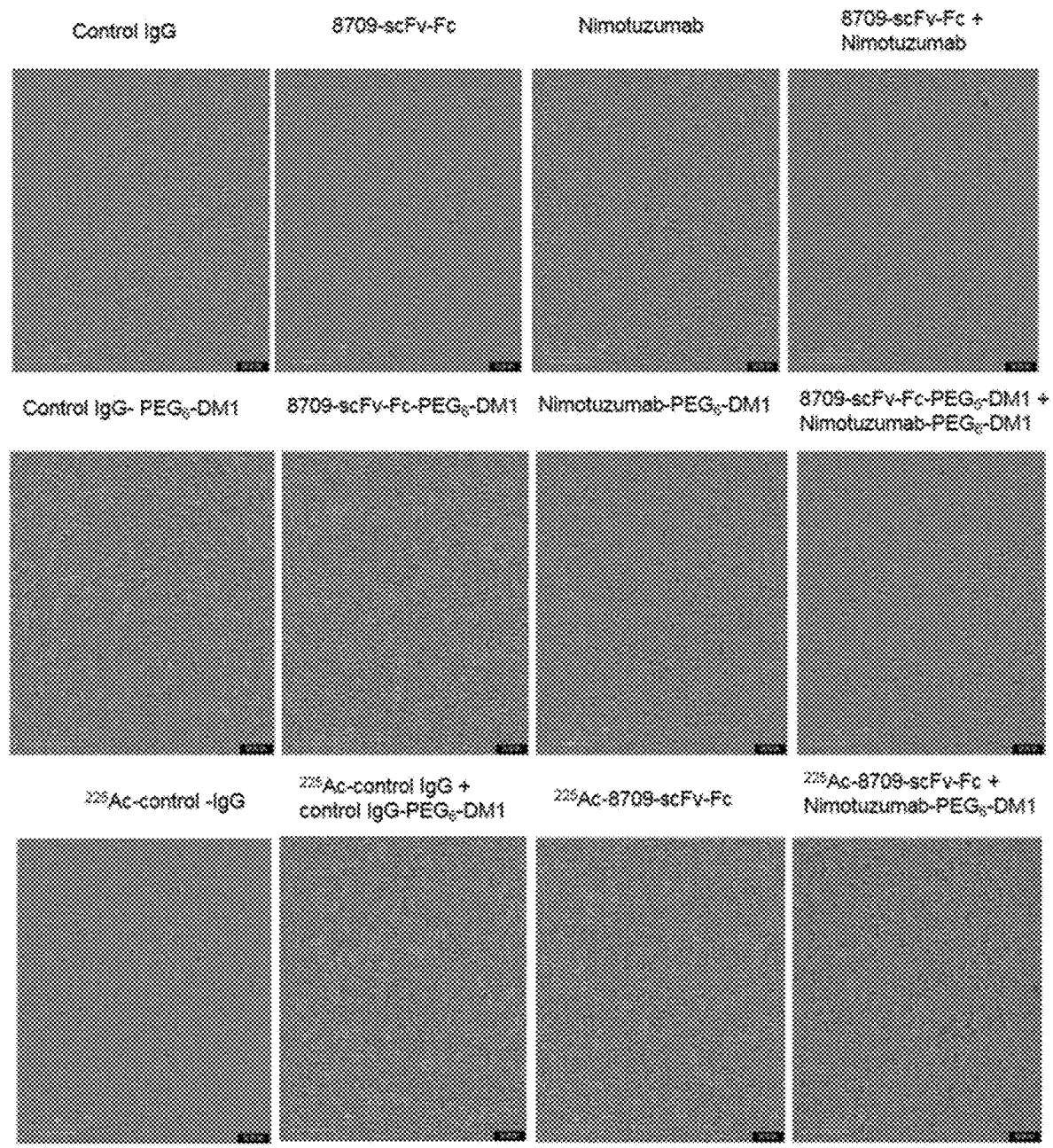

FIG. 19A-C shows an assessment of internalization of immunoconjugates. FIG. 19D shows microscopic images confirmed enhanced internalization.

Figure 20A:
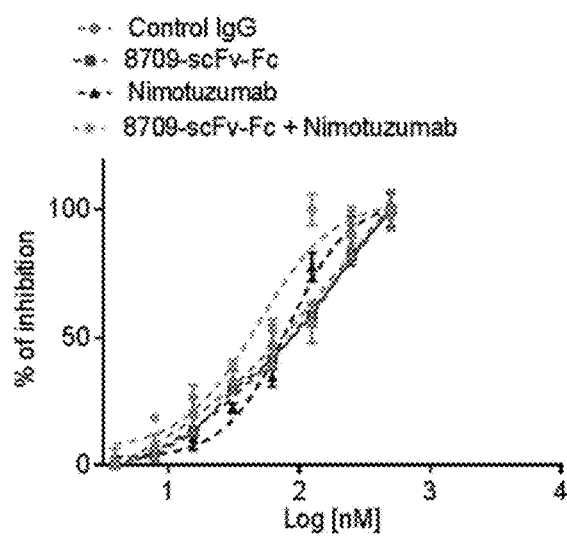
Figure 20B:
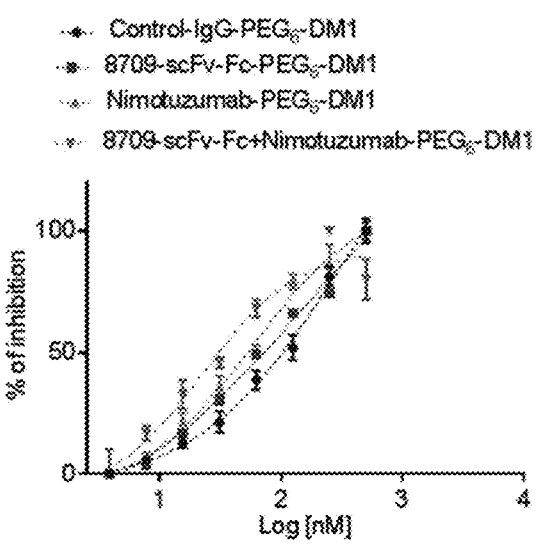
Figure 20C:
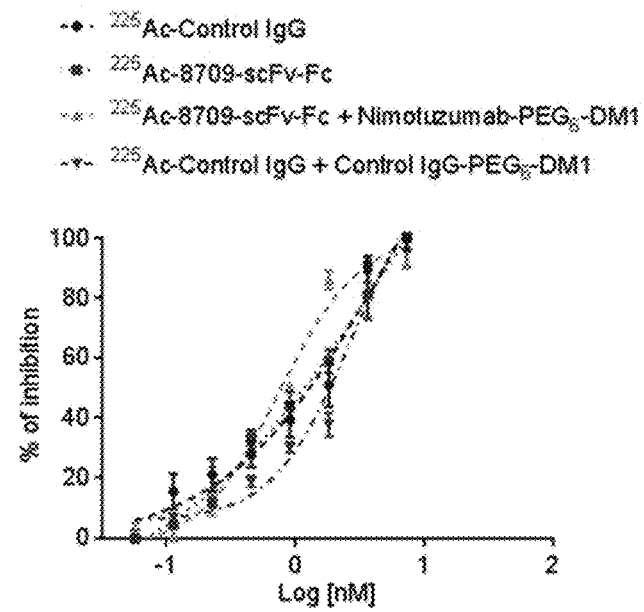
Figure 20D:
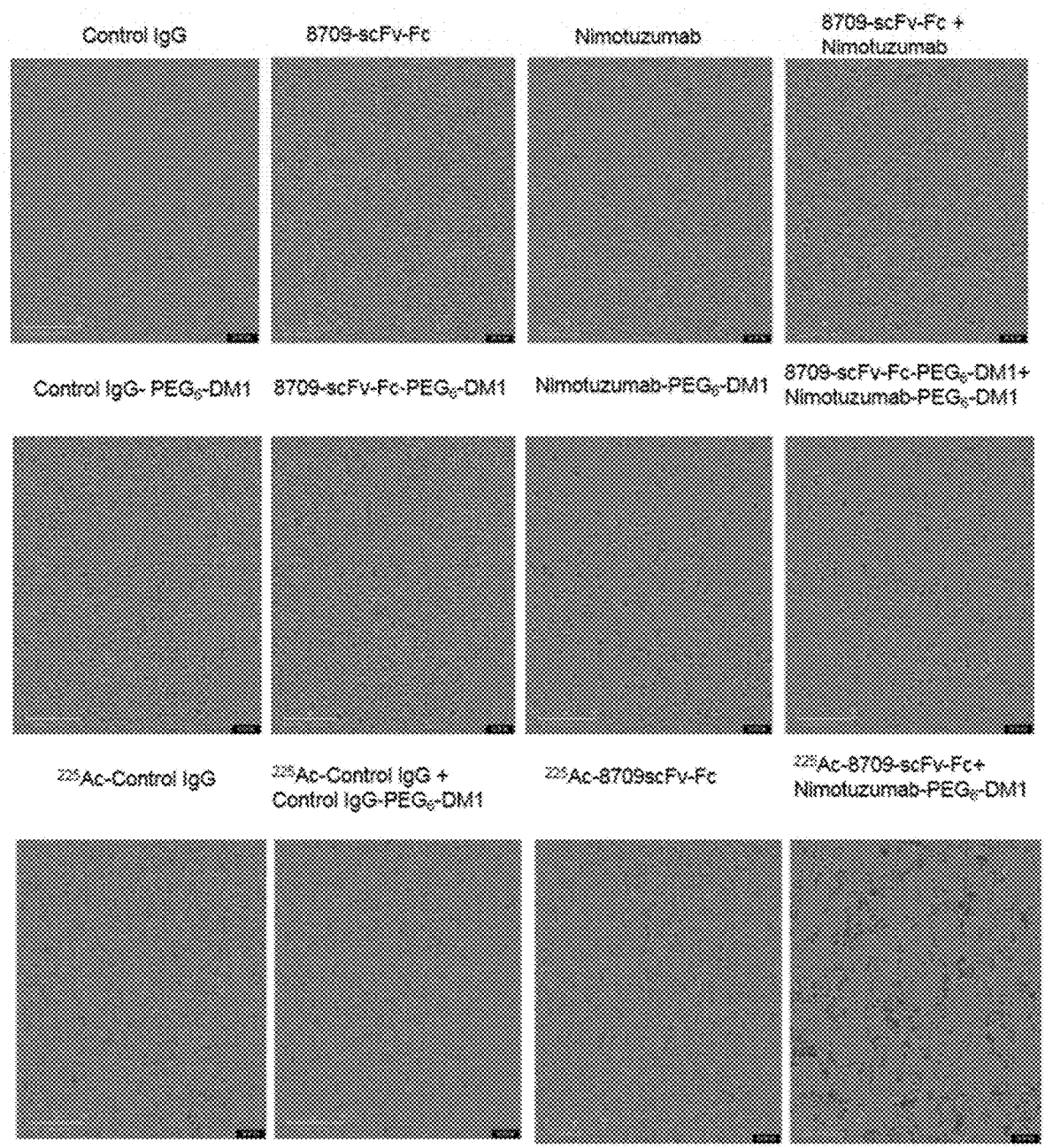

FIG. 20A-C shows in vitro cytotoxicity of immunoconjugates performed in three breast cancer cell lines MDA-MB-468, MDA-MB-231 and TrR1. FIG. 20D shows microscope images of corresponding samples.

Figure 21B:
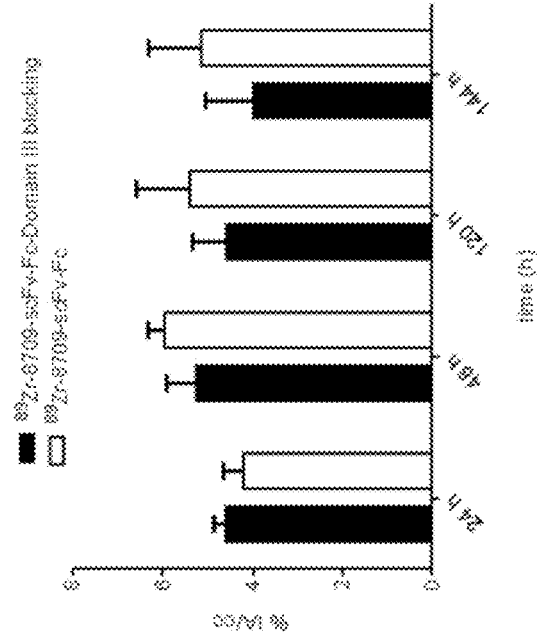
Figure 21D:
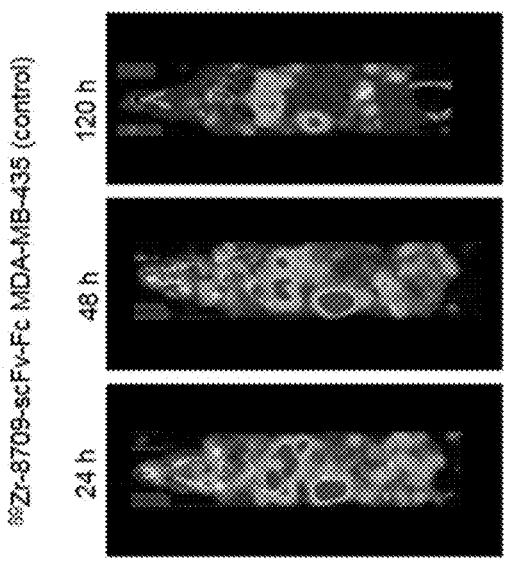
Figure 21A:
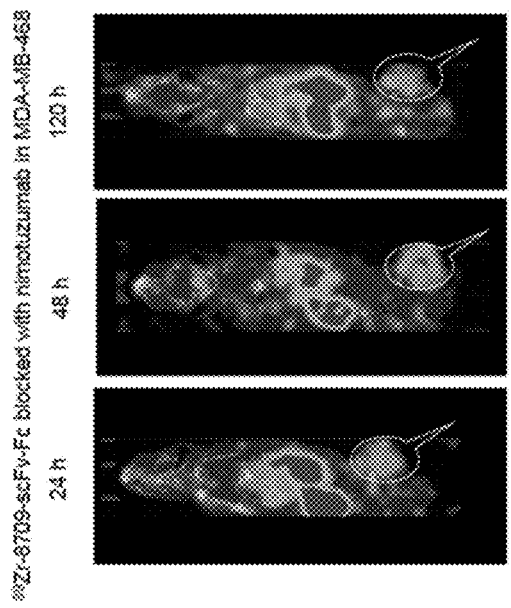
Figure 21C:
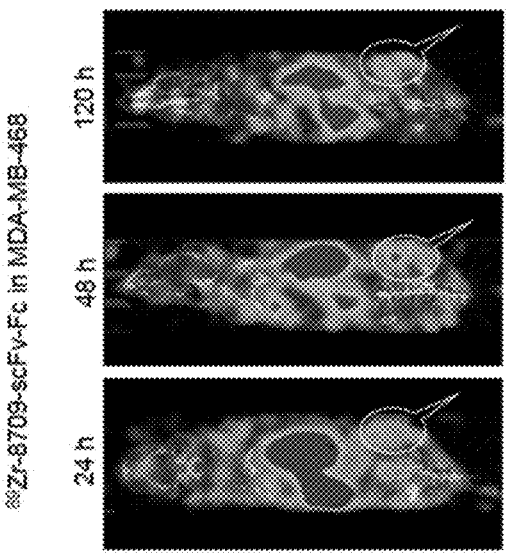

FIG. 21A-C shows in vivo binding of $^{89}$Zr-8709-scFv-Fc to domain II of EGFR was studied using microPET imaging at different time points 24 h, 48 h and 120 h p.i. FIG. 21D shows mice injected with unlabeled nimotuzumab before the injection of $^{89}$Zr-8709-scFv-Fc also displayed similar tumor uptake starting at 4.60±0.449% at 24 h and 4.57±1.30% at 120 h.

Figure 22A:
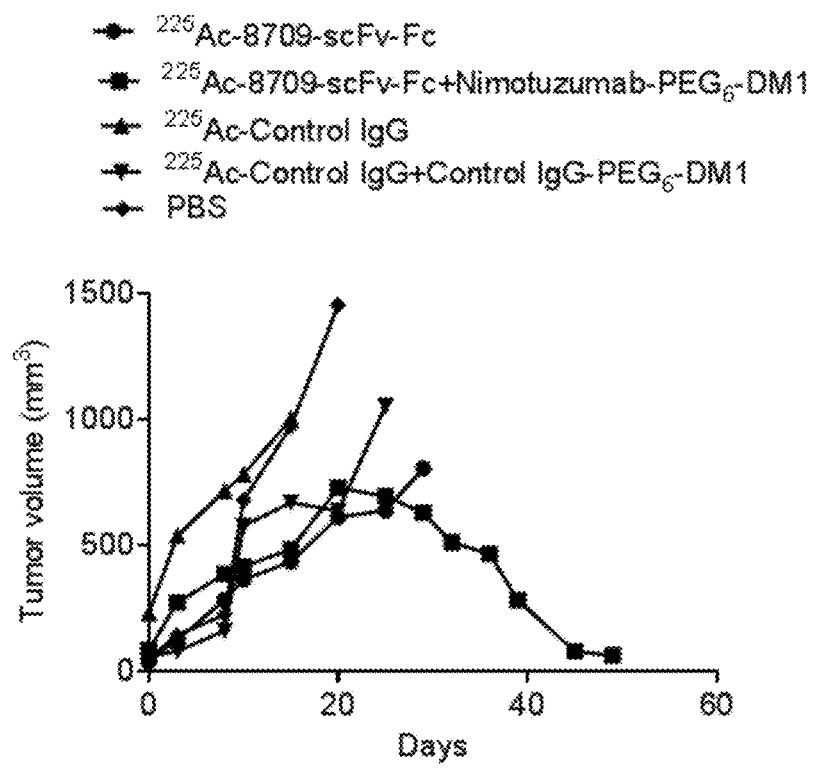
Figure 22B:
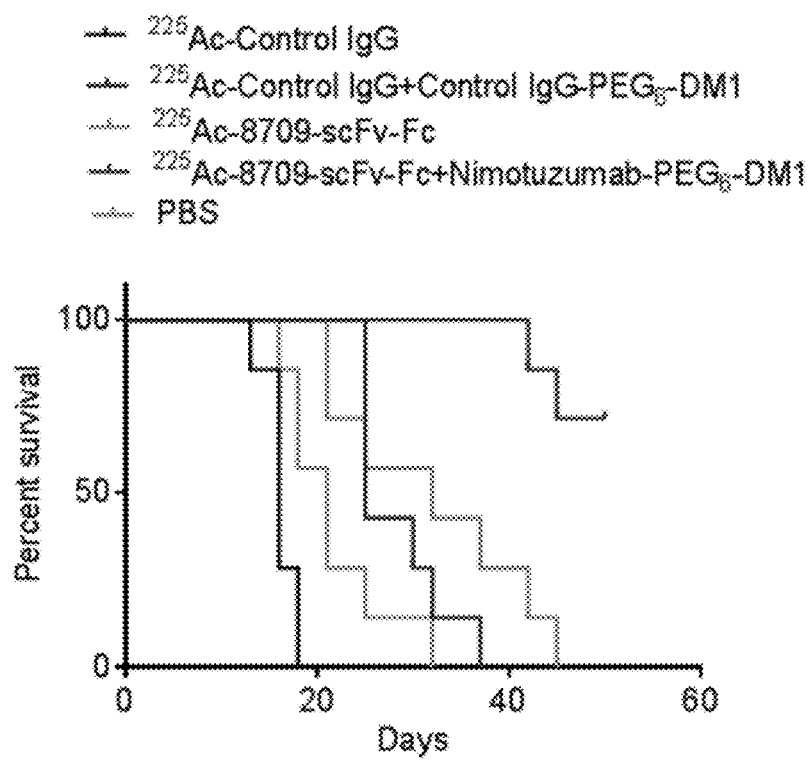

FIG. 22A shows the efficacy of simultaneous targeting of domains I/II and III was explored using $^{225}$Ac-labeled immunoconjugate ($^{225}$Ac-8709-scFv-Fc) plus antibody drug conjugate (nimotuzumab-PEG$_6$-DM1) in an EGFR-positive MDA-MB-468 mouse xenograft model. FIG. 22B shows Kaplan Meier curves calculated for all the groups.

FIG. 23 shows nimotuzumab radiolabeled using DOTA (commercial chelator) as chelator for $^{225}$Ac and conjugated to DM1.

Figure 24:
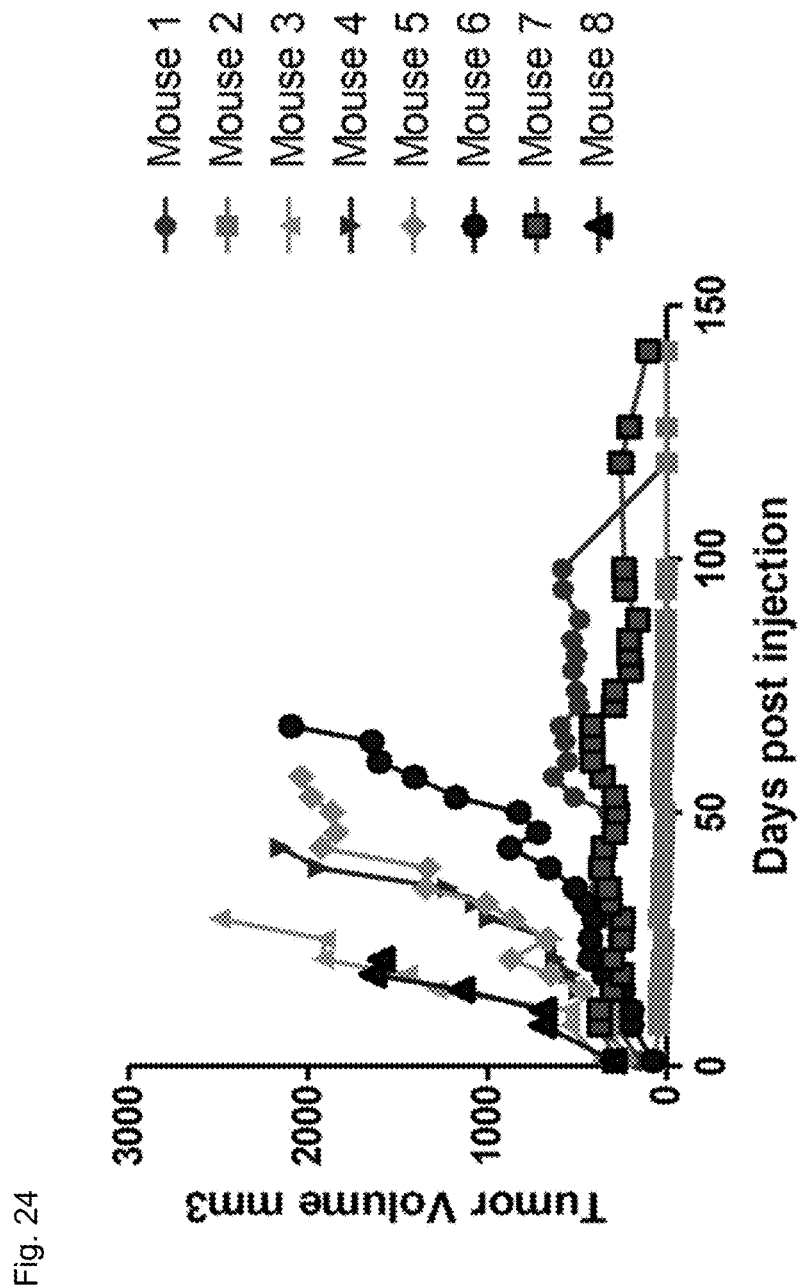

FIG. 24 shows 3/8 mice bearing DLD-1 colorectal tumors were completely cured by treatment with $^{225}$Ac-Nimotuzumab-PEG$_6$-DM1-low.

Figure 25:
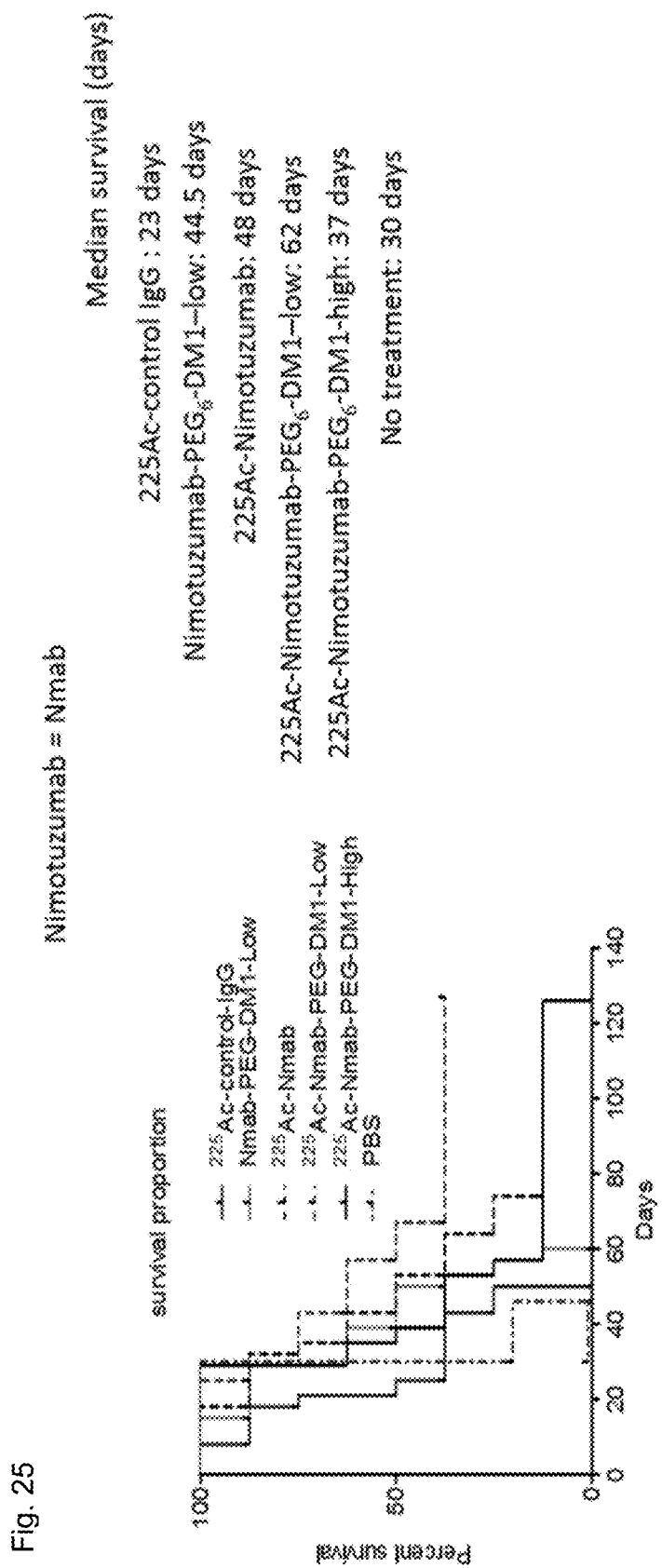

FIG. 25 shows Kaplan Meier survival curves for $^{225}$Ac-Nimotuzumab-PEG$_6$-DM1-low using a DLD-1 colorectal cancer tumor model.

Figure 26A:
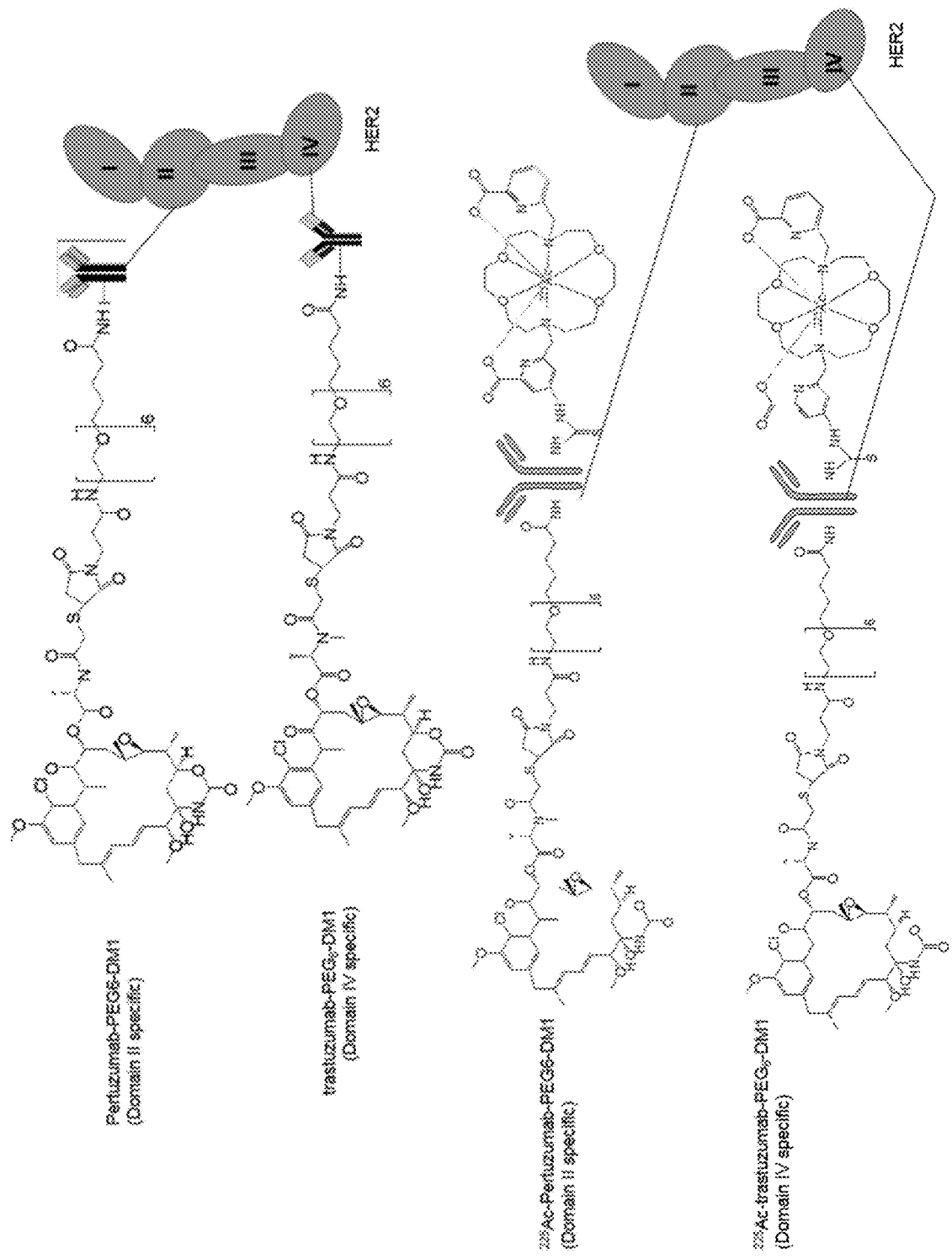
Figure 26B:
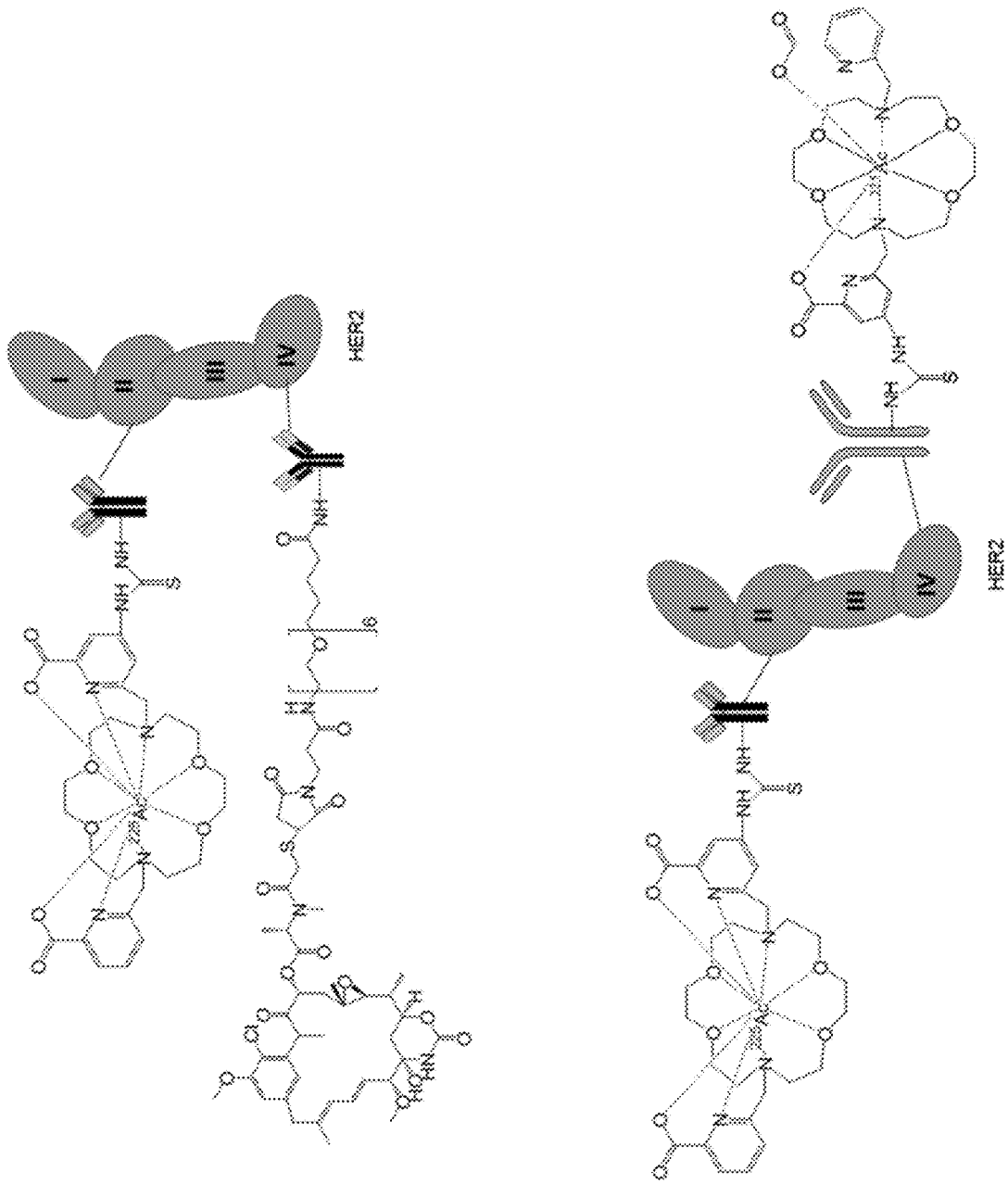
Figure 27A:
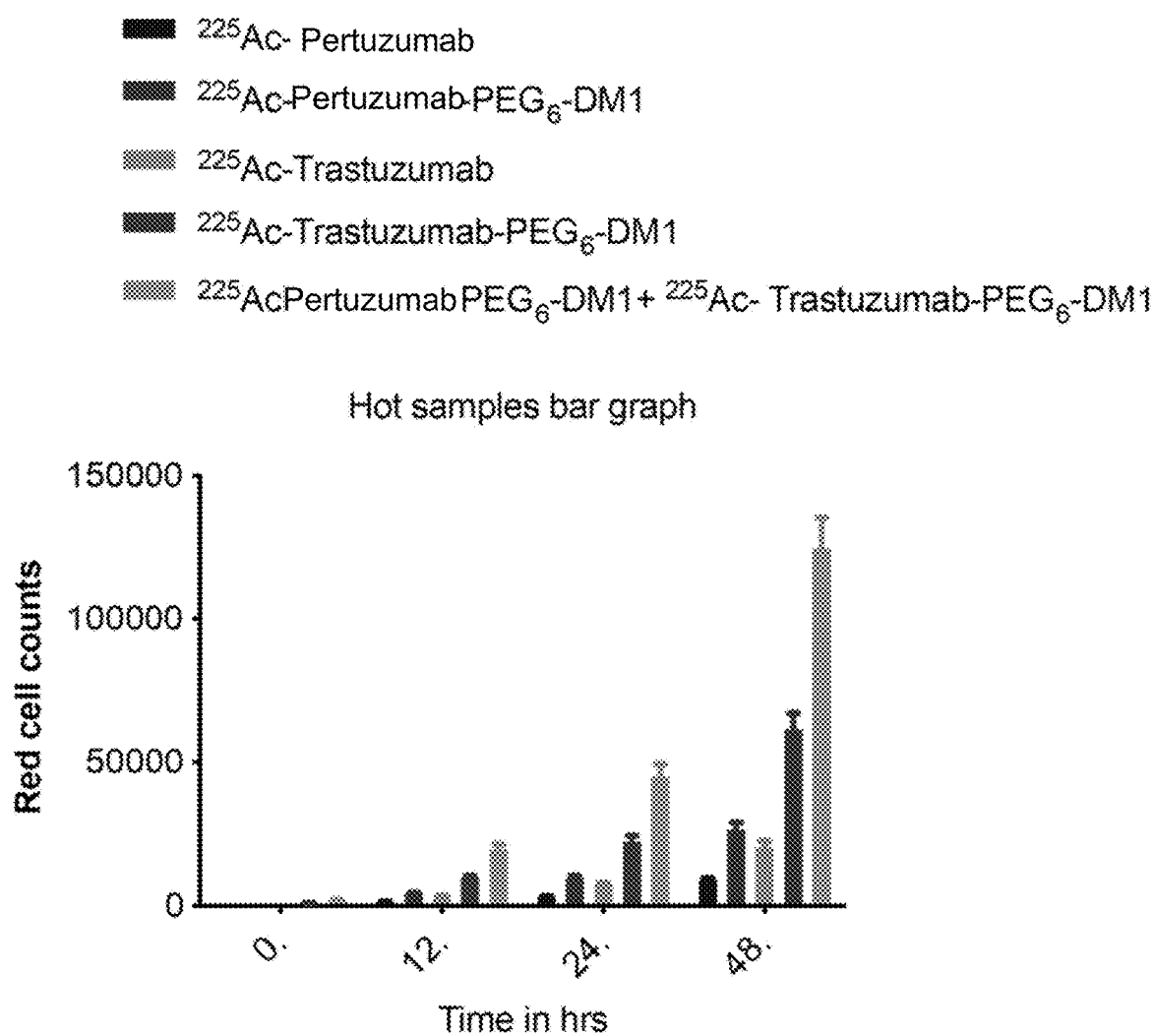
Figure 27B:
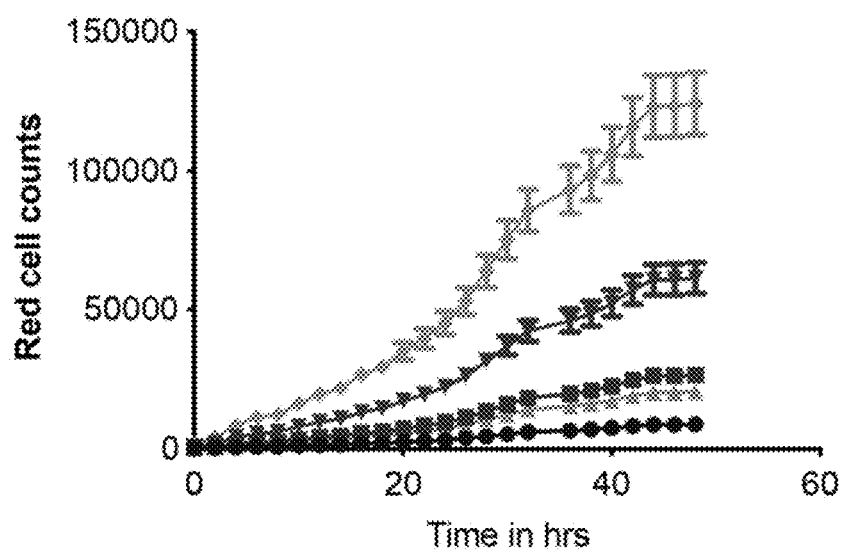
Figure 27C:
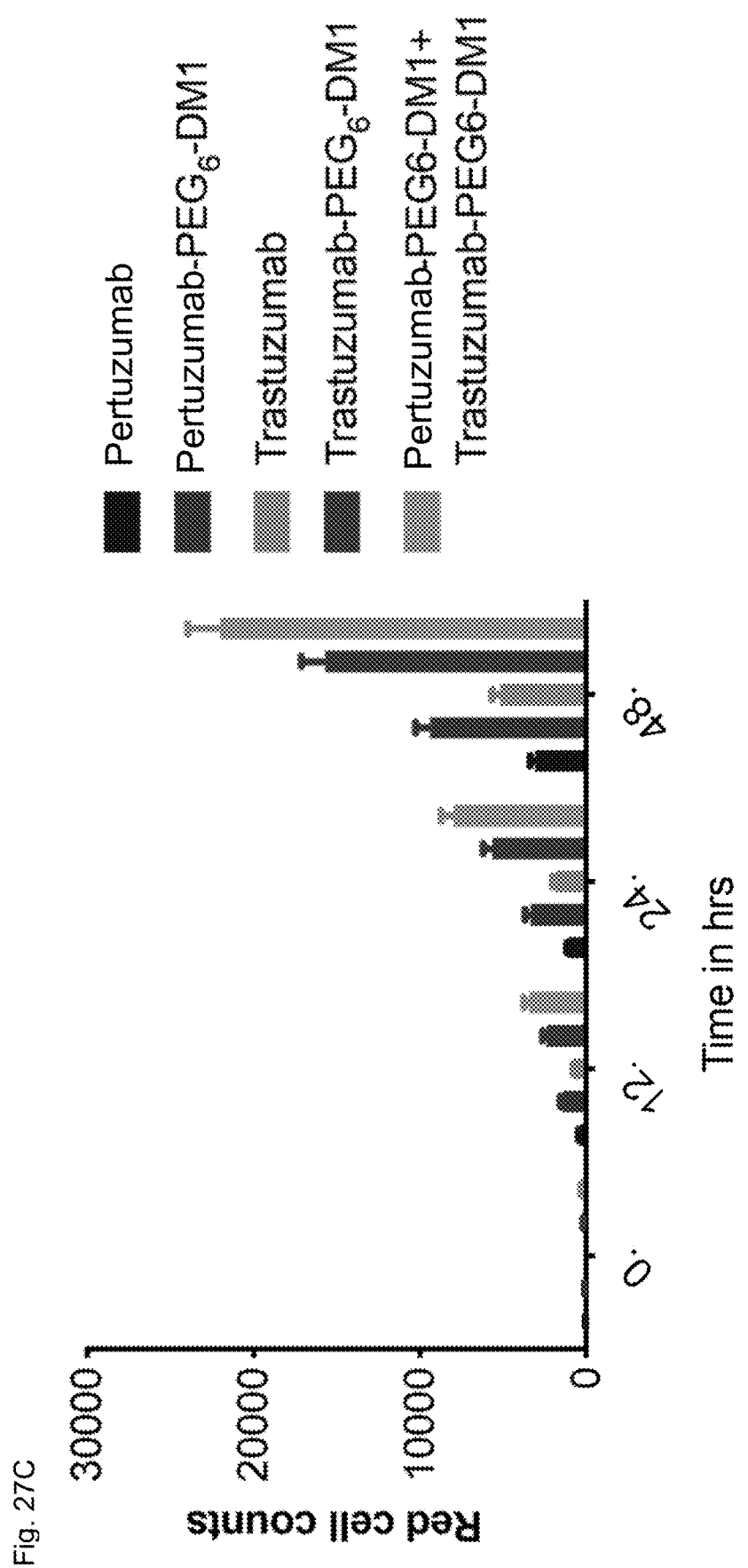
Figure 27D:
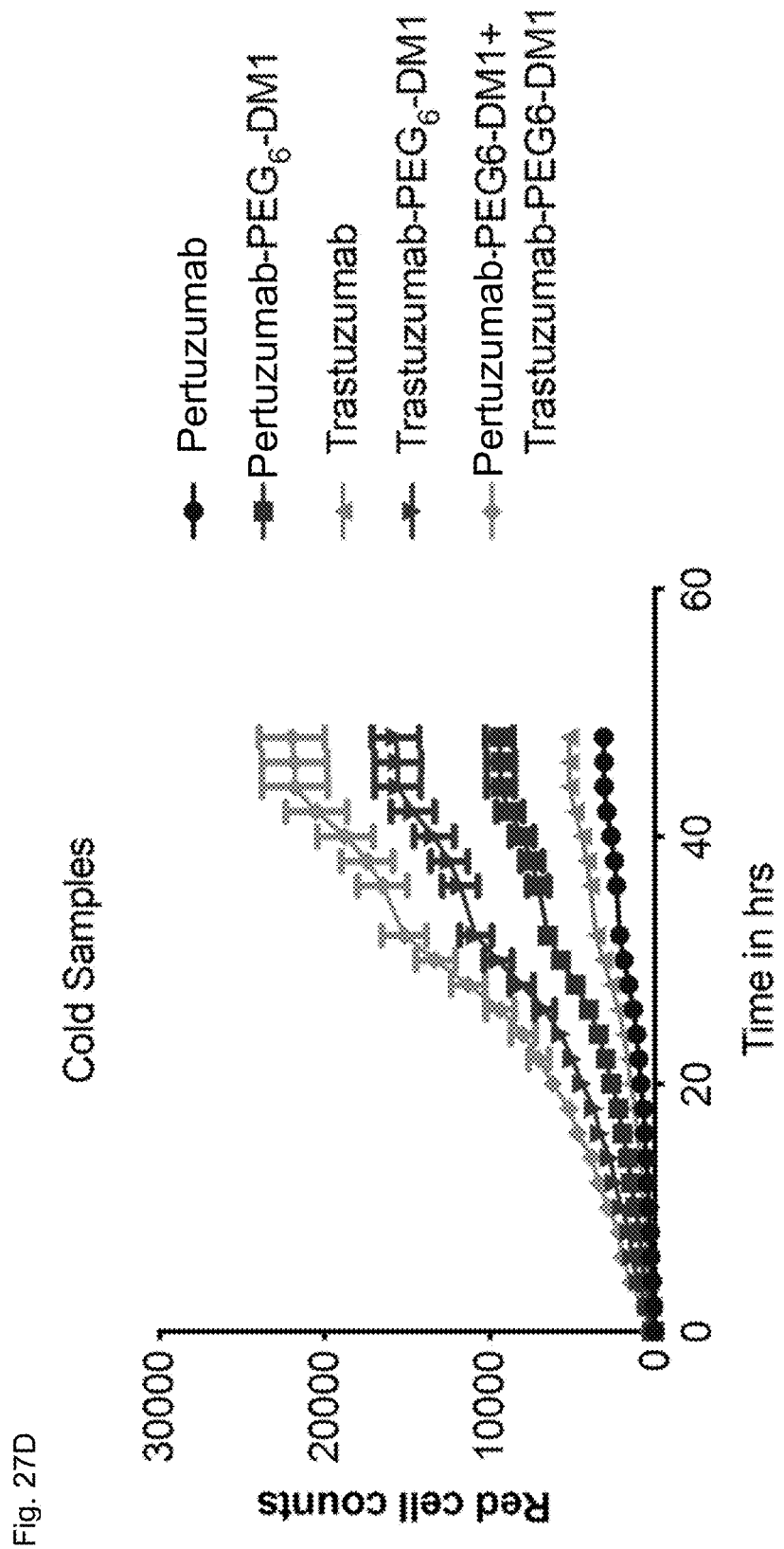
Figure 27E:
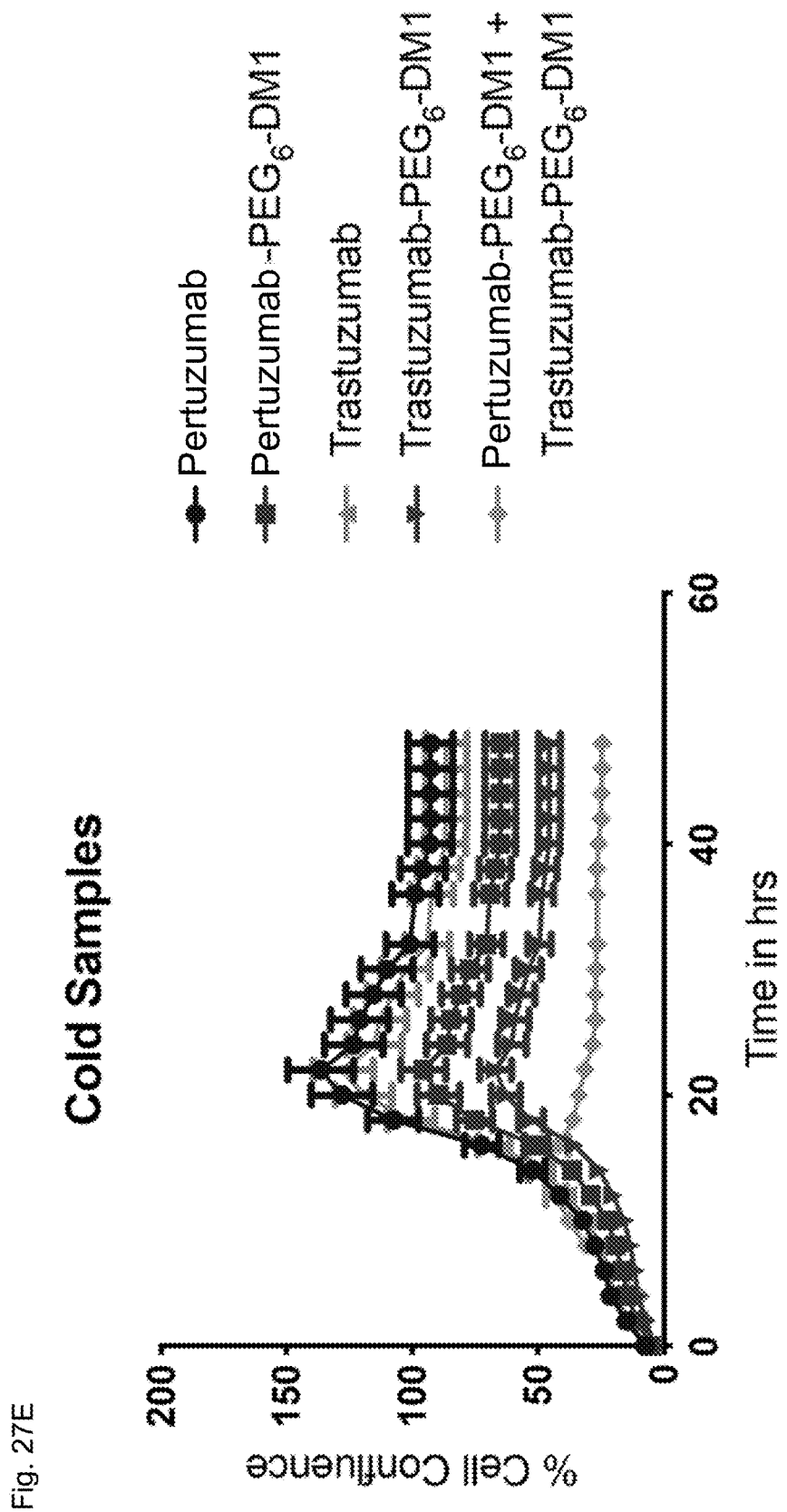

FIG. 26 (A, B) shows cytotoxin conjugated and/or radiolabelled pertuzumab and trastuzumab.

FIG. 27 (A-E) shows internalization of $^{225}$Ac-pertuzumab-PEG6-DM1 (domain II)+$^{225}$Ac-trastuzumab-PEG6-DM1 (domain IV) in HER2 expressing cells.

Figure 28A:
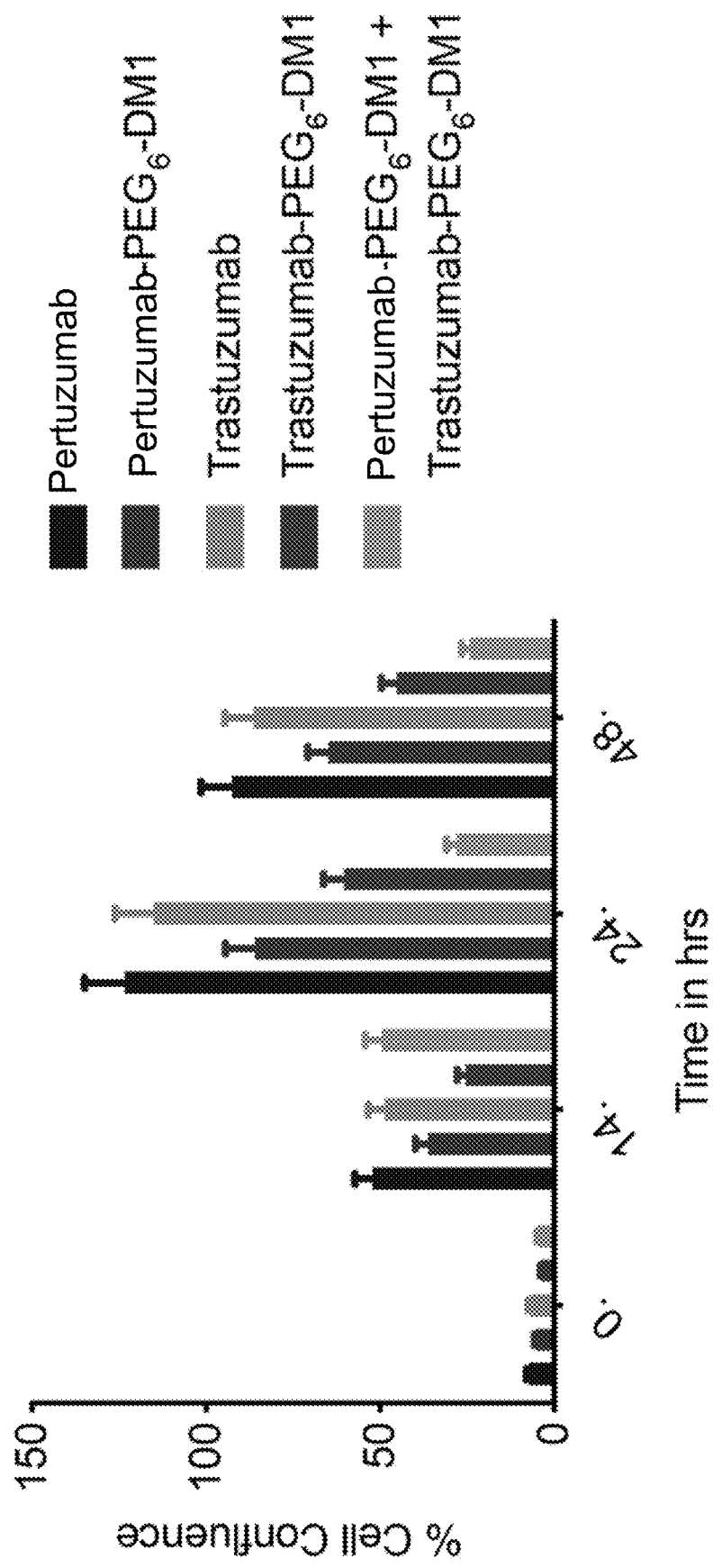
Figure 28B:
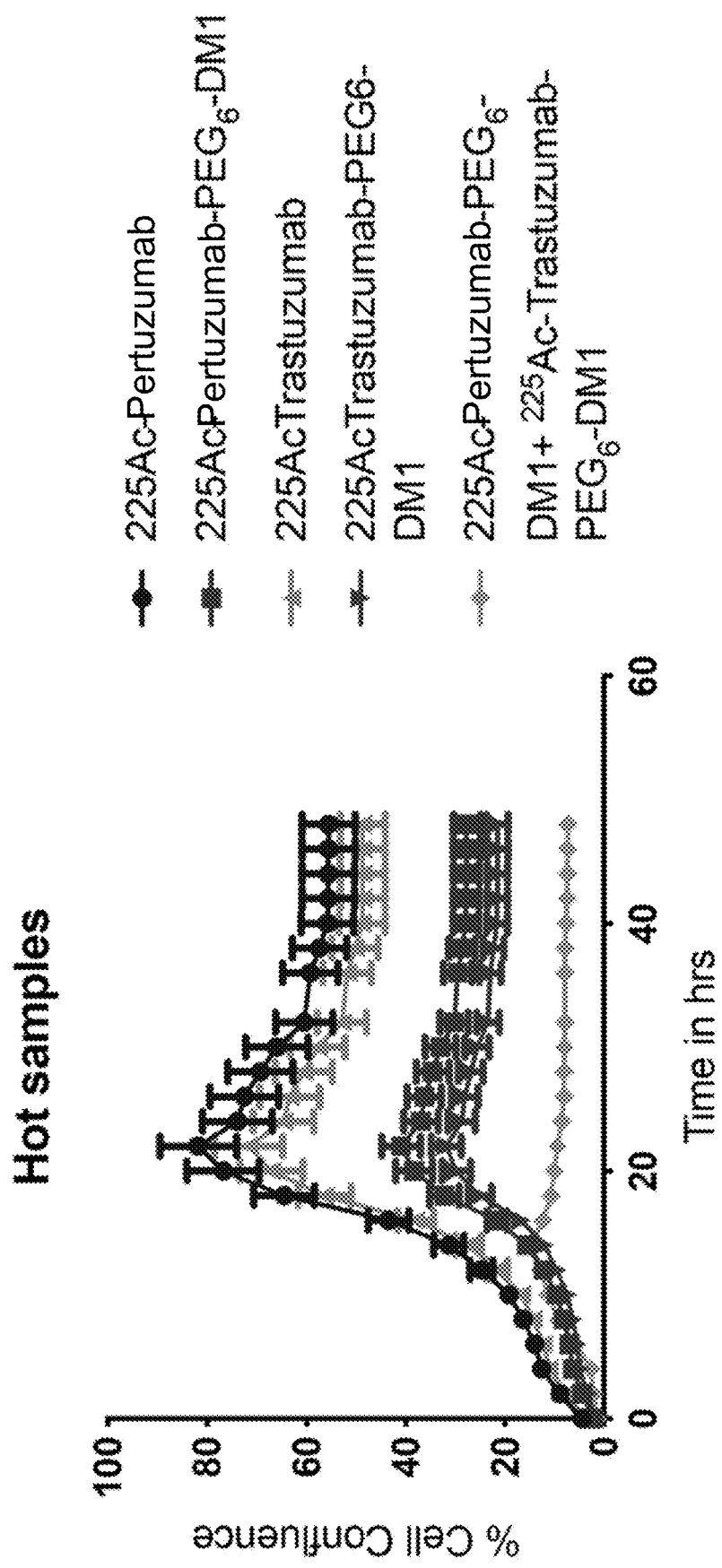
Figure 28C:
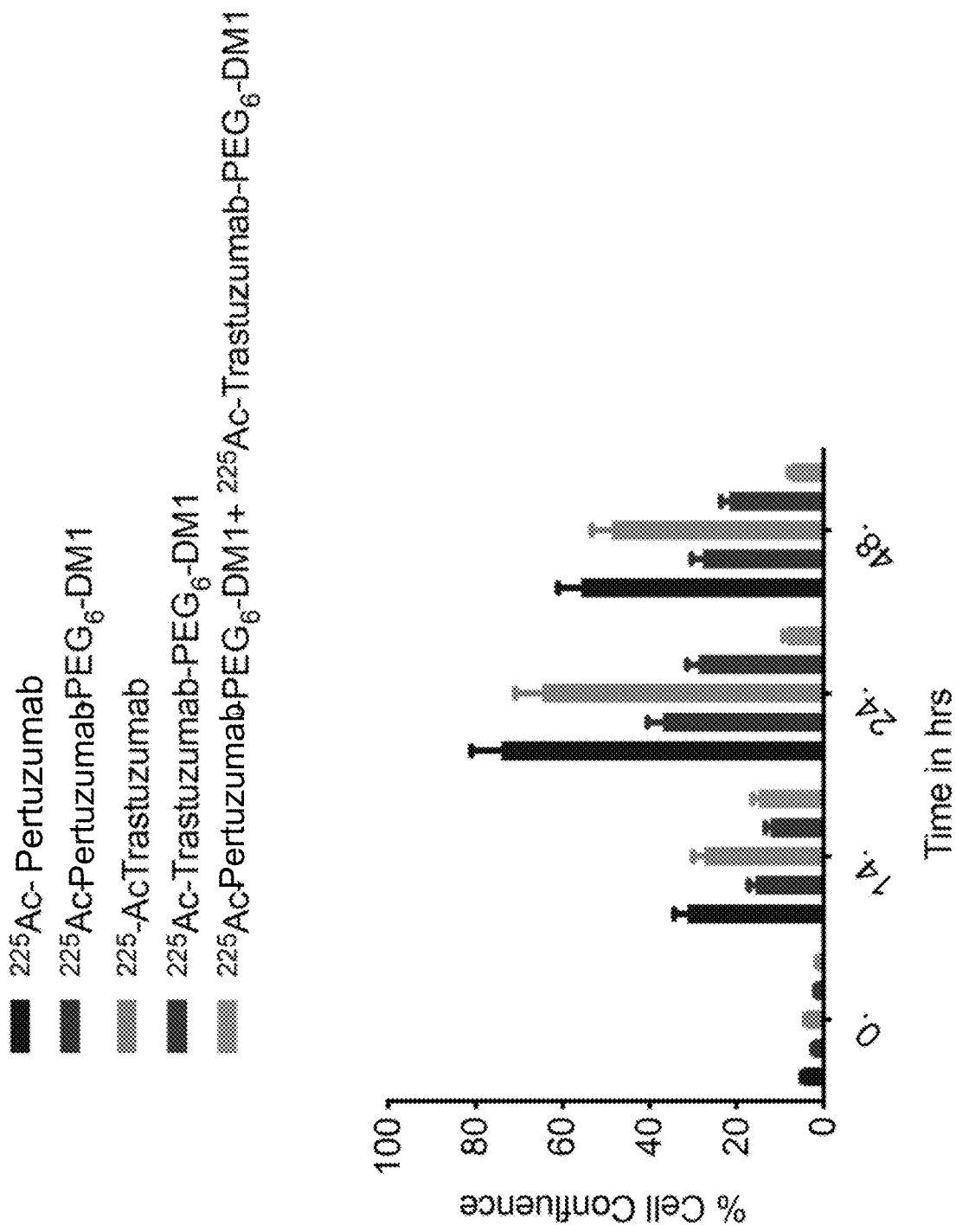
Figure 29A:
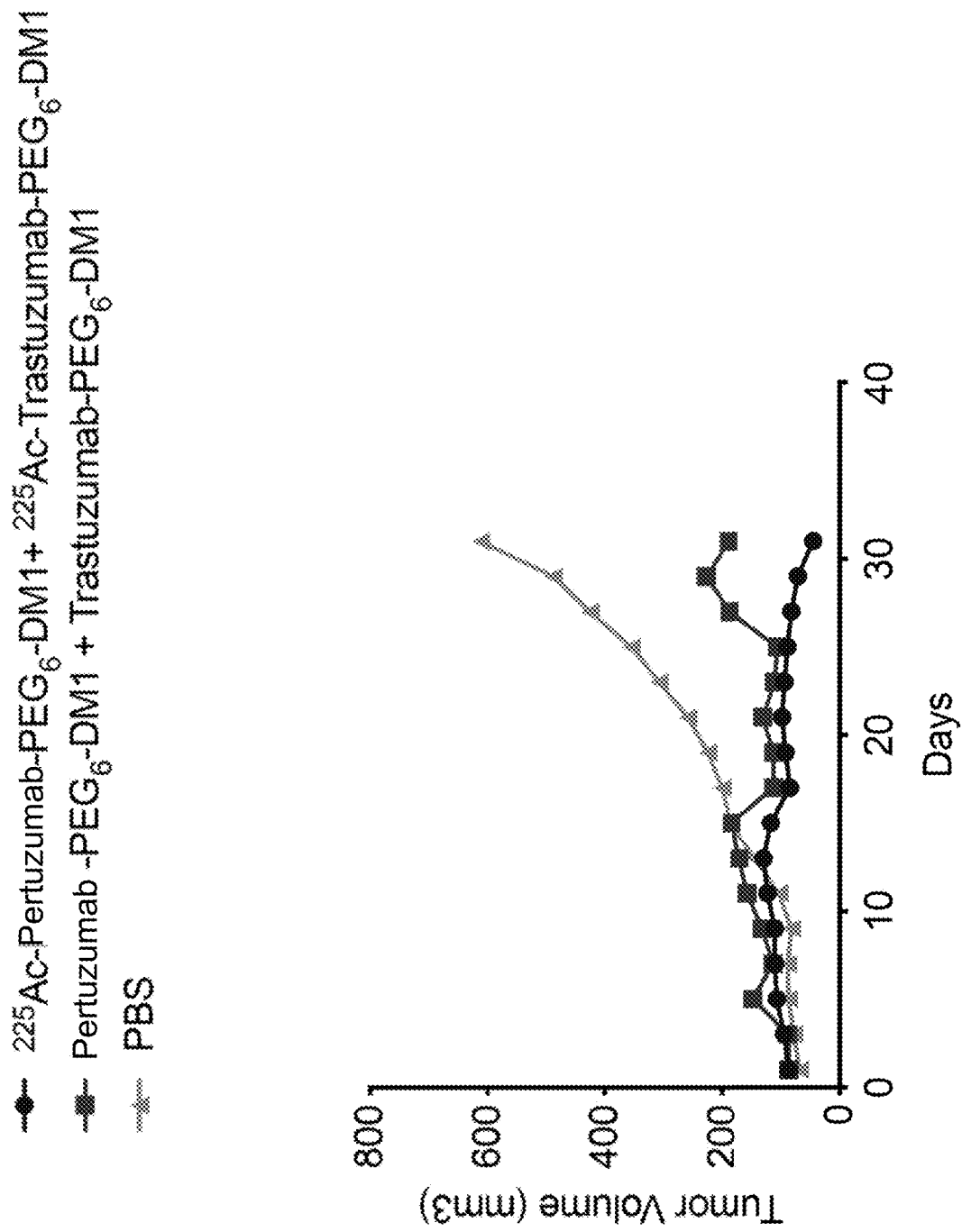
Figure 29B:
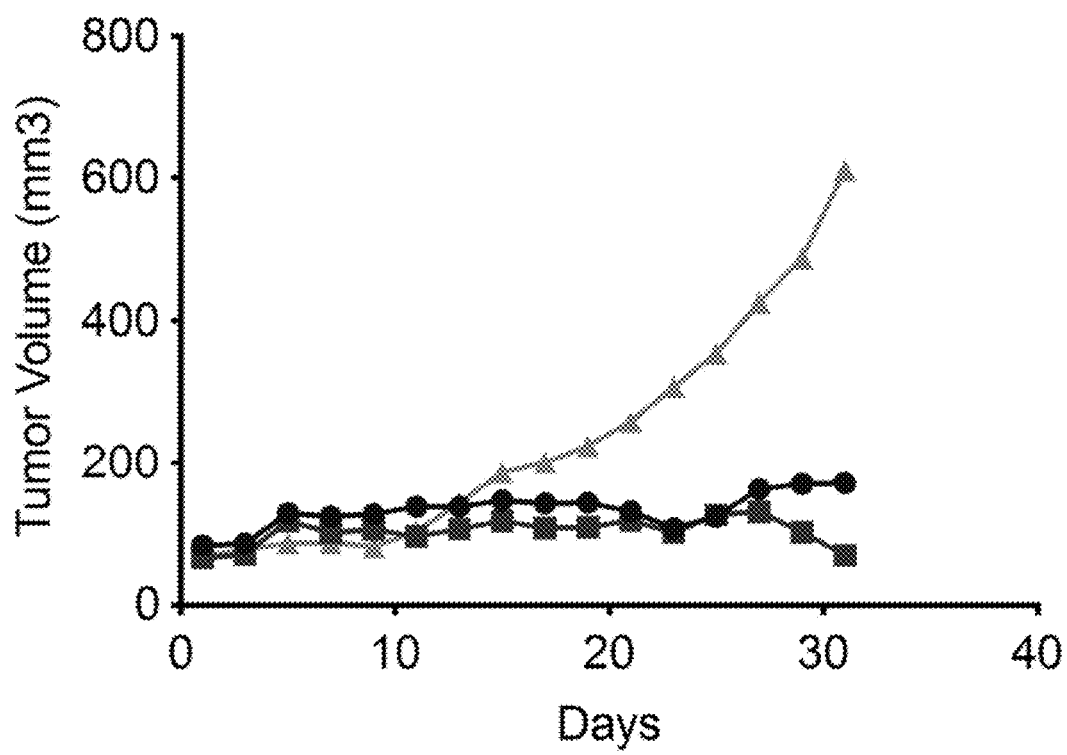
Figure 29C:
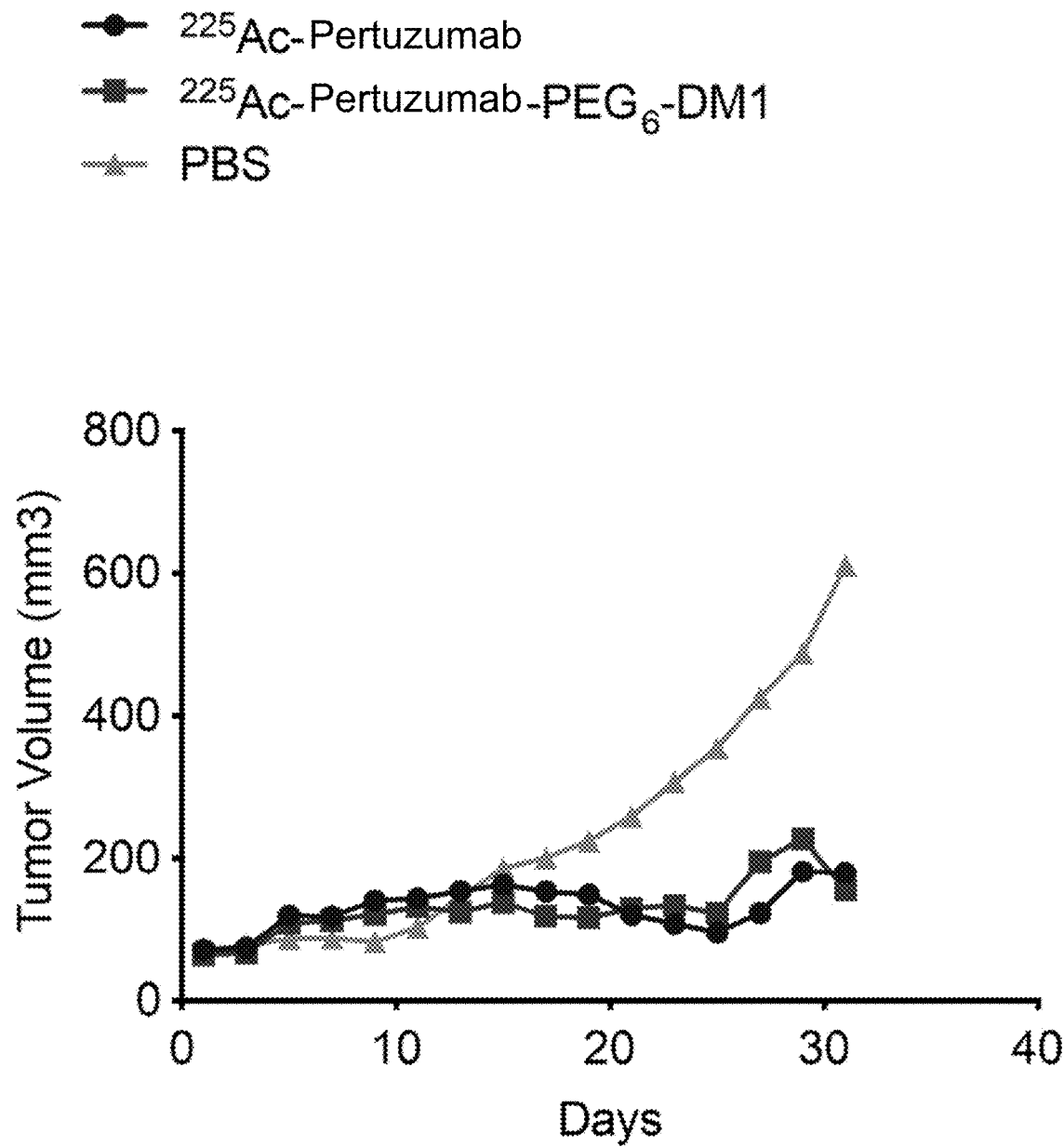
Figure 29D:
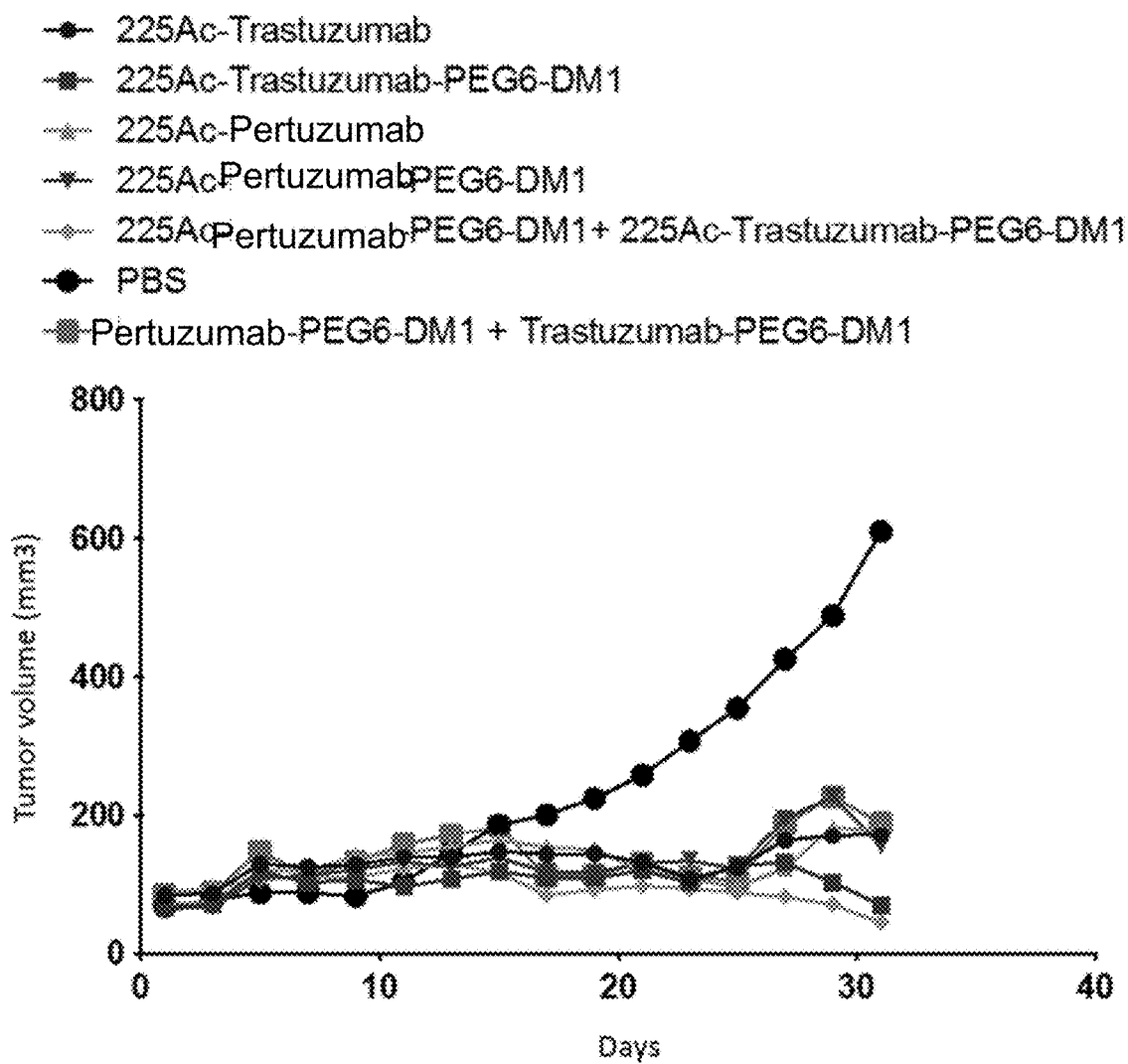

FIG. 28 (A-C) shows cytotoxicity of $^{225}$Ac-pertuzumab-PEG$_6$-DM1 (domain II)+$^{225}$Ac-trastuzumab-PEG$_6$-DM1 (domain IV) in HER2 expressing cells.

FIG. 29 (A-D) shows administration of $^{225}$Ac-pertuzumab-PEG$_6$-DM1 (domain II)+$^{225}$Ac-trastuzumab-PEG$_6$-DM1 (domain IV) to mice bearing a resistant HER2 positive xenograft (JIMT).

Figure 30:
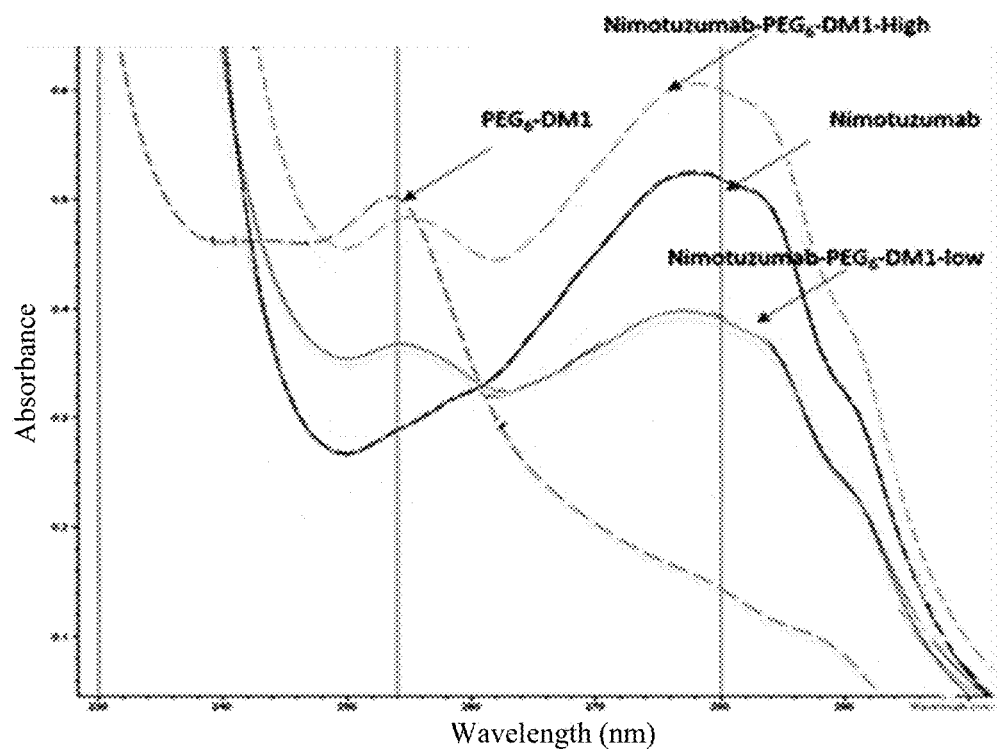

FIG. 30 shows a determination of Antibody-drug-ratio (UV method). Distinct UV spectra of drug, antibody and antibody drug conjugates are shown. Drug to antibody ratio was determined using UV method. Antibody and drug each have absorbance maxima at different wavelengths i.e. 280 and 254 nm respectively. Simultaneous equations were generated for both drug and antibody using the Beer-Lambert law. By solving the simultaneous equations, the number of drug per antibody was determined.

DESCRIPTION OF VARIOUS EMBODIMENTS

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. For example, the term "a cell" includes a single cell as well as a plurality or population of cells. Generally, nomenclatures utilized in connection with, and techniques of, cell and tissue culture, molecular biology, and protein and oligonucleotide or polynucleotide chemistry and hybridization described herein are those well-known and commonly used in the art (see, e.g. Green and Sambrook, 2012).

The term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Further, the definitions and embodiments described in particular sections are intended to be applicable to other embodiments herein described for which they are suitable as would be understood by a person skilled in the art. For example, in the following passages, different aspects of the disclosure are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Cytotoxic Agents

The inventors have developed novel cytotoxic agents comprising antibodies that bind cell surface receptors, where the antibodies are conjugated to a cytotoxin and/or radiolabeled. The inventors have shown that the cytotoxic agents have enhanced cellular internalization and/or cytotoxicity compared to corresponding antibodies that are not conjugated to a cytotoxin and/or radiolabelled. The inventors have also shown that the cytotoxic agents have increased potency towards cancer cells and display increased tumor suppression in tumor bearing mice compared to corresponding antibodies that are not conjugated to a cytotoxin and/or radiolabelled.

Accordingly, the present disclosure provides cytotoxic agents comprising an antibody that specifically binds a target cell surface receptor and a cytotoxin, wherein the cytotoxin is linked directly or indirectly to the antibody.

The present disclosure also provides cytotoxic agents comprising an antibody that specifically binds target cell surface receptor and a radiolabel, wherein the radiolabel is linked directly or indirectly to the antibody.

The disclosure further provides cytotoxic agents comprising an antibody that specifically binds a target cell surface receptor, a cytotoxin, and a radiolabel, wherein the cytotoxin is linked directly or indirectly to the antibody and wherein the radiolabel is linked directly or indirectly to the antibody.

As used herein, the term "target cell" refers to a cell that is desired to be targeted for inhibition or killing. Examples of target cells include cells associated with disease. In one embodiment, the target cell is a cancer cell.

"Cell surface receptor" refers to a molecule, typically a protein, found on the surface of a cell such as a target cell which can receive and transduce signals across the membrane of the cell. A "target cell surface receptor" is a cell surface receptor which is present on a target cell.

In one embodiment, the cell surface receptor is present on disease cells such as cancer cells.

In another embodiment, the cell surface receptor is associated with a disease (also referred to herein as a "disease cell surface receptor"). As used herein, a cell surface receptor "associated with a disease" refers to a cell surface receptor where the presence, functionality or expression level of the cell surface receptor on a target cell is associated for example in the occurrence, presence, severity or progression of the disease. In one embodiment, the disease is cancer.

Provided herein are antibodies that specifically bind a target cell surface receptor. As used herein, the expression "specifically binds" refers to the ability of an antibody to bind to a target (in this case, a target cell receptor) with greater affinity than it binds to a non-target.

As used herein, the term "antibody" refers to an antibody or any binding fragment thereof that contains at least a light chain and a heavy chain. "Antibody" includes synthetically produced antibodies and binding fragments.

The antibody may be from recombinant sources and/or produced in transgenic animals. The basic antibody structural unit is known to comprise a tetramer. Each tetramer is composed of two identical pairs of polypeptide chains, each pair having one light ("L") (about 25 kDa) and one heavy ("H") chain (about 50-70 kDa). The amino-terminal portion of each chain includes a variable region of about 100 to 110 or more amino acids primarily responsible for antigen recognition, and described in more detail below. The carboxy-terminal portion of each chain defines a constant region primarily responsible for effector function. The term "antigen-binding site" or "binding portion" refers to the part of the binding protein that participates in antigen binding. In an antibody, the antigen binding site is formed by amino acid residues of the N-terminal variable ("V") regions of the heavy and light chains. Three highly divergent stretches within the V regions of the heavy and light chains are also referred to as "hypervariable regions". In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs". Accordingly, the antibody in an embodiment comprises a heavy chain variable region or a heavy chain comprising a heavy chain complementarity determining region 1 (CDR-H1), heavy chain complementarity determining region 2 (CDR-H2) and heavy chain complementarity determining region 3 (CDR-H3), as well as a light chain variable region or light chain comprising a light chain complementarity determining region 1 (CDR-L1), light chain complementarity determining region 2 (CDR-L2) and light chain complementarity determining region 3 (CDR-L3). The CDRs are interposed between more conserved flanking stretches known as "framework regions", or "FRs". Thus, the term "FR" refers to amino acid sequences which are naturally found between, and adjacent to, hypervariable regions in immunoglobulins.

All CDRs and framework regions (FRs) disclosed herein, amino acid sequences of CDRs and FRs disclosed herein, and CDR-encoding or FR-encoding nucleic acid sequences disclosed herein, are intended to be defined in accordance with the Kabat numbering system (Kabat et al., 1991) unless otherwise indicated. For a definition of the Kabat number system also see http://www.bioinf.org.uk/abs/#cdrdef. Online tools such as http://opig.stats.ox.ac.uk/webapps/sabdab-sabpred/ANARCI.php can be used to determine Kabat numbering. Another system alternately employed in the art for such definitions is IMGT numbering (Lefranc et al., 2003).

As mentioned herein, the antibody is an antibody that specifically binds a cell surface receptor.

Examples of cell surface receptors contemplated herein include, but are not limited to, receptor tyrosine kinases such as the epidermal growth factor receptor (EGFR) family. Overexpression of receptors of the EGFR family have been shown to be associated with numerous cancers. The EGFR family includes EGFR (also known as ErbB-1 and HER1), ErbB-2 (also known as HER2), ErbB-3 (also known as HER3), and ErbB-4 (also known as HER4). In one embodiment, the cell surface receptor is EGFR, HER2, HER3 or HER4.

Accordingly, in one embodiment, the cell surface receptor is EGFR. The term EGFR as used herein refers to the ErbB1 or EGFR receptor tyrosine kinases and includes, without limitation, EGFR from any source such as those with sequences as shown in Genbank Accessions: AAI28420, AAI18666, AAH94761, incorporated herein by reference in their entirety. In one embodiment, EGFR is human EGFR. EGFR includes a number of different domains, including extracellular domains I-IV. These domains are known and can be readily identified by a person of skill in the art.

Accordingly, in one embodiment, the antibody specifically binds EGFR.

In another embodiment, the antibody specifically binds an epitope wholly or partly within domain I and/or domain II of EGFR and optionally does not bind an epitope wholly or partly within domain III of EGFR. As used herein, the term "epitope" refers to the specific site or specific combination of sites/amino acids on an antigen that are bound by an antibody for example an antibody described herein.

Examples of antibodies which specifically bind domain II of EGFR include those described in PCT/CA2018050202 (EGFR-BINDING AGENTS AND USES THEREOF, filed Feb. 22, 2018), the contents of which are incorporated herein by reference in their entirety. For example, the antibody is optionally DL06, DL06 AM Clone 10, DL06 AM Clone 23, DL06 AM Clone 24, DL06 SR02 (also referred to as 8708) and Fab H (also referred to as 8709), as described in PCT/CA2018050202. The light chain and heavy chain complementarity determining regions (CDRs) of the anti-EGFR antibodies described in PCT/CA2018050202 are set out in PCT/CA2018050202.

One antibody that specifically binds domain II of EGFR particularly provided herein is 8709-scFv-Fc. As described in PCT/CA2018050202, Fab 8709 comprises a light chain CDR1 comprising the amino acid sequence of QSVSSA (SEQ ID NO: 1), a light chain CDR2 comprising the amino acid sequence of SAS (SEQ ID NO: 2), and a light chain CDR3 comprising the amino acid sequence of QQSYWLIT (SEQ ID NO: 3) and a heavy chain CDR1 comprising the amino acid sequence of GFNLYSSS (SEQ ID NO: 4), a heavy chain CDR2 comprising the amino acid sequence of IYPYSGYTY (SEQ ID NO: 5), and a heavy chain CDR3 comprising the amino acid sequence of ARYPFGVSAYYAMDY (SEQ ID NO: 6). In another embodiment, Fab 8709 further comprises a methionine at residue 39 of the VH domain, a serine at residue 55 of the VH domain and a tyrosine at residue 66 of the VH domain.

The amino acid sequence of the heavy chain of Fab 8709 is:

(SEQ ID NO: 7)
EVQLVESGGGLVQPGGSLRLSCAASGFNLYSSSMHWVRQAPGKGLEWVA

SIYPYSGYTYYADSVKGRFTISADTSKNTAYLQMNSLRAEDTAVYYCAR

YPFGVSAYYAMDYWGQGTLVTVSSASTKGPSVFPLAPSSKSTSGGTAAL

GCLVKDYFPEPVTVSWNSGALTSGVHTFPAVLQSSGLYSLSSVVTVPSS

SLGTQTYICNVNHKPSNTKVDKKVEPKSCDKTHT.

The amino acid sequence of the light chain of Fab 8709 is:

(SEQ ID NO: 8)
DIQMTQSPSSLSASVGDRVTITCRASQSVSSAVAWYQQKPGKAPKLLIY

SASSLYSGVPSRFSGSRSGTDFTLTISSLQPEDFATYYCQQSYWLITFG

QGTKVEIKRTVAAPSVFIFPPSDSQLKSGTASVVCLLNNFYPREAKVQW

KVDNALQSGNSQESVTEQDSKDSTYSLSSTLTLSKADYEKHKVYACEVT

HQGLSSPVTKSFNRGECGGSDYKDDDDK.

8709-scFv-Fc is described in Bernhard et al., Theranostics 2019, Vol. 9, Issue 4. To produce 8709-scFv-Fc, the sequences from Fab 8709 (provided in PCT/CA2018/050202) were subcloned as an scFv-Fc antibody fragment using the method described in El-Sayed et al. Theranostics. 2018; 8(17): 4856-4869. The structure of an scFv-Fc fragment is depicted in FIG. 1 of El-Sayed et al. (2018).

Thus, in one embodiment, the antibody that specifically binds EGFR comprises a light chain CDR1 comprising the amino acid sequence of QSVSSA (SEQ ID NO: 1), a light chain CDR2 comprising the amino acid sequence of SAS (SEQ ID NO: 2), and a light chain CDR3 comprising the amino acid sequence of QQSYWLIT (SEQ ID NO: 3) and a heavy chain CDR1 comprising the amino acid sequence of GFNLYSSS (SEQ ID NO: 4), a heavy chain CDR2 comprising the amino acid sequence of IYPYSGYTY (SEQ ID NO: 5), and a heavy chain CDR3 comprising the amino acid sequence of ARYPFGVSAYYAMDY (SEQ ID NO: 6). In another embodiment, the antibody further comprises a methionine at residue 39 of the VH domain, a serine at residue 55 of the VH domain and a tyrosine at residue 66 of the VH domain.

In another embodiment, the antibody specifically binds an epitope wholly or partly within domain III of EGFR and optionally does not bind an epitope wholly or partly within domain I and/or domain II of EGFR. Examples of antibodies which specifically bind domain III of EGFR include nimotuzumab, necitumumab, cetuximab, matuzumab and panitumumab. Nimotuzumab (Theraloc, InnoMab PTE), necitumumab (Eli Lilly and Co.), cetuximab (Erbitux, Eli Lilly and Co.), matuzumab (EMD 72000, Merck Serono) and panitumumab (Vectibix, Amgen) are commercially available antibodies and their light chain and heavy chain complementarity determining regions (CDRs) are known.

In one embodiment, the antibody that specifically binds EGFR is a monoclonal antibody. In another embodiment, the antibody that specifically binds EGFR is an antibody that inhibits binding of ligand to EGFR.

Numerous additional antibodies which specifically bind EGFR are known in the art and/or are commercially available that can be used in preparing the cytotoxic agents described herein including, but not limited to, AMG595 (Amgen), Depatuxizumab/ABT 806 (AbbVie), duligotuzumab (Genentech; Roche), GC1118 (Green Cross Corporation), imgatuzumab/GA201) (Roche), zalutumumab (Genmab) and tomuzotuximab (Glycotope GmbH), futuximab (Creative Biolabs) and modotuximab (Creative Biolabs).

In another embodiment, the cell surface receptor is HER2 (also known as ErbB-2). The term HER2 as used herein refers to the ErbB-2 or HER2 receptor tyrosine kinases and includes, without limitation, HER2 from any source. Typically HER2 is human HER2. HER2 includes a number of different domains, including extracellular domains I-IV. These domains are known and can be readily identified by a person of skill in the art.

Thus, in one embodiment, the antibody specifically binds HER2. In one embodiment, the antibody specifically binds an epitope wholly or partly within domain IV of HER2. An example of such an antibody is the commercially available antibody trastuzumab (herceptin, Roche). In another embodiment, the antibody specifically binds an epitope wholly or partly within domain II of HER2. An example of such an antibody is the commercially available antibody pertuzumab (Perjeta, Roche). Numerous additional antibodies which specifically bind HER2 are known in the art and/or are commercially available that can be used in preparing the cytotoxic agents described herein including, but not limited to, margetuximab (MacroGenics), zanidatamab/ZW25 (Zymeworks), ertumaxomab (Creative Biolabs), Zenocutuzomab (Merus), GBR1302 (Glenmark Pharmaceuticals), H2Mab-139 (abcam) and hersintuzumab (Creative Biolabs).

In another embodiment, the cell surface receptor is HER3 (also known as ErbB-3). The term HER3 as used herein refers to the ErbB-3 or HER3 receptor tyrosine kinases and includes, without limitation, HER3 from any source. In one embodiment, HER3 is human HER3.

Thus, in another embodiment, the antibody specifically binds cell surface receptor HER3.

Examples of antibodies which bind HER3 include those described in PCT/CA2018050965 (HER3 BINDING AGENTS AND USES THEREOF, filed Aug. 9, 2018), the contents of which are incorporated herein by reference in their entirety. For example, the antibody is optionally HER3-3 or HER3-10 as described in PCT/CA2018050965. The light chain and heavy chain complementarity determining regions (CDRs) of HER3-3 and HER3-10 are set out in PCT/CA2018050965. Numerous additional antibodies which specifically bind HER3 are known in the art and/or are commercially available that can be used in preparing the cytotoxic agents described herein, including but not limited to, Patritumab (Daiichi Sankyo Company), Lumretuzumab (Roche), Duligotumab (Merck & Co.), Seribantumab (Sanofi/Merrimack Pharmaceuticals, Inc.), elgemtumab (Novartis Oncology), AV-203 (Aveo Oncology), KTN3379/CDX-3379 (Kolltan Pharmaceuticals), GSK2849330 (GlaxoSmithKline), zenocutuzomab (Merus) and Istiratumab (Merrimack Pharmaceutical).

In another embodiment, the surface receptor is HER4. The term HER4 refers to HER4 from any source and in one embodiment, HER4 is human HER4.

Thus, in one embodiment, the antibody specifically binds HER4. Antibodies which specifically bind HER4 are known in the art and/or are commercially available, including but not limited to, H4.77.16/Ab77 (Invitrogen), HFR1 (Invitrogen) and MA1-861 (ThermoFisher). Such antibodies can be used in preparing the cytotoxic agents described herein.

In another embodiment, the cell surface receptor is EPH receptor A2 (also ephrin type-A receptor 2; EphA2). The term EphA2 refers to EphA2 from any source and in one embodiment, EphA2 is human EphA2.

Thus, in one embodiment, the antibody specifically binds EPH receptor A2 (ephrin type-A receptor 2). Antibodies which specifically bind EphA2 are known in the art and/or are commercially available, including but not limited to, MEDI 547 (Creative Biolabs), PABL-083 (Creative Biolabs) and DS-8895a (Daiichi Sankyo Company). Such antibodies can be used in preparing the cytotoxic agents described herein.

In another embodiment, the cell surface receptor is insulin-like growth factor 1 (IGF-1R) receptor. The term IGF-1R refers to IGF-1R from any source and in one embodiment, IGF-1R is human IGF-1R. Thus, in one embodiment, the antibody specifically binds insulin-like growth factor 1 (IGF-1) receptor (IGF-1R). Antibodies which specifically bind IGF-1R are known in the art and/or are commercially available, including but not limited to, cixutumumab (Creative Biolabs). Others include figitumumab (Pfizer), ganitumab (Amgen), Istiratumab (Merrimack Pharmaceuticals), teprotumumab (Horizon), xentuzumab (Boehringer Ingelheim), dalotuzumab (Merck), robatumumab (Merck) and BIIB022 (Biogen). Such antibodies can be used in preparing the cytotoxic agents described herein. Other antibodies that specifically bind cell surface receptors that can be used include for example Rituximab (Biogen Idec/Genentech), Ibritumomab (Spectrum Pharmaceuticals), Tositumomab (GSK), Brentuximab (Seattle Genetics/Millennium), Alemtuzumab (Bayer/Sanofi), Adecatumumab (Amgen; Merck Serono), Labetuzumab (Gilead), Pemtumomab (Creative Biolabs), Oregovomab (Quest PharmaTech Inc.), minretumomab (Creative Biolabs), Farletuzumab (Eisai Inc), Bevacizumab (Roche), Etaracizumab (Medlmmune), Volociximab (PDL BioPharma and Biogen Idec), Mapatumumab/HGS-ETR1 (GlaxoSmithKline), Lexatumumab/HGS-ETR2 (GlaxoSmithKline), Sibrotuzumab (Boehringer Ingelheim), Edrecolomab (Creative Biolabs), Smart M195 (Protein Design Labs), Smart ID10 (Protein Design Labs), Oncolym/Lym-1 (Peregrine Pharmaceuticals), AlloMune/siplizumab (BioTransplant), Glembatumumab (Celldex Therapeutics), Epratuzamab (Immunomedics), daratumumab (Janssen), Elotuzumab (Bristol-Myers Squibb and AbbVie), Blinatumomab (Amgen), Catumaxomab (Linton Pharm; Neovii Biotech; Swedish Orphan Biovitrum; TRION Pharma), Ifabotuzumab (KaloBios), PF-06647263 (Pfizer), Obinutuzumab (Genentech) and altumomab (Creative Biolabs). Such antibodies can be used in preparing the cytotoxic agents described herein. In one embodiment, the antibody is a fragment antigen-binding (Fab), single-chain Fv (scFv), single-chain Fab (scFab), Fab', Fv, chemically linked $F(ab')_2$, dsFv, dsFv', $sc(Fv)_2$, ds-scFv, (dsFv)2, scFv-Fc, scFV-$C_H$3, single-chain immunoglobulin (e.g. scIgG), single-domain antibody (sdAb, nanobody), scFv-Fc, minibody (scFv-CH3), diabody, tribody, tetrabody, multimeric antibody (e.g. scFv dimer, bivalent diabody), multispecific antibody (e.g. bispecific antibody, trispecific antibody, di-scFv, tri-scFv, bispecific $Fab_2$, trispecific $Fab_2$, trispecific triabody, trispecific $Fab_3$), multimeric/multispecific antibody (e.g. scFv dimer, bispecific diabody, dsFv-dsFv'), heavy-chain antibody, $Fab_3$, divalent VHH, pentavalent VHH (pentabody), $(scFv-SA)_4$ or $[sc(Fv)2]_2$.

The antibody is optionally a bispecific antibody (also referred to herein as a "bifunctional antibody"). In one embodiment, the bispecific antibody specifically binds EPH receptor A2 and a second disease cell surface receptor. The second disease cell surface receptor can be, for example, a member of the epidermal growth factor receptor family, optionally EGFR, HER2, HER3 or HER4, or the cell surface receptor IGF-1R. The bispecific anti-EphA2 antibody described herein which specific binds both EphA2 and EGFR is such an antibody.

In another embodiment, the antibody is a scFv-Fc. An example of an scFv-Fc is 8709-scFv-Fc. A description of how to make an scFv-Fc can be found, for example, in Bujak et al., Reformatting of scFv antibodies into the scFv-Fc format and their downstream purification. *Methods Mol Biol.* 2014; 1131:315-34.

Fab, Fab' and F(ab')2, scFv, dsFv, ds-scFv, scFv-$C_H$3, scFv-Fc, IgG, dimers, minibodies, diabodies, bispecific antibody fragments and other fragments can be synthesized by recombinant techniques.

Antibodies can also be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments.

In one embodiment, the antibody is an antibody, such as a human antibody, containing engineered variable regions (e.g. containing variable regions selected from a phage display library displaying engineered antibody variable regions, e.g. a phage-Fab library or a phage-scFv library), or a chimeric antibody comprising human constant regions and an antibody variable region of a non-human mammal. The antibody may be a humanized antibody, e.g. an antibody comprising human constant regions, human variable region framework regions, and HER3-binding CDRs generated in a non-human mammal. The non-human mammal may be a rodent, such as a mouse, rat, rabbit, guinea pig or hamster. Alternately, the non-human mammal may be an ungulate, such as a camelid or a bovid.

In another embodiment, the antibody is a human antibody, such as an IgG1 antibody, wherein the heavy chain constant regions are gamma1 heavy chain constant regions. In other embodiments, the antibody is a human antibody, such as an IgA1, IgA2, IgD, IgG2, IgG3, IgG4, IgE or IgM antibody, wherein the heavy chain constant regions are alpha1, alpha2, delta, gamma2, gamma3, gamma4, epsilon or mu heavy chain constant regions, respectively.

In a further embodiment, the antibody is a monoclonal antibody. As used herein, a "monoclonal" antibody of the disclosure refers to a population of identical antibodies, for example a population of antibodies where the CDRs are identical in all the molecules of the population. Various procedures known within the art may be used for the production of monoclonal antibodies (see, for example, Greenfield, 2013). Monoclonal antibodies are commonly alternatively referred to using the abbreviations "mAb" or "MAb".

Typically, the antibody is a therapeutic antibody.

The antibody is optionally an isolated antibody. The term "isolated antibody" or "isolated and purified antibody" refers to an antibody that is substantially free of cellular material or culture medium when produced by recombinant DNA techniques, or chemical precursors, or other chemicals when chemically synthesized and/or other antibodies, for example directed to a different epitope.

It can be desirable to modify an antibody disclosed herein with respect to effector function, so as to enhance its effectiveness in binding a cell surface receptor. For example, where the antibody comprises an antibody Fc region, such as an antibody, cysteine residue(s) can be introduced into the COOH terminal of the Fc region, thereby allowing interchain disulfide bond formation between antibody monomers in this region.

Functional variants of the antibodies described herein are also encompassed by the present disclosure. The term "functional variant" as used herein includes one or more amino acid and/or nucleotide modifications in a sequence (polypeptide or nucleic acid respectively) for example, one or more modifications of a light chain or a heavy chain complementarity determining region (CDR) disclosed herein that perform substantially the same function as the light chain and heavy chain CDRs disclosed herein in substantially the same way. In one embodiment, variants of CDRs disclosed herein include, without limitation, conservative amino acid substitutions. Variants of the CDRs also include additions and deletions to the CDR sequences disclosed herein. In addition, variant nucleotide sequences and polypeptide sequences include analogs and derivatives thereof.

A "conservative amino acid substitution" as used herein, is one in which one amino acid residue is replaced with another amino acid residue without abolishing the protein's desired properties. Suitable conservative amino acid substitutions can be made by substituting amino acids with similar hydrophobicity, polarity, and R-chain length for one another. Examples of conservative amino acid substitutions include:

| Conservative Substitutions | |
|---|---|
| Type of Amino Acid | Substitutable Amino Acids |
| Hydrophilic | Ala, Pro, Gly, Glu, Asp, Gln, Asn, Ser, Thr |
| Sulphydryl | Cys |
| Aliphatic | Val, Ile, Leu, Met |
| Basic | Lys, Arg, His |
| Aromatic | Phe, Tyr, Trp |

Thus, in one embodiment, the present disclosure includes functional variants to the amino acid sequences disclosed herein.

In particular, the disclosure provides functional variants of the CDR sequences disclosed herein. In one embodiment, functional variants of the CDR sequences of the light and heavy chains disclosed herein have at least 90%, 95% or 99% sequence identity with the CDR sequences disclosed herein. In another embodiment, functional variants of the CDR sequences disclosed herein comprise at least 1, 2, 3 or 4 amino acid substitutions, optionally conservative substitutions, in the CDR sequences disclosed herein.

The term "sequence identity" as used herein refers to the percentage of sequence identity (also referred to herein as "percent identity") between two amino acid sequences or two nucleic acid sequences. To determine the percent identity of two amino acid sequences or of two nucleic acid sequences, the sequences are aligned for optimal comparison purposes (e.g. gaps can be introduced in the sequence of a first amino acid or nucleic acid sequence for optimal alignment with a second amino acid or nucleic acid sequence). For antibodies, percentage sequence identities can be determined when antibody sequences maximally aligned by IMGT or Kabat or other numbering convention. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. One non-limiting example of a mathematical algorithm utilized for the comparison of two sequences is the algorithm of Karlin and Altschul, 1990, modified as in Karlin and Altschul, 1993. Such an algorithm is incorporated into the NBLAST and XBLAST programs of Altschul et al., 1990. BLAST nucleotide searches can be performed with the NBLAST nucleotide program parameters set, e.g. for score=100, wordlength=12 to obtain nucleotide sequences homologous to a nucleic acid molecules of the present disclosure. BLAST protein searches can be performed with the XBLAST program parameters set, e.g. to score-50, wordlength=3 to obtain amino acid sequences homologous to a protein molecule of the present invention. To obtain gapped alignments for comparison purposes, Gapped BLAST can be utilized as described in Altschul et al., 1997. Alternatively, PSI-BLAST can be used to perform an iterated search which detects distant relationships between molecules. When utilizing BLAST, Gapped BLAST, and PSI-Blast programs, the default parameters of the respective programs (e.g. of XBLAST and NBLAST) can be used (see, e.g. the NCBI website). Another non-limiting example of a mathematical algorithm utilized for the comparison of sequences is the algorithm of Myers and Miller, 1988. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

The terms "immunoconjugate" and "cytotoxic agent" as described herein refer to an antibody that is coupled to a cytotoxin, a radionuclide or both.

The cytotoxic agents described herein can include a cytotoxin, which is linked directly or indirectly to the antibody.

As used herein, the term "cytotoxin" refers to a substance that is cytotoxic to (e.g. kills) a target cell. A variety of cytotoxins are known.

The cytotoxin may be, for example, an enzymatically active toxin of bacterial, fungal, plant, or animal origin, or a fragment thereof.

In one embodiment, the cytotoxin is a microtubule disruptor such as maytansine or derivatives thereof (also referred to as maytansinoids). Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and maytansinol analogues have been reported. See U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, and Kawai et al (1984) Chem. Pharm. Bull. 3441-3451), each of which are expressly incorporated by reference.

In one particular embodiment, the cytotoxin is N(2')-deacetyl-N(2')-(3-mercapto-1-oxopropyl)-maytansine (DM1) or N(2')-deacetyl-N2-(4-mercapto-4-methyl-1-oxopentyl)-maytansine (DM4).

Other examples of cytotoxins include, but are not limited to auristatins calicheamicins, duocarmycins, doxorubicin derivatives, anthracyclines, amanitins and camptothecins.

In some embodiments, the cytotoxin is selected from diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes.

In another embodiment, the cytotoxin is a microtubule destabilizer, a dolastatin, a tubulysin, a cryptophycins, a methionine aminopeptidase, a calicheamicin, an inhibitor of nuclear export of proteins CRM1, a DPPIV inhibitor, a proteasome inhibitor, an inhibitor of phosphoryl transfer reactions, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder, a DHFR inhibitor, a pro-apoptotic agent, a Bcl2 inhibitor, an MCL1 inhibitor, a HSP90 inhibitor, an IAP inhibitor or an mTor inhibitor.

In another embodiment, the cytotoxin is a radiosensitizer. As used herein, the term "radiosensitizer" refers to an agent that makes cells more sensitive to radiation. Examples of radiosensitizers include but are not limited to taxanes, gemcitabine, capecitabine, nicotinamide, misonidazole, curcumin and tirapazamine.

The cytotoxin is linked directly or indirectly to the antibody.

For example, the cytotoxin may be linked to the antibody by any chemical reaction that will bind the cytotoxin and the antibody thereof, so long as these retain their respective activities/characteristics for the intended use thereof. This linkage can include chemical mechanisms including for instance covalent binding, affinity binding, intercalation, coordinate binding and complexation.

In one embodiment, the cytotoxin is linked to the antibody via a linker, also referred to here as a "cytotoxin linker". The term "linker" as used herein means a chemical moiety comprising or derived from a group of atoms that is covalently attached to an antibody, and that is also covalently attached to a cytotoxin.

Examples of linkers useful for linking cytotoxins to antibodies or fragment thereof include N-succinimidul-4-(20pyridyldithio) butanoate (SPDB) and succinmidyl 4-(N-maleimidomethyl) cyclohexane-1-carboxylate (SMCC).

In one embodiment, the linker comprises PEG (polyethylene glycol). For example, one linker comprising PEG is a poly-ethylene glycol (PEGS) linker with malemide and N-hydroxysuccinamide (NHS) functional groups (Mal-PEG$_6$-NHS). PEGs of different chain lengths can also be used.

Other linkers that can be used include renal brush boarder cleavable linker Gly-L-Phe-L-Lys (GFK), the L-form and Gly-L-Tyr-L-Lys (GYK)". Also cathepsin/lysosomal cleavable linkers such as "MC-Phe-Lys-PABC; MC-Val-Lys-PABC; MC-Ala-Lys-PABC; MC-Val-Cit-PABC; MC-Phe-Cit-PABC; MC-Leu-Cit-PABC; MC-Ile-Cit-PABC, where PABC is p-aminobenzyloxycarbonyl and MC is maleimidocaproyl. Linkers also include compounds comprising or derived from divalent radicals such as an alkylene, an arylene, a heteroarylene, moieties such as: —(CR2)nO(CR2)n- wherein R2 is independently repeating units of alkyloxy (e.g. polyethylenoxy, PEG, polymethyleneoxy) and alkylamino (e.g. polyethyleneamino, polyetheramines such as Jeffamine™) and n is independently in particular n may be 1 to 15; N-succinimidyl 4-(maleimidomethyl)cyclohexanecarboxylate (SMCC) and N-succinimidyl 4-(2-pyridyldithio)butanoate (SPDB); and diacid ester and amides including succinate, succinamide, diglycolate, malonate, and caproamide as well as peptides, such as but not limited to repeating units of G, A and C (for example up to 10) with one or more lys residues or other suitable chemical groups for linking to a targeting agent and a cytotoxic moiety. The linker is optionally C1-30 alkylene, unsubstituted or substituted with one or more substituents, and/or optionally interrupted with one or more heteromoieties independently selected from O, S, NR1, and/or optionally interrupted with one or more of C(O) and C(S), wherein R1 is independently selected from H, and C1-6 alkyl. The linker can comprise a non-cleavable (stable linker) or cleavable unit (labile linker) such as a peptide bond or a disulfide bond. The linker can be conjugated to the antibody thereof and/or the cytotoxin via reactive functional groups.

In one embodiment, the linker is cleavable in the lysozyme.

A "DAR" (Drug to Antibody ratio) is often used to describe the ratio of drug to antibody in an antibody drug conjugate. In one embodiment, the ratio of cytotoxins to antibody molecules in a cytotoxic agent as described herein is 2-30 or 2-20, 2-15, 2-10 or 2-8 cytotoxins per antibody molecule, optionally 3-4 cytotoxins per antibody molecule. Methods of determining drug to antibody ratios are known in the art and can include UV spectroscopy.

The cytotoxic agents described herein can include a radiolabel.

As used herein, the term "radiolabel" refers to a moiety comprising a radionuclide and optionally a scaffold, wherein the scaffold is directly or indirectly coupled to the antibody.

A scaffold is required for conjugation to the antibody for some radionuclides. For example, where the radionuclide is $^{211}$At or $^{131}$I, the radionuclide may be directly coupled to the antibody.

A radionuclide may be coupled directly to an antibody for example by the method described Solomon et al., Cancers (Basel). 2020 Nov. 20; 12(11):3449 or by directly radiolabelling tyrosine residues on the antibody with isotopes such as $^{211}$At or $^{131}$I.

Where the radionuclide is $^{225}$Ac, the radionuclide will be present in a scaffold such that the radionuclide is indirectly coupled to the antibody.

The scaffold can comprise a chelator which chelates the radionuclide and has a moiety that is or can be coupled to an antibody. For example, the term "derived from a chelator or derived from a bifunctional chelator" refers to a chelator that prior to coupling is bifunctional and which been coupled to an antibody.

Chelators for radionuclides are known in the art. The chelator is typically a bifunctional chelator. As used herein, the term "bifunctional chelator" refers to a chelator that has a metal binding function as well as a chemically reactive functional group that provides the requisite chemistry for coupling to the antibody.

In another embodiment, the chelator is isothiocyanato-benzyl-3-methyldiethylene triaminepentaacetic acid (NCS-DTPA) (see, e.g. WO94/11026), isothiocyanatobenzyl-1,4,7,10-Tetraazacyclododecane-1,4,7,10-tetra(methylene phosphonic acid) (p-NCS-DOTP) and Macropa-NCS (6-((16-(((6-carboxypyridin-2-yl)methyl)-1,4,10,13-tetraoxa-7,16-diazacyclooctadecan-7-yl)methyl)-4-isothiocyanatopicolinic acid).

The chelator can also be DOTA (1,4,7,10-Tetraazacyclododecane-1,4,7,10-tetraacetic acid; tetraxetan), and derivatives thereof such as p-SCN-Bn-DOTA and Meo-DOTA-NCS or DOTP (1,4,7,10-Tetraazacyclododecane-1,4,7,10-tetra(methylene phosphonic) acid).

Other examples of chelators that can be used include 1,4,7,10-Tetraazacyclododecane-1,4,7-tris(acetic acid)-10-(2-thioethyl)acetamide (DO3A), [(R)-2-Amino-3-(4-isothiocyanatophenyl)propyl]-trans-(S,S)-cyclohexane-1,2-diamine-pentaacetic acid (CHX-DTPA), 2-S-(4-Isothiocyanatobenzyl)-1,4,7-triazacyclononane-1,4,7-triacetic acid (SCN-NOTA), 1,4,7-Triazacyclononane-1,4-bis-acetic acid-7-maleimidoethylacetamide (maleimide-NOTA), 4,11-bis(carboxymethyl)-1,4,8,11-tetraazabicyclo [6.6.2]hexadecane) (CB-TE2A) and Triethylenetetramine (TETA) derivatives.

The scaffold may be directly or indirectly coupled to the antibody. For example, the scaffold may be coupled to the antibody by any chemical reaction that will bind the scaffold and the antibody, so long as these retain their respective activities/characteristics for the intended use thereof. This coupling can include chemical mechanisms including for instance covalent binding, affinity binding, intercalation, coordinate binding and complexation. In one embodiment, the scaffold is attached to the antibody by an isopeptide linkage with an amino group of the antibody.

In one embodiment, each scaffold carries one radionuclide. Optionally, each antibody is coupled to 1-3 scaffolds, for an antibody: radionuclide ratio of 1:1 to 1:3. The number of scaffolds per antibody may be controlled for example by adjusting the pH of the reaction, the reaction time and the # of fold excess of the chelator to antibody.

The radionuclide is optionally an alpha emitter (a radionuclide that emits alpha particles) or a beta emitter (a radionuclide that emits beta particles).

In one embodiment, the radionuclide is a gamma emitter (a radionuclide that emits gamma particles). A cytotoxic agent comprising a gamma emitter can be used, for example, for imaging purposes. For example, a cytotoxic agent as described herein may be labelled with a gamma emitter at a low dose (for example a 1/100 dose) for imaging purposes. For example, it may be desirable to administer an antibody comprising both a cytotoxin and a radionuclide useful for imaging to patient for imaging purposes prior to administering the same antibody comprising the cytotoxin and a radionuclide useful for therapeutic purposes to the patient.

In one embodiment, the radionuclide is an alpha-particle emitter, optionally $^{225}$Ac.

Where the radiolabel comprises an alpha emitter radionuclide, the scaffold can be for example a macrocyclic complex described in or producing using a method described in WO2018183906 titled MACROCYCLIC COMPLEXES OF ALPHA-EMITTING RADIONUCLIDES AND THEIR USE IN TARGETED RADIOTHERAPY OF CANCER, which is incorporated herein by reference in its entirety. In an embodiment, the radionuclide is an alpha-particle emitter and the chelator is macropa-NCS.

Other examples of radionuclides include, but are not limited to, $^{67}$Cu, $^{177}$Lu, $^{213}$Bi, $^{90}$Y, $^{188}$Re, $^{47}$Sc, $^{225}$Ac, $^{227}$Th, $^{212}$Pb, $^{111}$In, $^{124}$I, $^{131}$I, $^{213}$Bi, $^{89}$Zr, $^{211}$At, $^{212}$B, and $^{186}$Re.

As described herein, the inventor found that when preparing a cytotoxic agent, improved stability, radiochemistry and specific activity of the resulting complex was obtained when the cytotoxin was coupled to the antibody prior to addition of the chelator and the radionuclide.

In another embodiment, the cytotoxic agent has a radionuclide loss of less than 50, 40, 30, 25, 20, 15, 10, 5 or 1% within 48 hours, optionally within 48 hours of preparation of the cytotoxic agent. In another embodiment, the cytotoxic agent has a radionuclide loss of less than 50, 40, 30, 25, 20, 15, 10, 5 or 1% within 7 days, optionally within 7 days of preparation of the cytotoxic agent. In a further embodiment, the cytotoxic agent has a radionuclide loss of less than 10, 5, 2 or 1% within 7 days, optionally within 7 days of preparation of the cytotoxic agent.

Specific activity is the activity per quantity of a radionuclide and is a physical property of that radionuclide. It may be measured in the cytotoxic agent, for example, as MBq/mmol of the antibody; MBq/microgram of antibody; mCi/mmol of antibody; mCi/microgram of antibody. In a further embodiment, the specific activity of the cytotoxic agent is at least 3, 4, 5 or 6 kBq/microgram of the antibody when the radionuclide is an alpha emitter such as $^{225}$Ac, optionally wherein the cytotoxic agent is of 95% purity. In another embodiment, the specific activity of the cytotoxic agent is at least 0.2, 0.3, 0.4, 0.5, 0.6, 0.7, 0.8, 0.9 or 1.0 kBq/microgram of antibody when the radionuclide is a beta or gamma emitter, optionally wherein the cytotoxic agent is of 95% purity.

Compositions for Simultaneous Targeting of Different Domains of a Cell Surface Receptor The inventors have also shown that the simultaneous targeting of epidermal growth factor receptor at multiple domains using domain specific cytotoxic agents as described herein enhances internalization and cytotoxicity in vitro and in vivo.

Accordingly, also provided herein is a composition comprising
  (a) a first cytotoxic agent comprising a first antibody that specifically binds a first epitope of a target cell surface receptor, and
  (b) a second cytotoxic agent comprising a second antibody that specifically binds a second epitope of the target cell surface receptor,
    wherein at least one of the first and second cytotoxic agent comprises a cytotoxin, wherein the cytotoxin is linked directly or indirectly to the antibody, and
    wherein at least one of the first and second cytotoxic agent comprises a radiolabel, wherein the radiolabel comprises a radionuclide and optionally a scaffold, wherein the scaffold is directly or indirectly coupled to the antibody.

In one embodiment, the first epitope is in a first extracellular domain of the cell surface receptor and the second epitope is in a second extracellular domain of the cell surface receptor.

The first extracellular domain and the second extracellular domain are different extracellular domains of the same cell surface receptor. For example, if a cell surface receptor has 4 extracellular domains, the first antibody or could specifically bind any one of domains I-IV, and the second antibody could specifically bind any one of domains I-IV that is not the domain bound by the first antibody.

In one embodiment, the first cytotoxic agent comprises both a cytotoxin and a radiolabel and/or the second antibody comprises both a cytotoxin and a radiolabel. The cytotoxin comprised in the first cytotoxic agent may be same or different from the cytotoxin comprised in the second cytotoxic agent. Likewise, the radiolabel comprised in the first cytotoxic agent may be same or different from the radiolabel comprised in the second cytotoxic agent. In one embodiment, the cytotoxin comprised in the first cytotoxic agent is the same cytotoxin comprised in the second cytotoxic agent and/or the radiolabel comprised in the first cytotoxic agent is the same radiolabel comprised in the second cytotoxic agent.

In one embodiment, the cell surface receptor is a member of the EGFR receptor family, optionally EGFR, HER2, HER3 or HER4.

In a further embodiment, the cell surface receptor is EGFR and the first antibody specifically binds extracellular domain III of EGFR and the second antibody specifically binds extracellular domain III of EGFR, optionally wherein the first antibody is nimotuzumab and the second antibody is 8709-scFv-Fc.

In another embodiment, the cell surface receptor is HER2 and the first antibody specifically binds extracellular domain IV of HER2 and the second antibody specifically binds extracellular domain II of HER2, optionally wherein the first antibody is trastuzumab and the second antibody is pertuzumab.

Compositions

The disclosure further provides compositions including pharmaceutical compositions comprising at least one cytotoxic agent described herein as an active ingredient and a pharmaceutically acceptable carrier.

Also provided is a package comprising a cytotoxic agent as described herein and optionally one or more of a carrier and a second cytotoxic agent. In the package the cytotoxic agent may be comprised in a first composition and the second cytotoxic agent is comprised in a second composition, where each composition provided in separate vials.

As used herein, the term "pharmaceutically acceptable carrier" is intended to include any and all solvents, dispersion media, coatings, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Optional examples of such carriers or diluents include, but are not limited to, water, saline, ringer's solutions, dextrose solution, and 5% human serum albumin.

A pharmaceutical composition is formulated to be compatible with its intended route of administration. Examples of routes of administration include parenteral, e.g. intravenous, intradermal, subcutaneous, oral (e.g. inhalation), transdermal (i.e., topical), transmucosal, and rectal administration.

In one embodiment, the cytotoxic agent (or cytotoxic agents) is prepared with a carrier that will protect it against rapid elimination from the body, such as a sustained/controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

In one embodiment, oral or parenteral compositions are formulated in dosage unit form for ease of administration and uniformity of dosage. Dosage unit form as used herein refers to physically discrete units suited as unitary dosages for the subject to be treated; each unit containing a predetermined quantity of active ingredient calculated to produce the desired therapeutic effect in association with the required pharmaceutical carrier. The specification for the dosage unit forms are dictated by and directly dependent on the unique characteristics of the (or cytotoxic agents) and the particular therapeutic effect to be achieved, and the limitations inherent in the art of preparing such an active ingredient for the treatment of individuals.

The composition can also contain more than one active ingredient as necessary for the particular indication being treated, optionally those with complementary activities that do not adversely affect each other. Alternatively, or in addition, the pharmaceutical composition can comprise an agent that enhances its function, such as, for example, cytokine, chemotherapeutic agent, or growth-inhibitory agent. Such molecules are suitably present in combination in amounts that are effective for the purpose intended.

Methods of Production

Another aspect of the disclosure is a method for making a cytotoxic agent as disclosed herein.

Also provided is a method of making a cytotoxic agent. It was found that improved stability of the resulting antibody cytotoxin radioisotope complex, radiochemistry and specific activity (defined as MBq/mmol of antibody; MBq/microgram of antibody; mCi/mmol of antibody; mCi/microgram of antibody) was obtained when the cytotoxin was coupled to the antibody prior to addition of the chelator and the radionuclide.

Accordingly a further aspect includes a method of making a cytotoxic agent comprising:
  coupling an antibody specific for a disease cell surface receptor with a cytotoxin to produce an antibody drug conjugate (ADC);
  optionally reacting the ADC with a bifunctional radionuclide chelator to produce an ADC-scaffold wherein the scaffold is conjugated to the antibody of the ADC;
  radiolabeling the ADC or optionally the ADC-scaffold to produce the cytotoxic agent.

The antibody can be any therapeutic antibody. As described herein, at least 5 different antibodies were used to produce the radiolabeled ADC. For example, the antibody can be a monoclonal antibody. The antibody can be an antibody fragment for example of a monoclonal antibody or the antibody can be a single chain antibody. Preferably the antibody is humanized or a human antibody. A number of suitable antibodies are known in the art including ones described herein.

The target receptor can be any receptor preferably one that is present differentially on disease cells. In one embodiment, the cell surface receptor is selected from an EGFR family member, EphA2 and/or IGF-1R.

In various embodiments, the cytotoxin is first reacted with a bifunctional linker, to produce a cytotoxin-linker and the cytotoxin-linker is reacted with the antibody to couple the antibody with the cytotoxin.

The reaction can be conducted under conditions to obtain a desired ratio of cytotoxin (e.g. drug) to antibody. For example, the cytotoxin linker or cytotoxin can be reacted with the antibody using a 5-50 mole excess equivalent of cytotoxin linker or cytotoxin.

For example, in some embodiments the coupling step is carried out under conditions to produce a cytotoxin to antibody ratio of approximately 3-4:1.

The cytotoxin can be for example any cytotoxin described herein. In some embodiments the cytotoxin is selected from the group consisting of maytansine and derivatives thereof (maytansinoids), auristatins calicheamicins, duocarmycins, doxorubicin, anthracyclines, amanitins and camptothecins.

The reaction can also be conducted under conditions to obtain a desired ratio of antibody to radionuclide. For example, in one embodiment, each scaffold carries one radionuclide and each antibody is coupled to 1-3 scaffolds, for an antibody: radionuclide ratio of 1:1 to 1:3.

As also described herein, various chelators are known for radionuclide labelling. In one embodiment, the bifunctional radionuclide chelator is p-SCN-Bz-DOTA or a derivative thereof.

Each of the various steps can be subjected to purification before proceeding with a further step. Similarly radioprotectors can be included in the radiolabelling reaction mixtures. In addition, the method can include a step of purifying the cytotoxic agent.

Particular methods are described in the Examples. The method can comprise one or more or all of the steps described therein.

Methods of Use

The present disclosure also provides a method of treating a disease comprising administering an effective amount of at least one cytotoxic agent or composition as disclosed herein a subject in need thereof, wherein the cell surface receptor is present on disease cells.

In one embodiment, an effective amount of at least one cytotoxic agent or composition disclosed herein is used for treating a disease in a subject, wherein the cell surface receptor is present on disease cells. In another embodiment, at least one cytotoxic agent or composition as disclosed herein is used in the preparation of a medicament for treating a disease in a subject, wherein the cell surface receptor is present on disease cells. In a further embodiment, at least one cytotoxic agent or composition as disclosed herein is provided for use in treating a disease in a subject, wherein the cell surface receptor is present on disease cells.

Also provided herein is a method of treating a disease comprising administering an effective amount of:
(a) a first cytotoxic agent comprising a first antibody thereof that specifically binds a first epitope of a target cell surface receptor, and
(b) a second cytotoxic agent comprising a second antibody that specifically binds a second epitope of the target cell surface receptor,
wherein at least one of the first and second cytotoxic agent comprises a cytotoxin,
wherein the cytotoxin is linked directly or indirectly to the antibody, and
wherein at least one of the first and second cytotoxic agent comprises a radiolabel,
wherein the radiolabel comprises a radionuclide and optionally a scaffold, wherein the scaffold is directly or indirectly coupled to the antibody, and
wherein the disease is a disease associated with the cell surface receptor.

In one embodiment, the first epitope is in a first extracellular domain of the cell surface receptor and the second epitope is in a second extracellular domain of the cell surface receptor.

In one embodiment, an effective amount of at least the first cytotoxic agent and at least the second cytotoxic agent is used for treating a disease in a subject, wherein the cell surface receptor is present on disease cells. In another embodiment, at least the first cytotoxic agent and at least the second cytotoxic agent is used in the preparation of a medicament for treating a disease in a subject, wherein the cell surface receptor is present on disease cells. In a further embodiment, at least the first cytotoxic agent and at least the second cytotoxic agent is used or is provided for use in treating a disease in a subject, wherein the cell surface receptor is present on disease cells.

The first cytotoxic agent and the second cytotoxic agent may be administered in any order, for example simultaneously, sequentially or separately. In one embodiment, the disease is cancer.

In another embodiment, the cancer is a solid cancer.

In another embodiment, the cancer is a stage III or stage IV cancer.

In one embodiment, the cancer is a cancer that overexpresses the cell surface receptor. As used herein, a cancer that "overexpresses" a cell surface receptor is a cancer that has higher expression levels of the cell surface levels of the receptor compared to a non-cancerous cell of the same tissue type. A cancer that "overexpresses" includes a cancer that expresses the cell surface receptor, where a non-cancerous cell of the same tissue type does not express the cell surface receptor.

It is known for example that overexpression of EGFR is implicated in cancers of epithelial origin including, but not limited to, squamous cell head & neck, glioma, non-small cell lung, colorectal, breast (optionally triple negative breast cancer) and cervical cancers. In one embodiment, the cell surface receptor is EGFR and the disease is cancer, optionally a cancer of epithelial origin.

It is also known that the overexpression of HER2 is implicated in cancer including breast and ovarian cancer. In one embodiment, the cell surface receptor is HER2 and the cancer is a cancer that overexpresses HER2 (also referred to herein as an HER2 positive cancer), optionally breast or ovarian cancer.

In another embodiment, the cell surface receptor is IGF-1R and the cancer is a cancer that overexpresses IGF-1R (also referred to herein as an IGF-1R positive cancer).

In one embodiment, the cancer is selected from breast cancers, osteosarcomas, pancreatic cancer, lung cancer and colorectal cancer. Different types of breast cancer including triple negative cancer.

As used herein, the terms "subject" and "animal" include all members of the animal kingdom, in one embodiment the subject is a mammal. In a further embodiment the subject is a human being. In one embodiment, the subject is a patient having a disease, such as a cancer, associated with a cell surface receptor.

An effective amount of the cytotoxic agent relates generally to the amount needed to achieve a therapeutic objective. Common ranges for therapeutically effective dosing of the cytotoxic agent of the disclosure may be, by way of non-limiting example, from about 0.1 mg kg body weight to about 50 mg/kg body weight. Common dosing frequencies may range, for example, from twice daily to once a week.

Efficaciousness of treatment is determined in association with any known method for diagnosing or treating the particular cancer. Alleviation of one or more symptoms of the cancer indicates that the cytotoxic agent confers a clinical benefit.

The cytotoxic agent may be administered in combination with at least one additional cancer therapy, including chemotherapy and/or radiation. The other cancer therapy may be administered may be administered in any order with the at least one additional cancer therapy, for example simultaneously, sequentially or separately.

As used herein, "treating a cancer" includes, but is not limited to, reversing, alleviating or inhibiting the progression of the cancer or symptoms or conditions associated with the cancer. "Treating the cancer" also includes extending survival in a subject. Survival is optionally extended by at least 1, 2, 3, 6 or 12 months, or at least 2, 3, 4, 5 or 10 years over the survival that would be expected without treatment with a cytotoxic agent or composition as described herein. "Treating the cancer" also includes reducing tumour mass and/or reducing tumour. Optionally, tumour mass and/or tumour burden is reduced by at least 5, 10, 25, 50, 75 or 100% following treatment with a cytotoxic agent or composition as described herein. "Treating the cancer" also includes reducing the aggressiveness, grade and/or invasiveness of a tumour.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

EXAMPLES

The following non-limiting examples are illustrative of the present disclosure:

Example 1

Cure of EphA2/EGFR Positive Triple Negative Breast Cancer Xenograft Using Novel $^{225}$Ac-Labeled Anti-EphA2/EGFR Bispecific Antibody-Drug Radioconjugate Triple negative breast cancer (TNBC) is deadly form of breast cancer (BC) that tends to occur in pre-menopausal women (1) and accounts for about 39% of BC cases in women under 50 years old. TNBC is characterized by a lack of estrogen (ER), progesterone (PR), and human epidermal growth factor II (HER2) receptors, and is typically associated with poor prognosis due to aggressive phenotype(s). Epidermal growth factor receptor I (EGFR) is overexpressed in over 85% of TNBC (2, 3) and therapies targeting this receptor have been evaluated albeit with very limited success (4, 5). In addition, about 70% of TNBC tumors overexpress the ephrin A2 (EphA2) receptor tyrosine kinase (6). Song et al. show that resistance to anti-EGFR therapeutics is at least in part due to the co-expression of EphA2 (7). Thus, EGFR and EphA2 are key drivers of tumor growth and metastasis in TNBC, but no approved therapeutic agents for TNBC co-target these receptors.

By combining the cytotoxic effects of potent chemotherapeutics (anticancer drugs) with tumor-targeting antibodies (t-Abs), antibody drug conjugates (ADCs) have been hailed as the next generation of therapeutics to drug resistant cancers. Emerging reports show that combining radioimmunotherapy (therapeutic isotopes attached to t-Abs) with ADC at therapeutic doses of both agents is more efficacious than single agents with acceptable systemic toxicity (8).

Described herein is a strategy in which an antibody is conjugated to a drug and complexed with alpha particle radiation (e.g. $^{225}$Ac). A $^{225}$Ac-labeled antibody drug radioconjugate using a bispecific EGFR/EphA2 monoclonal antibody (also referred to herein as the "bispecific EphA2 antibody" or "Bispec Ab") was developed and evaluated. It includes a cytotoxic agent PEGylated maytansine (PEG$_6$-DM1) linked to the antibody and radiolabeled with α-particle emitting actinium-225.

The antibody drug radioconjugate $^{225}$Ac-anti-EGFR/EphA2-PEG$_6$-DM1 is more potent than $^{225}$Ac-anti-EGFR/EphA2 or anti-EGFR/EphA2-PEG$_6$-DM1, or $^{225}$Ac-anti-EGFR-PEG$_6$-DM1, or $^{225}$Ac-anti-EphA2-PEG$_6$-DM1 (FIG. 2) in TNBC models that overexpress EGFR/EphA2. Without being bound by theory, this increased potency may be due to: (1) the combined potency of PEG$_6$-DM1 and a high linear energy transfer (LET) α-particle (therapeutic efficacy is 100 to 1000 times greater than other therapeutic radionuclides); (2) resistance to high LET α-particles has not been observed; (3) unlike other therapeutic radionuclides, the efficacy of alpha particles is not dependent on the oxygen gradient of the tissue and (4) bispecific t-Ab allows targeting of a broader range of cancer cells.

The efficacy of "naked" antibodies (those that do not contain a cytotoxic agent) is poor and patients frequently develop resistance. While there is currently no available literature on the use of bispecific antibody against EGFR/EphA2, there is a wealth of preclinical and clinical data on the use of anti-EGFR antibodies in TNBC. Anti-EGFR monoclonal antibodies, cetuximab and panitumumab have been extensively used in preclinical and clinical settings to treat EGFR positive breast cancers. In a small phase II study (19 patients) Crozier et al 2016 found an overall response rate (ORR) of 11% following the addition of cetuximab in patients on irinotecan regiment (9). Trial was terminated early because of the low response rate and rapid disease progression. Baselga et al 2013 investigated the benefit of adding cetuximab to cisplatin regimen in TNBC patients. ORR was 20% in patients treated with cisplatin plus cetuximab compared with 10% in cisplatin alone (10). Patients in the cetuximab plus cisplatin group also had better progression free survival compared with cisplatin alone, 3.7 months vs 1.5 months.

The widely accepted consensus in the field is that alpha-particle therapeutics such as 223RaCl2 (11) or when conjugated directly to a peptide 225Ac-PSMA 617 (for prostate cancer) (12) or antibody (212Pb-trastuzumab) (13) are effective only in micro-metastatic disease due the short range of travel of alpha particles. The present strategy is to use multiple drug molecules and alpha particles attached to bispecific t-Ab should be effective in both large tumors (primary tumors) as well as micro-metastases, where the PEG-DM1 component will lead to de-bulking of the tumor with concomitant eradication of wide-range of residual cells and micro-metastasis by the alpha particles. DM1 is an anti-microtubule agent that causes cell cycle arrest in the G2/M phase and apoptosis, and is the drug of choice for many ADCs in clinical trials. The characteristics of 225AC: t½ 10.0 days; energy range of 4 as is 6-8 MeV (cumulatively 28 MeV/decay) decays with the emission of 4 as, 3 β-disintegrations and daughter radionuclides namely; 221Fr-217At-213Bi-209Pb; alpha range of 50-80 µm with a linear energy transfer of up to 0.16 MeV/µm, makes it ideal for this setting. Recently, α particle therapies have shown remarkable success and now gaining clinical acceptance.

The materials and methods used for the following experiments are described in Examples 6-8.

Results:

Characterization of ADCs and Macropa Conjugated Antibodies.

Quality control of immunoconjugates were performed using SEC-HPLC with PBS (pH 7.2) as the mobile phase Bispec Ab, Bispec Ab-PEG$_6$-DM1-Low, Control-Ab, Control-AB-PEG$_6$-DM1-Low were eluted as a monomer peak at 11.5, 11.92, 10.91 and 11.3 respectively. Macropa conjugated antibodies Macropa-Bispec Ab, Macropa-Bispec Ab-PEG6-DM1-Low, Macropa-Control-Ab and Macropa-Control-Ab-PEG$_6$-DM1-Low were eluted at 11.23, 11.57, 10.04 and 11.1 respectively. Antibody aggregates, if present were eluted at 8.7 min. Aggregate or dimer formation for all antibodies were <2% and the presence of free ADCs was not detected.

Drug to Antibody ratio for antibody drug conjugates was calculated using UV spectroscopy and was found to be 3.8 and 3.4 for Bispec Ab-PEG$_6$-DM1-Low and Control-Ab-PEG$_6$-DM1-Low respectively. The UV spectra of Bispec Ab-PEG$_6$-DM1-Low and Control-Ab-PEG$_6$-DM1-Low as represented in FIG. 30 clearly denotes the conjugated DM1 drug by a hump at 254 nm apart from a distinct peak at 280 nm denoting the antibody.

Drug to antibody ratios shown in FIG. 30 were determined using UV method. Antibody and drug each have absorbance maxima at different wavelengths i.e. 280 and 254 nm respectively. Simultaneous equations were generated for both drug and antibody using the Beer-Lambert law. By solving the simultaneous equations, the number of drug per antibody was determined.

Antibody-Absorption at 280 nm        Equation 1

$$A_{280} = (\varepsilon_{drug}^{280} C_{drug} + \varepsilon_{mAb}^{280} C_{mAb})l$$

Antibody-Absorption at 254 nm        Equation 2

$$A_{254} = (\varepsilon_{drug}^{254} C_{drug} + \varepsilon_{mAb}^{254} C_{mAb})l$$

The average drug to antibody ratio was determined by dividing the $C_{drug}$ by $C_{mAb}$ and was expressed in moles of drug to moles of antibody.

Flow Cytometry

To determine the binding ability of immunoconjugates to EGFR, an in vitro binding assay was performed using flow cytometry. One point binding of Bispec Ab, Macropa-Bispec Ab, Control-Ab, Macropa-Control-Ab was measured against in EGFR positive MDA-MB-231 cells and EGFR negative MCF-7 cells in FIG. 2. Depending upon the relative fluorescent intensity, it was observed that there was no change in binding affinity of Bispec Ab, and Macropa-Bispec Ab. They displayed similar binding towards EGFR in MDA-MB-231. Control-Ab did not display any binding to EGFR in MDA-MB-231 cells which proves their inability to attach the EGFR receptor. None of the immunoconjugates of the bispecific EphA2 antibody displayed binding to MCF-7 which is a control cell line, confirming the specific binding nature of the bispecific EphA2 antibody immunoconjugates towards EGFR.

Radiolabeling of Immunoconjugates with $^{225}$Ac.

Radiolabelling of Bispec Ab and control-Ab with $^{225}$Ac was performed as per the standard laboratory protocol. Radiolabelling was monitored after 30 mins using iTLC. It was observed that >95% of $^{225}$Ac was labelled within 30 mins. The radiochemical purity for both the antibodies was >98% as witnessed through iTLC. Radiochemical yield obtained after purification was found to be >95% for $^{225}$Ac-Bispec Ab and $^{225}$Ac-Bispec Ab-PEG$_6$-DM1-Low and >75% for $^{225}$Ac-Control-Ab and $^{225}$Ac-Control-Ab-PEG$_6$-DM1-Low.

Radioligand Binding and Immunoreactive Fraction.

Effect of radiolabelling on binding of radioimmunoconjugates to EGFR was analysed using radioligand binding assay towards MDA-MB-231 cells. $^{225}$Ac-Bispec Ab and $^{225}$Ac-Bispec Ab-PEG$_6$-DM1-Low displayed phenomenal binding towards MDA-MB-231 cells was observed in FIG. 4. The estimated dissociation constant for $^{225}$Ac-Bispec Ab was found to be 13.08±0.95 nM which was nearly similar to 14.05±0.89 nM as obtained for $^{225}$Ac-Bispec Ab-PEG$_6$-DM1-Low confirming no much difference between the two immunoconjugates. Also binding affinities displayed that radiolabelling did not affect the binding ability of immunoconjugates to EGFR.

The immunoreactive fraction assay was performed to determine the extent of binding of $^{225}$Ac-Bispec Ab and $^{225}$Ac-Bispec Ab-PEG$_6$-DM1-Low towards MDA-MB-231 cells. As evident from the R square value of 0.88 and 0.89 respectively calculated using double inverse graph which is very close to 1, signifying efficient binding towards EGFR.

Internalization Assay:

An internalization assay for radiolabeled and non-radiolabeled immunoconjugates were performed using Incucyte live cell imaging system. The Incucyte Human FabFluor pH Red Antibody labelling reagent is attached to fluorescent probe which is highly sensitive to pH thereby producing fluorescent signals on pH which are being used to assess the internalization of immunoconjugates. Internalization assay for cold samples was performed at variable concentrations ranging from 0.2-500 nM for non-radiolabelled samples and 0.015-2nCi for $^{225}$Ac radiolabelled samples of all immunoconjugates as per mentioned in the protocol. Internalization of immunoconjugates was assessed depending upon the total number of red counts produced at the end of 48 h, which is directly proportional to the extent of internalization. It was observed that (FIG. 4) Bispec Ab-PEG$_6$-DM1-Low displayed efficient internalization at effective concentration of 42.98±0.01 nM which was 2.34 folds lower than Bispec Ab which displayed optimal internalization at 101±0.03 nM. This clearly shows that addition of drug aids in internalization efficiency. Further it was observed that labelling with $^{225}$Ac had a significant impact on internalization efficiency. $^{225}$Ac-Bispec Ab displayed efficient internalization only at 3.39±0.05 nM which is 29 folds lower as compared to Bispec Ab while $^{225}$Ac-Bispec Ab-PEG$_6$-DM1 was the best candidate as it displayed efficient internalization at mere concentration of 0.63±0.025 nM which is an astonishing 68 folds lower than Bispec Ab-PEG$_6$-DM1-Low, suggesting an enhanced internalization efficiency obtained from $^{225}$Ac labeled samples which was evident from the microscopic images obtained (FIG. 5). It can be seen in FIG. 5 that the highest levels of red are in panel "5J."

In Vitro Cytotoxicity

In vitro cytotoxicity of immunoconjugates was performed in MDA-MB-231 cells. As evident from internalization assay, the same trend was observed in the cytotoxicity assay. The ADCs displayed efficient toxicity compared to naked antibodies, which was evaluated based on their lower EC50 values obtained. Bispec Ab-PEG$_6$-DM1-Low displayed good cytotoxicity at an EC50 value of 28±0.05 nM which was 9/65 folds less as compared to Bispec Ab which had an EC50 value of 113±0.44 nM (FIG. 6). This cytotoxicity was considerably enhanced by labeling with $^{225}$Ac. $^{225}$Ac-Bispec Ab-PEG$_6$-DM1-Low displayed cytotoxicity having an EC50 value of only 0.14±0.26 nM which is around 200 folds lower than that obtained by Bispec Ab-PEG$_6$-DM1-Low and around 12.7 folds lower than $^{225}$Ac-Bispec Ab which had an Ec50 value of 1.88±0.64 nM. Efficiency of Bispec Ab was greatly enhanced by addition of DM1 drug and radiolabelling with $^{225}$Ac which was also evident from the microscopic images obtained (FIG. 7). It can be seen in FIG. 7 that the highest levels of red are in panel "7J."

Biodistribution Studies:

All mice were euthanized after 24 h and 168 h p.i. for the biodistribution. Tumor, blood, liver, and kidneys of mice had significant radioactivity accumulation at 24 h and 168 h p.i.

(FIGS. 8A and B) which is an expected condition since a radiolabelled antibody typically has long circulation half-life through renal and hepatic clearance. After 24 h p.i. mice administered with $^{225}$Ac-Bispec Ab-PEG$_6$-DM1-Low displayed a high tumor uptake of 7.73±0.522% IA/g which was around 1.3, 3.15 and 2.83 folds higher than mice administered with $^{225}$Ac-Bispec Ab, $^{225}$Ac-Control-Ab and $^{225}$Ac-Control-Ab-PEG$_6$-DM1-Low respectively. After 168 h p.i. radiolabelled immunoconjugates had cleared from all the organs except for liver and kidneys. Tumor uptake was gradually increased after 168 h p.i. which clearly defines the mechanism of $^{225}$Ac therapy, wherein the radiolabelled antibody gets accumulated in the tumor and constantly bombards the tumor thereby decreasing its growth. Tumor uptake for $^{225}$Ac-Bispec Ab-PEG$_6$-DM1-Low after 168 h p.i. was 13.787±1.22% IA/g which was 1.8 folds higher as compared to 24 h p.i. Mice administered with $^{225}$Ac-Control-Ab displayed negligible tumor uptake as compared to $^{225}$Ac-Bispec Ab and $^{225}$Ac-Bispec Ab-PEG$_6$-DM1-Low and difference was statistically significant (p<0.0001) which clearly defines the tumor specific uptake of the bispecific EphA2 antibodies.

In Vivo Therapy Studies Using $^{225}$Ac Labelled Immunoconjugates.

administered with Bispec Ab (FIG. 9E) and Bispec Ab-PEG$_6$-DM1-Low (FIG. 9F) reached the study endpoint within 41 and 49 days respectively and had to be sacrificed, two mice in each group showed a positive response to treatment which was determined by the decrease in the tumor volume. Mice administered with Bispec Ab-PEG$_6$-DM1-Low displayed better response as compared to Bispec Ab as one of the mice had a complete cured tumor (no tumor) within 29 days while the other mice had its tumor reduced to 55 mm$^3$ which is about 8.19 folds smaller as compared to two mice administered with Bispec Ab which had their tumor decreased to 738 mm$^3$ and 163 mm$^3$. Significant response was observed in mice administered with $^{225}$Ac-Bispec Ab-PEG$_6$-DM1-Low, (FIG. 9B) 6/7 mice showed complete recovery from tumor displaying no tumor at end of study. The combined average tumor curve of the groups is shown in FIG. 12.

Kaplan Meier curves (FIG. 9H) were used to calculate median survival time for all the groups. The median survival time was 41 days for mice administered with Bispec Ab and Bispec Ab-PEG$_6$-DM1-Low. Mice administered with $^{225}$Ac-Bispec Ab displayed a bit longer median survival time of 45 days. Median survival time could not be calculated for mice administered with $^{225}$Ac-Bispec Ab-PEG$_6$-DM1-Low as none of the mice had reached the study end point.

TABLE 1

Comparison of EC$_{50}$ values against four cell lines (A) in nM and (B) in nCi/mL

| Sample | EphA2 + ve | EGFR + ve | --ve EphA2/EGFR | ++ve EGFR + EphA2 |
|---|---|---|---|---|
| Bispec Ab | 240 ± 1.22 | 257 ± 1.47 | 412 ± 0.57 | 113 ± 0.44 |
| Bispec Ab-PEG6-DM1 | 55.11 ± 0.08 | 70.15 ± 0.41 | 378 ± 0.18 | 28.50 ± 0.05 |
| Ritxumab | 430 ± 0.78 | 381 ± 1.42 | 425 ± 0.38 | 374 ± 0.96 |
| Ritxumab-PEG6-DM1 | 211 ± 0.14 | 228 ± 1.11 | 300 ± 0.57 | 269 ± 0.69 |
| 225Ac-Bispec Ab | 3.11 ± 0.24 | 3.87 ± 0.29 | 5.2 ± 0.59 | 1.88 ± 0.64 |
| 225Ac-Bispec Ab-PEG6-DM1 | 2.14 ± 0.33 | 2.57 ± 0.57 | 4.48 ± 0.34 | 0.14 ± 0.26 |
| 225AcRitxumab | 6.14 ± 0.57 | 5.78 ± 0.35 | 6.22 ± 0.17 | 5.70 ± 1.9 |
| 225Ac-Ritxumab-PEG6-DM1 | 5.89 ± 0.19 | 5.47 ± 0.14 | 5.14 ± 0.66 | 3.3 ± 0.96 |
| Bispec Ab | N/A | N/A | N/A | N/A |
| Bispec Ab-PEG6-DM1 | N/A | N/A | N/A | N/A |
| Ritxumab | N/A | N/A | N/A | N/A |
| Ritxumab-PEG6-DM1 | N/A | N/A | N/A | N/A |
| 225Ac-Bispec Ab | 0.85 ± 0.12 | 0.67 ± 0.33 | 1.23 ± 0.29 | 0.5 ± 0.64 |
| 225Ac-Bispec Ab-PEG6-DM1 | 0.21 ± 0.15 | 0.15 ± 0.21 | 4.48 ± 0.11 | 0.04 ± 0.26 |
| 225AcRitxumab | 1.3 ± 0.87 | 1.2 ± 0.44 | 1.4 ± 0.9 | 1.5 ± 1.9 |
| 225Ac-Ritxumab-PEG6-DM1 | 0.98 ± 0.64 | 0.8 ± 0.15 | 1.1 ± 0.87 | 0.9 ± 0.22 |

Figure 9B:
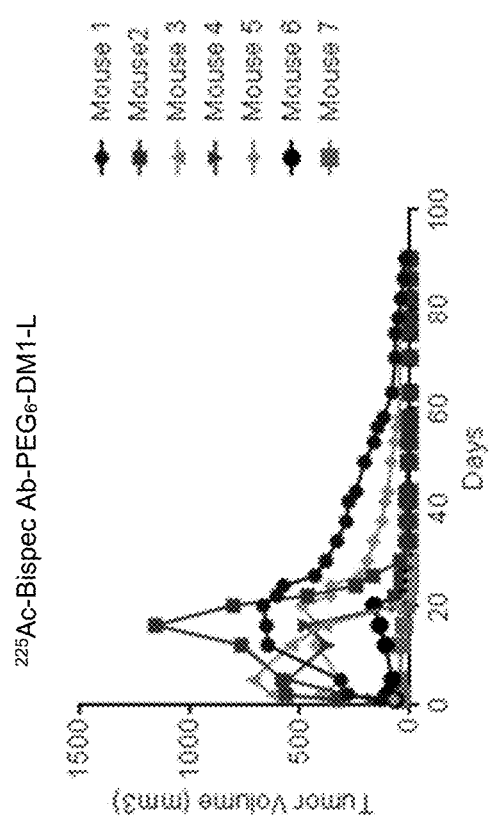
Figure 9D:
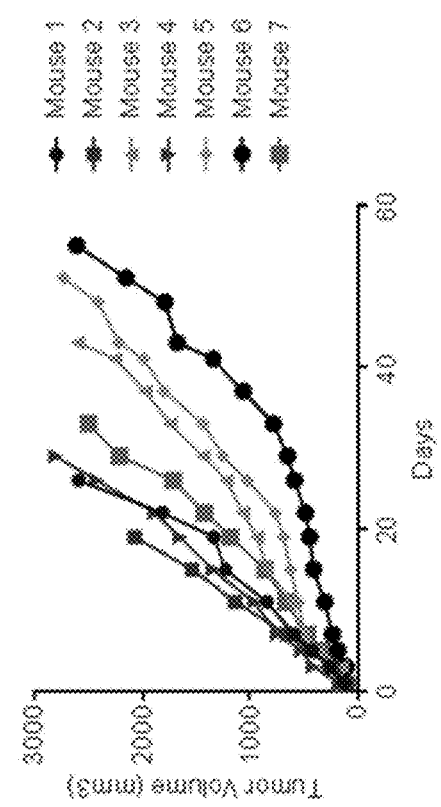
Figure 9A:
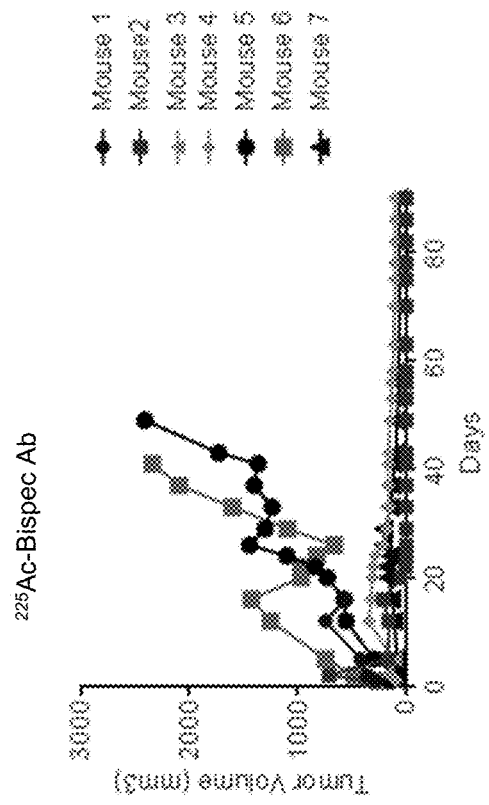
Figure 9C:
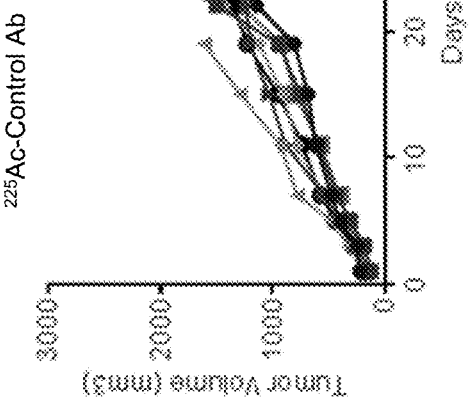
Figure 9E:
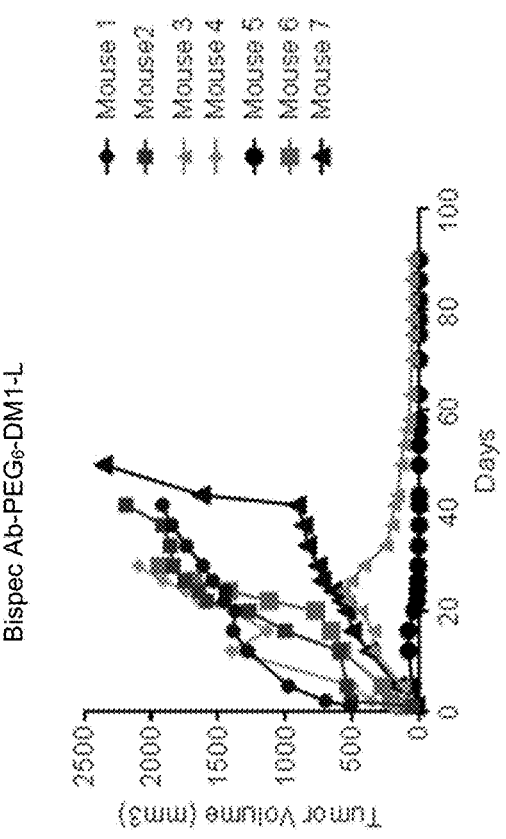
Figure 9F:
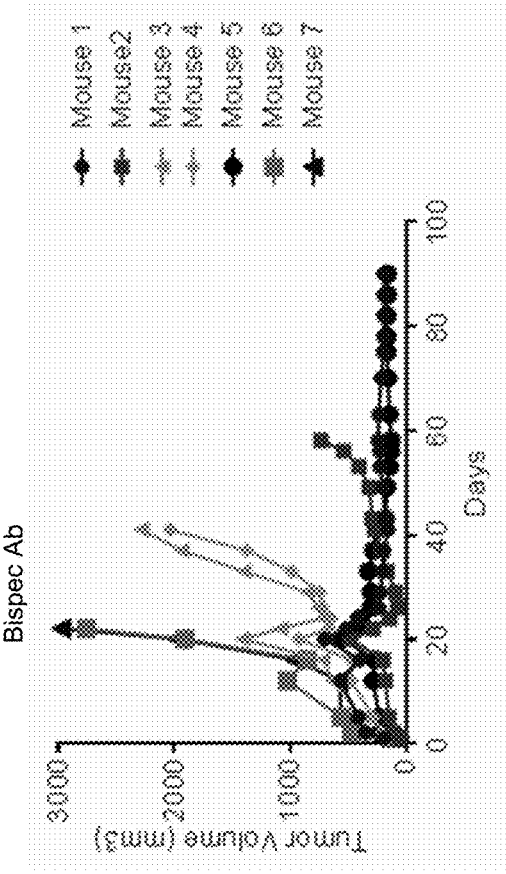
Figure 9G:
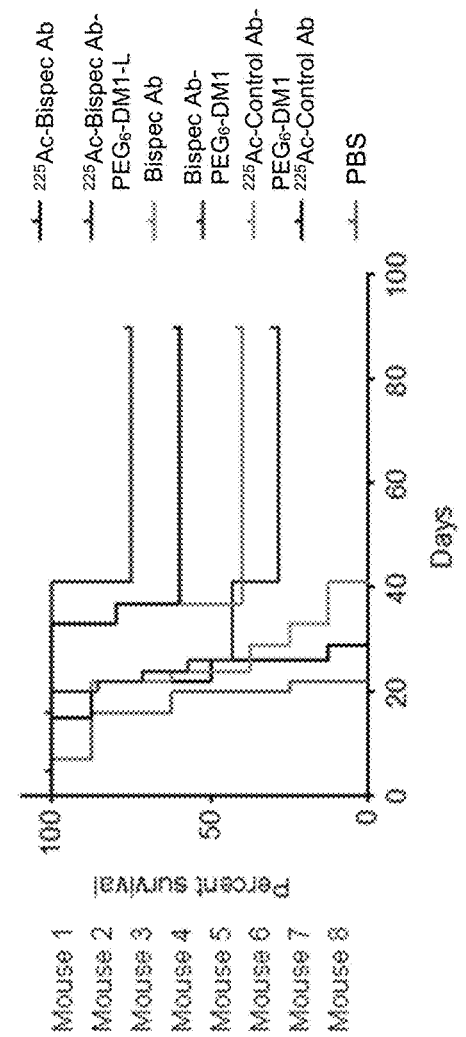
Figure 9H:
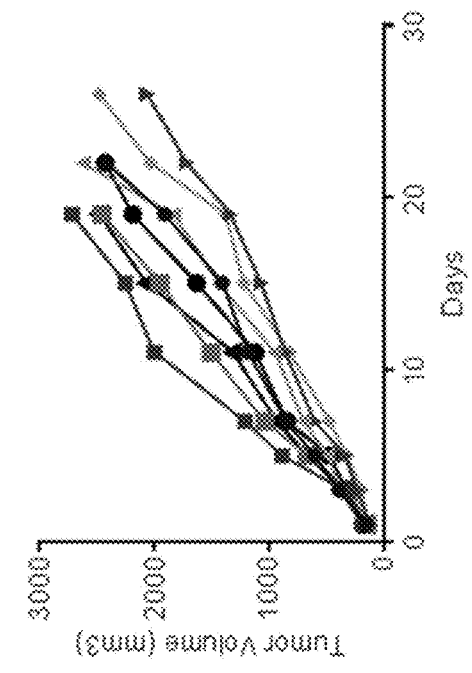

Considering the preliminary in vitro cytotoxicity data results, it is shown that radiolabelling of the bispecific EphA2 antibody with $^{225}$Ac has a profound effect on MDA-MB-231 breast cancer cells. This concept was then taken forward to in vivo studies using CD-1 nude mice bearing MDA-MB-231 tumors. Two doses of 450nCi has been reported as per the literature, herein three doses of 300nCi each were used, administered at an interval of 10 days. Therapeutic efficiency was monitored by measuring the change in tumour size using a caliper. It was observed that all the mice in PBS (FIG. 9G) group reached the study end point (1500 mm3) within 19 days and were sacrificed. 7 out of 7 mice injected with $^{225}$Ac-Control-Ab (FIG. 9C) were sacrificed by day 16; 4 out of 7 mice injected with $^{225}$Ac-Control-Ab-PEG6-DM1-Low reached the study end point within 22 days and the remainder reached endpoint by day 37 due to which they had to be sacrificed (FIG. 9D). Mice injected with non-radiolabelled Bispec Ab and Bispec Ab-PEG$_6$-DM1-Low displayed some response. 5/7 mice Example 2

Theranostics Pair of $^{111}$In/$^{225}$Ac Labeled Cixutumumab PEGylated-Maytansine Drug Conjugates for Insulin Growth Factor Receptor I (IGF-1R) Positive Cancers Anti-IGF-1R antibody cixutumumab was linked to DM1 and radiolabeled with $^{225}$Ac using DOTA as a chelator ($^{225}$Ac-cixutumumab-PEG$_6$-DM1) (FIG. 13).

In vitro, the IC50 of $^{225}$Ac-cixutumumab-PEG$_6$-DM1 was several folds higher than non-labeled antibody or ADC (cixutumumab-PEG$_6$-DM1) or $^{225}$Ac-cixutumumab).

The materials and methods used for the following experiments are described in Examples 6-8.

Results

The in-vivo potency of $^{225}$Ac-cixutumumab-PEG$_6$-DM1, $^{225}$Ac-human-IgG-PEG$_6$-DM1 and PBS control in IGF-1R positive SUM149PT (FIGS. 14A and B) and MCF7/Her18 (FIGS. 14C and D) xenografts was evaluated at a dose of 2.5 mg/kg administered by tail vein injection at 0 and 14 days interval.

Tumor growth inhibition was evaluated by the change in tumor volume/area using caliper measurements. In the $^{225}$Ac-cixutumumab-PEG$_6$-DM1 group, eight out of eight mice showed response to therapy as evidenced by slowed SUM149PT xenograft growth (FIGS. 14A and 14B). Among that, two mice tumor was completely cured on day 35, and 105, respectively and did not regrow or relapsed (>186 days after treatment). However, in this group six mice showed tumor relapse after treatment response and had to be sacrificed at study end point (2000 mm$^3$) on day 87 (2 mice), 95 (1 mouse), 97 (1 mouse), and 105 (2 mice). In $^{225}$Ac-control-IgG-PEG$_6$-DM1 treated SUM149PT group (FIG. 14B), all seven mice had reached the study end point (2000 mm$^3$) by day-186 and were sacrificed on day 37 (2 mice), 50 (1 mouse), 71 (2 mice), and 186 (1 mouse). In the PBS group (FIG. 14B), all six SUM149PT xenograft had reached the study end point (2000 mm$^3$) by day-100 and were dead on day 24 (1 mouse), 45 (1 mouse), 59 (1 mouse), 65 (1 mouse), and 100 (2 mice). The survival of the $^{225}$Ac-cixutumumab-PEG$_6$-DM1 treated group (100.0 days) was significantly higher than $^{225}$Ac-control-IgG-PEG6-DM1 (60.0 days, p≤0.05), and PBS (62.0 days, p≤0.05).

Based on these observations, the in-vivo potency of these tracers again on one more IGF-1R positive MCF7/Her18 xenograft at a dose of 2.5 mg/kg was evaluated (FIGS. 14C and D). In the $^{225}$Ac-cixutumumab-PEG$_6$-DM1 group, six out of six mice showed response to therapy as evidenced by slowed xenograft growth and two mice were alive at day-186 (FIGS. 14C and D). However, in this group four mice showed tumor relapse after treatment response and had to be sacrificed at study end point (2000 mm$^3$) on day 79 (1 mouse), 87 (1 mouse), 103 (1 mouse), and 179 (1 mouse). In $^{225}$Ac-control-IgG-DM1 treated group, one mouse reached the study end point (2000 mm$^3$) by day-153 and the other four had to be scarified before day-97. In the PBS treated group, all six mice had reached the study end point (2000 mm$^3$) by day-120 and were sacrificed on day 31 (1 mouse), 45 (1 mouse), 80 (1 mouse), 87 (1 mouse), 109 (1 mouse), and 127 (1 mouse). Kaplan Meier survival curves did not show any significant differences in median survival between $^{225}$Ac-cixutumumab-PEG$_6$-DM1 treated and PBS groups of MCF7/Her18 xenograft (FIG. 14D). The median survival of the PBS and $^{225}$Ac-control-IgG-DM1 group was 83.5 and 97.0 days, respectively, while that of $^{225}$Ac-cixutumumab-PEG6-DM1 was 141 days. In both cell lines addition of $^{225}$Ac ($^{225}$Ac-cixutumumab-PEG$_6$-DM1) to the antibody drug conjugate had >6000 fold increase in the cytotoxicity.

TABLE 2

EC50 values of antibodies immunoconjugates on breast cancer cells. The potency of the conjugates was estimated by plotting the increased cytotoxic red intensity as a function of cell death against the concentration. Sigmoidal dose response curves (variable slope) were generated using GraphPad Prism V. 5.02 (GraphPad Software Inc.).

|  | EC$_{50}$$^b$(nM) (MCF7/Her18 cells) | EC$_{50}$$^b$(nCi/mL) (MCF7/Her18 cells) |
|---|---|---|
| Cixutumumab-PEG$_6$DM1-Low | 54.34 +/− 1.5 nM | NA |
| Control-IgG-PEG$_6$-DM1-Low | 310.6 +/− 2.1 nM | NA |
| $^{225}$Ac-cixutumumab-PEG$_6$ | 0.008 +/− 0.002 nM | 0.26 +/− 0.06 nCi/mL |
| $^{225}$Ac-control-IgG-PEG$_6$ | 0.496 +/− 0.015 nM | 16.11 +/− 0.5 nCi/mL |

TABLE 2-continued

EC50 values of antibodies immunoconjugates on breast cancer cells. The potency of the conjugates was estimated by plotting the increased cytotoxic red intensity as a function of cell death against the concentration. Sigmoidal dose response curves (variable slope) were generated using GraphPad Prism V. 5.02 (GraphPad Software Inc.).

|  | EC$_{50}$$^b$(nM) (SUM149PT cells) | EC$_{50}$$^b$(nCi/mL) (SUM149PT cells) |
|---|---|---|
| Cixutumumab-PEG$_6$-DM1-Low | 33.4 +/−1.2 nM | NA |
| Control-IgG-PEG$_6$-DM1-Low | 275.2 +/− 1.7 nM | NA |
| $^{225}$Ac-cixutumumab-PEG$_6$ | 0.007 +/− 0.002 nM | 0.23 +/− 0.05 nM |
| $^{225}$Ac-control-IgG-PEG$_6$ | 0.383 +/− 0.028 nM | 12.43 +/− 0.9 nCi/mL |

$^b$Values are the mean of triplicates of at least two independent experiments.

Example 3

Simultaneous Targeting of Epidermal Growth Factor Receptor at Multiple Domains Using Domain-Specific Immunoconjugates Enhances Internalization and Cytotoxicity In Vitro and In Vivo Epidermal growth factor receptor I (EGFR) is overexpressed in most cancers of epithelial origin. An investigation into whether simultaneous targeting of EGFR using domain I/II and domain III specific immunoconjugates loaded with cytotoxic payloads would enhance the cytotoxicity against EGFR positive models in vitro and in vivo is described herein. Here, the in vitro and in vivo evaluation of anti-EGFR radioimmunoconjugates ($^{225}$Ac-8709-scFv-Fc) and antibody drug conjugates (ADCs: nimotuzumab-PEG$_6$-DM1) that target respectively domain I/II and domain III of the receptor is reported.

Methods: Immunoconjugates of 8709-scFv-Fc and nimotuzumab with anti-microtubule agent PEG$_6$-DM1 to generate 8709-scFv-Fc-PEG$_6$-DM1 and nimotuzumab-PEG$_6$-DM1 were developed. 8709-ScFv-Fc was also radiolabeled with $^{225}$Ac following conjugation with eighteen-membered ring macrocyclic chelator macropa-H2. Quality control of the conjugates was assessed using size exclusion HPLC, bioanalyzer, flow cytometry analysis and radioligand binding assays. The internalization and in vitro cytotoxicity of a combination of immunoconjugate and $^{225}$Ac-labeled radio-immunoconjugate of 8709-scFv-Fc and nimotuzumab was assessed using live-cell imaging on EGFR positive MDA-MB-468, MDA-MB-231 and TrR1 breast cancer cell lines with different EGFR density/cell. In vivo domain specificity was assessed by microPET/CT using $^{89}$Zr-8709-scFv-Fc in mice bearing MDA-MB-468 and EGFR negative (control) MDA-MB-435 xenografts. In vivo efficacy of a combination of $^{225}$Ac-8709-scFv-Fc+nimotuzumab-PEG$_6$-DM1 was evaluated in EGFR positive MDA-MB-468 triple negative breast cancer xenograft.

Results: Quality control showed no significant changes in the binding of the immunoconjugates towards EGFR. Combination of 8709-scFv-Fc+nimotuzumab led to 2.5-fold and 5.7-fold enhancement in internalization compared with the single agent nimotuzumab or 8709-scFv-Fc, respectively. Similarly, ADCs 8709-scFv-Fc-PEG$_6$-DM1+nimotuzumab-PEG$_6$-DM1 displayed a 6.3-34-fold higher internalization rate than the single agents. The highest internalization rates were observed using $^{225}$Ac-8709-scFv-Fc+nimotuzumab-PEG$_6$-DM1. The high internalization of the combined agents led to improved toxicity in EGFR positive cells. $EC_{50}$ of $^{225}$Ac-8709-scFv-Fc+nimotuzumab-PEG$_6$-DM1 in MDA-MB-468 was 0.75 nM compared with 4.3 nM and 56.7 nM for single agents $^{225}$Ac-8709-scFv-Fc and nimotuzumab-PEG$_6$-DM1, respectively, representing a 5.7 and 75.7 fold enhancement in cytotoxicity. In vivo radiotherapy studies with $^{225}$Ac-8709-scFv-Fc+nimotuzumab-PEG$_6$-DM1 delayed the growth of MDA-MB-468 xenograft while single agent nimotuzumab-PEG$_6$-DM1 or $^{225}$Ac-8709-scFv-Fc had almost no impact on tumor growth.

It is shown that simultaneous targeting of multiple domains of EGFR using domain I/II specific 8709-scFv-Fc and domain III specific nimotuzumab radioimmunoconjugates and immunoconjugates greatly enhanced the intracellular delivery of cytotoxic payloads to EGFR positive cells which resulted in improvements in in vitro cytotoxicity and in vivo efficacy.

BACKGROUND

Human epidermal growth factor receptor (EGFR), is a 170 kDa transmembrane cell surface glycoprotein which belongs to the subfamily of type-1 tyrosine kinase receptor. This family includes other members like, ErbB-2/HER2, ErbB-3/HER3 and ErbB-4/HER4 (14). Most aggressive cancers of epithelial origin including non-small cell lung (75-90%), squamous cell head and neck (90-100%) (15), glioma (90-100%), ovarian (16), colorectal (80-85%) (17), cervical and breast cancer overexpress EGFR (18, 19), making the receptor a prime therapeutic and imaging target. EGFR consists of an extracellular ligand binding domain and an intracellular domain. The extracellular binding domain of EGFR comprises of four binding subdomains—domain I, domain II, domain III and domain IV. Ligands of EGFR (epidermal growth factor, amphiregulin, transforming growth factor receptor a) bind to domain II (dimerization domain/loop) and initiate homo- and hetero-dimerization with other receptors which results in downstream signalling cascade (20).

Anti-EGFR antibodies for which there is extensive preclinical and clinical experience include cetuximab (21), panitumumab (22) and nimotuzumab (23, 24). These antibodies all bind to domain III of the receptor (25, 26). Apart from their toxicity towards EGFR positive cancer cells, cetuximab and panitumumab also have significant cutaneous toxicity in 45-100% of patients (27-29). This dose limiting cutaneous toxicity renders most anti-EGFR antibodies less favourable for treatment. Nimotuzumab is known to have low skin toxicities which is attributed to its optimized binding characteristics. This optimized binding ensures minimal transient binding to healthy tissues such as skin and gastrointestinal mucosa which have low receptor expression (23-30).

Developing strategies to target domain II of EGFR can enhance outcomes in EGFR positive cancers. Our hypothesis is that simultaneous targeting of different domains of EGFR can enhance the delivery of cytotoxic agents to EGFR-positive cells in vitro and in vivo. Recently, using phage display, Miersch et al. engineered a domain I/II specific anti-EGFR antibody named 8709-scFv-Fc. Expression, purification and binding characterization of the 8709-scFv-Fc antibody has been published (31). 8709-scFv-Fc fragment specifically binds to domain II of EGFR (and to a far lesser extent to domain I), without altering the binding affinity of other anti-EGFR antibodies such as cetuximab or nimotuzumab (domain III binder) (31). 8709-scFv-Fc has also been labeled with near infrared fluorescence dye IRDye800CW and evaluated as an image-guided surgical probe (32). Maximum accumulation was observed 48 h post injection. Flow cytometry results also confirmed that 8709-scFv-Fc did not compete with nimotuzumab for binding to EGFR. This data suggests 8709-scFv-Fc can be used in combination with domain III antibody such as nimotuzumab, to enhance the delivery of potent cytotoxic agents such as drugs and alpha particles.

Although many researchers have reported the potency of anti-EGFR antibodies towards EGFR positive cancers, the efficacy especially in triple negative breast cancer is still a bit ambiguous (33). Efficacy of these antibodies can be improved by conjugating the antibodies with drugs to obtain antibody drug conjugates (ADCs). Two of the anti-EGFR antibodies currently in phase I/II trials are ABT-414 and AMG-595 (34). AMG-595 is conjugated to a cytotoxic agent maytasine (DM1). Promising clinical data for anti-HER2 monoclonal antibody trastuzumab conjugated to DM1 (Kadcyla®) led to its approval and is now a standard of care for these patients (35, 36).

In the current experiments, tumors were large (>350 mm$^3$). Large tumors have a dramatically different prognosis than small tumors (<100 mm$^3$). Here it is shown that for large tumors the $^{225}$Ac-nimotumumab-PEG$_6$-DM1-low was effective while other conjugates were ineffective.

One goal of the present work is to improve the therapeutic efficacy of EGFR positive triple negative breast cancers. Here the simultaneously targeting of two domains of EGFR using antibodies/antibody fragments that bind to unique domains of the receptor—domain I/II using $^{225}$Ac-8709-scFv-Fc (a radioimmunotherapeutic) and domain III using nimotuzumab-PEG$_6$-DM1 (an ADC) is described and the in vitro cytotoxicity and in vivo effectiveness of these combination agents in models of triple negative breast cancer is evaluated.

Materials and methods are as described in Examples 6-8.

Results and Discussions

Production and Characterization of $^{89}$Zr

Specific activity was determined using published method by Holland et al (37) and the specific activity was found to be in the range of 673-1161 MBq/μmol. The radiochemical purity was 99.99% and the identity was confirmed by the presence of 909 keV and 511 keV peaks. The ICP-MS analysis of $^{89}$Zr-oxalate solutions were performed at Saskatchewan Research Council, Saskatoon and elemental impurity levels were found to be always below 30 ppm and all batches met the QC release specifications.

Characterization of ADCs and Macropa-Conjugated Antibodies

Quality control of immunoconjugates was performed using SEC-HPLC with PBS (pH 7.2) as mobile phase. 8709-scFv-Fc, nimotuzumab and control IgG and their respective macropa conjugates and ADCs were eluted as a monomer peak. Antibody aggregates and dimers, if present eluted at 8.7 min and 10.8 min, respectively. Aggregate or dimer formation for all antibodies were <5% and the presence of free drug PEGS-DM1 was not detected.

Electronic electrophoresis (bioanalyzer) was used to determine molecular weights and purities of ADCs. Bioanalyzer data displays a single band for each antibody (FIG. 16A), confirming the purity of immunoconjugates. It was observed that conjugation of drug to antibodies resulted in a negligible increase in the antibody molecular weight. The molecular weight of the immunoconjugates and their corresponding ADC's are represented in Table 3.

Drug to Antibody ratio for antibody drug conjugates was calculated using UV spectroscopy and was found to be 3.5, 3.7, 3.3 for 8709-scFv-Fc-PEG$_6$-DM1, nimotuzumab-PEG$_6$-DM1 and control IgG-PEGS-DM1, respectively. The UV spectra of 8709-scFv-Fc-PEG$_6$-DM1, nimotuzumab-PEG$_6$-DM1 and control IgG-PEGS-DM1 clearly denotes the conjugated DM1 drug by a hump at 254 nm apart from a distinct peak at 280 nm denoting the antibody.

Flow Cytometry

Binding profile of immunoconjugates to MDA-MB468 (high EGFR expression) and MDA-MB-435 (EGFR negative) was studied using flow cytometry. It was observed that all immunoconjugates displayed >90% binding to MDA-MB468 cells confirming their property to bind to EGFR. Negligible binding in MDA-MB-435 cells confirms the selective nature of antibody towards EGFR. A saturation binding curve was performed to determine the binding constants $K_D$ at which immunoconjugates bind to the cell. The trend for $K_D$ values was macropa conjugated 8709-scFv-Fc>8709-scFv-Fc-PEG$_6$-DM1>8709-scFv-Fc (FIG. 16B). Macropa conjugated 8709-scFv-Fc displayed 10.4 folds higher $K_D$ value (Table 4) as compared to 8709-scFv-Fc. No difference was found in the $K_D$ values of the nimotuzumab immunoconjugates (FIG. 16C).

Radiolabeling of Immunoconjugates with $^{225}$Ac and $^{89}$Zr

Radiolabeling with $^{225}$Ac was monitored after 30 mins using iTLC and SEC-HPLC. It was observed that, >95% of $^{225}$Ac was labeled within 30 mins. The radiochemical purity for both antibodies was >98% as observed by iTLC and SEC-HPLC. Radiolabeling with $^{89}$Zr was monitored after 30 mins using iTLC. It was observed that >95% of $^{89}$Zr was labeled within 30 mins. The radiochemical purity for $^{89}$Zr-8709-scFv-Fc was >98% as observed by iTLC.

Radioligand Binding and Immunoreactive Fraction

Figure 17A:
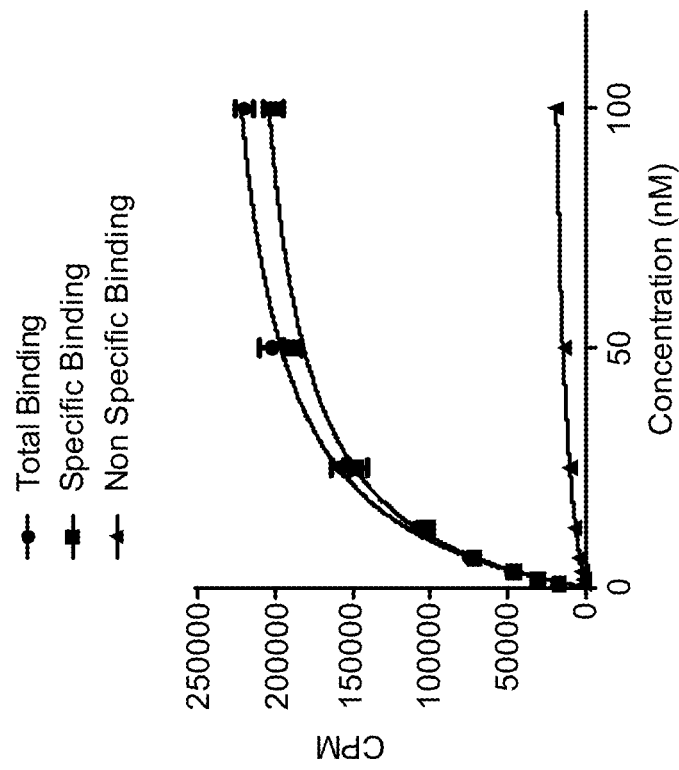

Effect of radiolabeling on the binding of radioimmunoconjugates to EGFR was analysed using radioligand binding assay towards MDA-MB-468 cells. $^{225}$Ac-8709-scFv-Fc showed high specific binding to MDA-MB-468 cells (FIG. 17A). The estimated dissociation constant for $^{225}$Ac-8709-scFv-Fc was found to be 14.5±0.88 nM which was similar to EC$_{50}$ value of macropa conjugated 8709-scFv-Fc (11.3 nM) obtained from flow cytometry analysis, confirming that binding affinity of 8709-scFv-Fc for MDA-MB-468 cells was not compromised after radiolabeling. The immunoreactive fraction of $^{225}$Ac-8709-scFv-Fc on MDA-MB-468 cells was 0.86 (FIG. 17B), indicating insignificant effect of conjugation/radiolabeling on the binding of the antibody.

In Vitro EGFR Domain II Binding of 8709-scFv-Fc.

Binding of 8709-scFv-Fc to EGFR domain II was studied by competitive binding experiment, using nimotuzumab to block the domain III of EGFR (FIG. 18). It was observed that addition of unlabeled 8709-scFv-Fc significantly (p≤0.0001) reduced the uptake of $^{225}$Ac-8709-scFv-Fc, whereas the addition of unlabeled nimotuzumab (domain III binding antibody) did not affect the binding of $^{225}$Ac-8709-scFv-Fc to EGFR in MDA-MB-468 cells. Pre-blocking of MDA-MB-468 cells with unlabeled 8709-scFv-Fc resulted in 23.2-fold reduction (at 50 nM concentration) in the binding of $^{225}$Ac-8709-scFv-Fc to EGFR whereas no effect was observed after pre-blocking with unlabeled nimotuzumab which indicates domain specificity binding of $^{225}$Ac-8709-scFv-Fc to domain/epitope II of EGFR. This effect was observed at all three concentrations.

Internalization of Radio(Immunoconjugates)

Internalization of immunoconjugates is a factor in determining its efficacy. Incucyte human FabFluor pH Red Antibody labeling reagent is attached to fluorescent probe which produces different fluorescent intensities at different pH and can be used to assess internalization of immunoconjugates. Internalization of immunoconjugates was assessed depending upon the total number of red counts produced at the end of 48 h, which is directly proportional to the extent of internalization. It was observed that for naked antibodies (FIG. 19A), combination of 8709-scFv-Fc+nimotuzumab displayed the highest internalization which was 2.47, 5.67 and 9.85 folds higher than nimotuzumab, 8709-scFv-Fc and control IgG, respectively. For ADC's too, (FIG. 19B) 8709-scFv-Fc-PEG$_6$-DM1+nimotuzumab-PEG$_6$-DM1 had a higher internalization rate, which was 6.29, 34 and 47-folds higher than for nimotuzumab-PEG$_6$-DM1, 8709-scFv-Fc-PEG$_6$-DM1 and control IgG-PEG$_6$-DM1, suggesting the enhancement of internalization of immunoconjugate in the presence of PEG$_6$-DM1 drug. For immunoconjugates labeled with $^{225}$Ac, the combination of $^{225}$Ac-8709-scFv-Fc+nimotuzumab-PEG$_6$-DM1 displayed highest internalization which was 9.47-fold higher than single agents $^{225}$Ac-8709-scFv-Fc, 13.82-fold higher than nimotuzumab-PEG$_6$-DM1 and 33.08-fold higher than $^{225}$Ac-control IgG (FIG. 19C). Microscope images (FIG. 19D) clearly display high number of red coloured cells in cells treated with the combined agents thereby confirming the enhanced internalization rate/delivery of this approach. It can be seen in FIG. 19D that the highest level of red is in the last panel of row 3 (lower right panel).

In Vitro Cytotoxicity

In vitro cytotoxicity of immunoconjugates was performed in three breast cancer cell lines MDA-MB-468, MDA-MB-231 and TrR1. In vitro cytotoxicity mirrored the trends seen in internalization (FIG. 20A-C). The ADCs displayed efficient toxicity compared to naked antibodies, which was evident from the lower EC$_{50}$ obtained (Tables 5 &6). Combination of 8709-scFv-Fc-PEG$_6$-DM1+nimotuzumab-PEG$_6$-DM1 enhanced the cytotoxicity compared with single agents with EC$_{50}$ of 22.68±0.12 nM which was 11.87, 7.05 and 2.50 folds lower than control IgG-PEG$_6$-DM1, 8709-scFv-Fc-PEG$_6$-DM1 and nimotuzumab-PEG$_6$-DM1, respectively, which demonstrates a significant synergistic advantage of the combined biparatopic effect of 8709-scFv-Fc (domain I/II)+nimotuzumab-PEG$_6$-DM1 (domain III). Cytotoxicity was significantly enhanced with the addition of $^{225}$Ac, thereby further decreasing the EC$_{50}$ value. It was observed that $^{225}$Ac-8709-scFv-Fc+nimotuzumab-PEG$_6$-DM1 displayed an EC$_{50}$ of just 0.75±0.06 nM, which was nearly 68 folds lower than non-radiolabeled 8709-scFv-Fc+nimotuzumab-PEG$_6$-DM1 and more that 116 folds lower than other immunoconjugates which clearly showed the enhanced toxicity attributed to $^{225}$Ac (Tables 5 & 6). Microscope images (FIG. 20D) of corresponding samples clearly show that MDA-MB-468 cells were completely compromised. It can be seen in FIG. 20D that the highest level of red is in the last panel of row 3 (lower right panel).

In Vivo MicroPET/CT Imaging of EGFR Domain I/II Using $^{89}$Zr-8709-scFv-Fc

In vivo binding of $^{89}$Zr-8709-scfv-Fc to domain II of EGFR was studied using micropet imaging at different time points 24 h, 48 h and 120 h p.i. (FIG. 21A-C). Tumor uptake of $^{89}$Zr-8709-scFv-Fc gradually increased from 4.21±0.76% % at 24 h to 5.4±2.32% at 120 h post injection. Mice injected with unlabeled nimotuzumab before the injection of $^{89}$Zr-8709-scFv-Fc also displayed similar tumor uptake starting at 4.60±0.449% at 24 h and 4.57±1.30% at 120 h (FIG. 21D) indicating that domain I/II binding of $^{89}$Zr-8709-scFv-Fc was not inhibited by the binding of nimotuzumab (domain III specific). Mice bearing control MDA-MB-435 xenografts displayed low tumor uptake at the end of 120 h suggesting no binding to control xenograft (FIG. 21B).

In Vivo Therapy

The efficacy of simultaneous targeting of domains I/II and III was explored using $^{225}$Ac-labeled immunoconjugate ($^{225}$Ac-8709-scFv-Fc) plus antibody drug conjugate (nimotuzumab-PEG$_6$-DM1) in an EGFR-positive MDA-MB-468 mouse xenograft model. Mice were treated with two doses of 450 nCi with/without ADCs administered at 10 days apart (FIG. 22A). All mice in PBS group reached the study end point (1500 mm$^3$) within 32 days and were sacrificed. Four out of seven mice injected with $^{225}$Ac-control IgG reached the study end point within 18 days and 3 mice had unexplained weight loss of >25% and red spots developed in their body covering approximately 65% of whole body and had to be sacrificed. Some non-specific anti-tumor effects was observed with $^{225}$Ac-control IgG+control IgG-PEG$_6$-DM1 as evident by 5 mice reaching the study end point by day-37. There was however, no significant decrease in tumor volume in this group. The slightly longer median survival in this group can be attributed to presence of PEG$_6$-DM-1 drug and $^{225}$Ac. Two mice in this group displayed red spots within 25 days similar of kind as monitored to the mice in the $^{225}$Ac-control IgG group and hence were sacrificed. Mice injected with $^{225}$Ac-8709-scFv-Fc displayed a better response to the tumor, which was evident by 4 mice reaching the study end point by day-50. Mice injected with combination of $^{225}$Ac-8709-scFv-Fc+nimotuzumab-PEG$_6$-DM1 displayed significant response to therapy, which is evident by only 2 mice reaching the study end point by 50 days. Five mice in this group consistently displayed a decrease in the tumor size, which strongly confirm enhanced therapeutic effect using a biparatopic approach with nimotuzumab-PEG$_6$-DM1 and $^{225}$Ac-8709-scFv-Fc. At the start of experiments mice in this group had an average tumor volume of 84 mm$^3$, which peaked on day-20 to 728 mm$^3$. At the end of the study all mice showed response and the tumor volume decreased to 62 mm$^3$.

Kaplan Meier curves (FIG. 22B) was calculated for all the groups. It was observed that $^{225}$Ac-control IgG had the lowest survival. The median survival range obtained was 16, 21, 25 and 32 days for $^{225}$Ac-control IgG, PBS, $^{225}$Ac-control IgG+IgG-PEG$_6$-DM1 and $^{225}$Ac-8709-scFv-Fc, respectively. Median survival with $^{225}$Ac-8709-scFv-Fc+nimotuzumab-PEG$_6$-DM1 had not been reached since 5/7 mice were still alive after study end period of 50 days. The survival of mice injected with $^{225}$Ac-control IgG has been significantly less (p<0.0001) compared to mice treated with $^{225}$Ac-8709-scFv-Fc+nimotuzumab-PEG$_6$-DM1. Mice in PBS group and $^{225}$Ac-8709-scFv-Fc group also had significantly lower survival time (p<0.001) in comparison with $^{225}$Ac-8709-scFv-Fc+nimotuzumab-PEG$_6$-DM1 group.

Discussion

A considerable number of factors account for the reasons why antibodies have not been able to live up to their expectations as immunotherapeutic. De novo and acquired resistance to small molecules and immunotherapeutic is a common phenomenon by cancer cells (38). Overexpression of alternate growth factor receptors (notably EGFR) and their ligands is a common cause of de novo resistance (39, 40). Apart from EGFR, overexpression of MDR1 is another cause of de novo resistance by cancer cells against small drug molecules (41-43)]. The conjugation of cytotoxic compounds such as DM1 to antibodies has had a profound effect on their effectiveness against primary and resistant cancer cells. However, studies have shown that DM1 is a substrate of MDR1 (41). PEGylated DM1 (PEG$_6$-DM1) used in this study is not an MDR1 substrate [38, (43, 44). Hartimath et al (45), has recently evaluated nimotuzumab-PEG$_6$-DM1-Low (drug to antibody ratio DAR of 3.5) and nimotuzumab-PEG$_6$-DM1-High (DAR of 7.3) in a model of EGFR-positive colorectal cancer xenograft.

In this study, nimotuzumab-PEG$_6$-DM1 (DAR of 3.3-3.5) and $^{225}$Ac-8709-ScFv-Fc was used to enhance the anti-tumor effects of both agents in a model of EGFR positive triple negative breast cancer.

Factors that affect the binding capabilities of radioimmunoconjugates and ADCs include reaction condition and chemicals used. In this study, the immunoconjugates were characterized using SEC-HPLC, bioanalyzer and flow cytometry. SEC-HPLC displayed predominantly monomeric peaks for all immunoconjugates without any free drug released. Bioanalyzer data displays single band for all the immunoconjugates thereby confirming the purity of samples. A negligible shift in the band position was observed which was mainly imparted due slight increase in the molecular weight of antibodies after conjugation with PEG$_6$-DM1. Flow cytometry analysis showed that conjugation of PEG$_6$-DM1 slightly altered the binding affinity of immunoconjugates as showed by a small increase in the $K_D$ value.

Macropa an eighteen-membered macrocyclic chelator which was recently reported by Thiele et al (46) was used here. Macropa conjugated antibodies were thoroughly screened for their structural, binding properties and stability of the complex. SEC-HPLC shows a clean profile of macropa conjugated antibodies suggesting the purity of samples. Flow cytometry analysis displays increased $K_D$ values for macropa conjugated antibodies but still have >85% binding towards MDA-MB-468 cells.

The effectiveness of ADCs can depend on drug cleavage in lysosomes following internalization (44, 47). In this study, Incucyte Fab Flour pH red dye for tracking the internalization of EGFR-positive cells by live cell imaging was used. This dye is linked to a pH sensitive fluorescent probe which is non-fluorescent at neutral pH 7.4. Antibodies/immunoconjugates located in early endosomes where pH is 6-6.4 show low fluorescence intensity, while localization in lysosomes (acidic pH of 4.7) show bright intensity. Hartimath et al recently showed that the internalization of nimotuzumab was enhanced by the number of PEG$_6$-DM1 drug molecules conjugated to the antibody (48). One intriguing finding of this study is the enhancement of internalization following the simultaneous binding of antibodies to different epitopes of the same receptor—EGFR. Similar to the work by Hartimath et al (48), it was confirmed here that conjugation of PEG$_6$-DM1 to antibodies 8709-ScFv-Fc and nimotuzumab enhances the internalization of the immunoconjugates compared with the naked antibody. Combination of 8709-scFv-Fc+nimotuzumab resulted to 2.5 to 6.7-fold increase in internalization when compared with the internalization of 8709-scFv-Fc or nimotuzumab single agents. In the case of $^{225}$Ac-8709-scFv-Fc+nimotuzumab-PEG$_6$-DM1, enhancement in internalization was up to 9.82-fold higher compared with the single agents. Significantly less internalization of domain I/II binder 8709-scFv-Fc/8709-scFv-Fc immunoconjugates was observed compared with nimotuzumab/nimotuzumab immunoconjugates. 8709-scFv-Fc binds to the dimerization loop of EGFR and limits homo- and hetero-dimerization. Cytotoxicity of antibodies and antibody conjugates is dependent in part on their ability to block signalling cascade by inhibiting receptor dimerization, elicit immune response via antibody dependent cellular cytotoxicity (ADCC) and/or release potent payload to the cell. The rate of internalization of antibody conjugates influences the in vitro cytotoxicity. This higher internalization rate significantly enhanced the in vitro and in vivo potency of the antibody conjugates. There was no clear trend of enhancement in cytotoxicity with increased receptor density in MDA-MB-468, MDA-MB-231 and TrR1 cell lines using 8709-scFv-Fc and 8709-scFv-Fc-PEG$_6$-DM1, which may indicate that the low of internalization rate of the antibody limits cytotoxicity. It is also not known if 8709-scFv-Fc causes ADCC. In vitro cytotoxicity of nimotuzumab was 1.3-3.6-fold higher that 8709-scFv-Fc in the cell lines studied (Table 5). Similarly, nimotuzumab-PEG$_6$-DM1 had a 1.2 to 2.8-fold higher cytotoxicity than nimotuzumab indicating the combined effects of payload internalization and ADCC (49). There was also a trend in enhancement of cytotoxicity with receptor density with the highest effect seen in MDA-MB-468 which has the highest EGFR density per cell. MDA-MB-468 has a high EGFR density of about 1-2 million EGFR/cell. Medium density would be about 500,000 EGFR/cell and low would be <100,000 EGFR/cell. Cytotoxicity increased after the addition of PEG$_6$-DM1 and $^{225}$Ac immunoconjugates. $^{225}$Ac is known to be highly potent and causes DNA double strand breaks. Microscopic images clearly display that cells were highly compromised with ruptured cells walls.

Unexpectedly, the combination of 8709-scFv-Fc and nimotuzumab antibodies and their immunoconjugates greatly enhanced cytotoxicity in all cell lines. In particular, the cytotoxicity of $^{225}$Ac-8709-scFv-Fc+nimotuzumab-PEG$_6$-DM1 in MDA-MB-468 cells was 6.6-fold greater than $^{225}$Ac-8709-scFv-Fc, 30-fold greater than 8709-scFv-Fc-PEG$_6$-DM1+nimotuzumab-PEG$_6$-DM1, 64-fold greater than 8709-scFv-Fc+nimotuzumab-PEG$_6$-DM1, 75.7-fold greater than nimotuzumab-PEG6-DM1, 106-fold greater than nimotuzumab and 213-fold greater than 8709-scFv-Fc.

The in vivo anti-tumor effects of $^{225}$Ac-8709-scFv-Fc+nimotuzumab-PEG$_6$-DM1 in MDA-MB-468 tumor bearing mice were then evaluated. It was confirmed using micro-PET/CT imaging that the uptake of $^{89}$Zr-8709-scFv-Fc was specific and was not blocked by the presence of nimotuzumab. Previous studies have reported 1000 nCi dose which was found to be lethal, but 450 nCi was well tolerated (unpublished data). 15 mg/kg nimotuzumab-PEG$_6$-DM1 was well tolerated (45). Two doses of $^{225}$Ac-8709-scFv-Fc+nimotuzumab-PEG$_6$-DM1 significantly prolonged the survival of mice bearing aggressive MDA-MB-468 xenograft with 5/7 mice surviving for more than 50 days. This survival benefit was more than 3.3 fold higher than for the individual agents $^{225}$Ac-8709-scFv-Fc or nimotuzumab-PEG$_6$-DM1. 5 mice in this group had complete tumor cure. Without wishing to be bound to theory, the enhancement in efficacy may be the result of enhanced internalization and therefore delivery of the cytotoxic payloads PEG$_6$-DM1 and $^{225}$Ac.

Summary

Using anti-EGFR antibodies (domain II specific 8709-scFv-Fc and domain III specific nimotuzumab), it is shown here that internalization and hence delivery of cytotoxic payloads can be greatly enhanced by combining (antibody) agents that target specific domains/epitopes of the receptor—in this case EGFR. This enhancement was up to more than 200-fold and led to improved outcomes in EGFR positive cells and tumor models in vivo.

TABLE 3

Molecular weights (kDa) of antibodies and antibody drug conjugates (ADCs) using electronic electrophoresis (bioanalyzer)

| | Sample | Molecular weight in kDa |
|---|---|---|
| 1 | 8709-scFv-Fc | 121.1 |
| 2 | 8709-scFv-Fc-PEG$_6$-DM1-Low | 128.9 |
| 3 | Nimotuzumab | 143.4 |
| 4 | Nimotuzumab-PEG$_6$-DM1-Low | 143.9 |
| 5 | Control IgG | 138.0 |
| 6 | Control IgG-PEG$_6$-DM1-Low | 143.0 |

TABLE 4

$K_D$ values for immunoconjugates obtained using flow cytometry

| Sr. No | Immunoconjugates | $K_D$ values |
|---|---|---|
| 1 | 8709-scFv-Fc | 1.1 ± 0.3 nM |
| 2 | 8709-scFv-Fc-PEG$_6$-DM1 | 4.2 ± 3 nM |
| 3 | Macropa-8709-scFv-Fc | 11.3 ± 8 nM |
| 4 | Nimotuzumab | 4.1 ± 2.2 nM |
| 5 | Nimotuzumab-PEG$_6$-DM1 | 3 ± 0.2 nM |
| 6 | Macropa-Nimotuzumab | 3.2 ± 1.4 nM |

TABLE 5

Non-radiolabeled immunoconjugates and their corresponding EC$_{50}$ (in nM) values in MDA-MB-468, MDA-MB-231 and TrR1 cell lines

| Sample | MDA-MB-231 | MDA-MB-468 | TrR-1 |
|---|---|---|---|
| Control IgG | 344 ± 1.22 | 344 ± 1.21 | 238 ± 0.43 |
| Control IgG-PEG$_6$-DM1 | 381 ± 0.24 | 269 ± 0.27 | 151 ± 0.17 |
| 8709-scFv-Fc | 228.3 ± 0.23 | 288 ± 0.23 | 198 ± 0.12 |
| 8709-scFv-Fc-PEG$_6$-DM1 | 150 ± 0.04 | 160 ± 0.34 | 129 ± 0.07 |
| Nimotuzumab | 109 ± 0.04 | 80 ± 0.02 | 151 ± 0.5 |
| Nimotuzumab-PEG$_6$-DM1 | 95 ± 0.18 | 56.8 ± 0.07 | 109 ± 0.04 |
| 8709-scFv-Fc + Nimotuzumab | 78.9 ± 0.29 | 48 ± 0.05 | 62 ± 0.08 |
| 8709-scFv-Fc-PEG$_6$-DM1 + Nimotuzumab-PEG$_6$-DM1 | 53.69 ± 0.22 | 22.68 ± 0.12 | 42.18 ± 0.52 |

TABLE 6

Radiolabeled immunoconjugates and their corresponding EC$_{50}$ (in nM and nCi) values in MDA-MB-468

| Samples | EC$_{50}$ (in nM) | EC$_{50}$ (in nCi) |
|---|---|---|
| $^{225}$Ac-control IgG | 5.1 ± 0.7 | 1.9 |
| $^{225}$Ac-control IgG + Control IgG-PEG$_6$-DM | 2.7 ± 0.12 | 1.39 |
| $^{225}$Ac-8709-scFv-Fc | 4.3 ± 0.5 | 0.92 |
| $^{225}$Ac-8709-scFv-Fc + Nimotuzumab-PEG$_6$-DM1 | 0.75 ± 0.06 | 0.14 |

Example 4

Nimotuzumab Radiolabeled Using DOTA as Chelator for $^{225}$Ac

FIG. 23 depicts the $^{225}$Ac-nimotuzumab-PEG$_6$-DM1.

Using $^{225}$Ac-Nimotuzumab-PEG$_6$-DM1-low (3-4 DAR), 3/8 mice bearing DLD-1 colorectal tumors were completely cured (FIG. 24). In the other groups shown in FIG. 25 no cures were observed.

Materials and methods were as described in Examples 6-8.

Example 5

Simultaneous Targeting of HER2 at Multiple Domains Using Domain-Specific Immunoconjugates Enhances Internalization and Cytotoxicity In Vitro and In Vivo The best in vitro effects (cytotoxicity (FIG. 28) and internalization (FIG. 27)) were seen with a biparatopic approach using $^{225}$Ac-pertuzumab-PEG$_6$-DM1 (domain II)+ $^{225}$Ac-trastuzumab-PEG$_6$-DM1 (domain IV) in resistant HER2 expressing cells (JIMT).

In an in vivo study, the biparatopic drug combination of $^{225}$Ac-pertuzumab-PEG$_6$-DM1 (domain II) $^{225}$Ac-trastuzumab-PEG6-DM1 (domain IV) resulted in significant tumor control compared with the other groups.

Materials and methods were as described in Examples 6-8.

Example 6

Materials and Methods

General

All reagents and solvents were obtained from commercial suppliers and used without further purification. DM1 drug was obtained from Toronto Research Chemicals, Inc (Toronto, ON) and NHS-PEG$_6$-malmide was purchased from Biochempeg (Watertown, Mass.). Macropa-NH2 can be purchased from MCE MedChem Express (Catalogue number HY-111895A) https://www.medchemexpress.com/macropa-nh2-hydrochloride.html) and Macropa-NCS ($C_{27}H_{35}N_5O_8S$) can be purchased from GLPBIO (Catalog No. GC33335) https://www.glpbio.com/macropa-ncs.html]; DOTA, and its bifunctional derivatives such as p-SCN-Bn-DOTA and Meo-DOTA-NCS or Breast cancer cell lines MDA-MB-231 and, MDA-MB-468 were obtained from ATCC (Manassas, Va.) and cultured in monolayers in, DMEM media. Trastuzumab-resistant human breast cancer cell line (TrR1) derived from MDA-MB-231 that stably expresses HER2 was obtained from Dr. Robert Kerbel, Sunnybrook and Women's College Health Sciences Centre in Toronto, Ontario, Canada. MDA-MB-435 cells were obtained from ATCC and cultured in RPMI media. MCF-7 cells control cell line was obtained from ATCC and cultured in F12-K media. All media was supplemented with 10% fetal calf serum and cells were maintained in a humidified atmosphere with 5% $CO_2$ at 37° C. $^{225}$Ac was generously provided by Canadian Nuclear Laboratories (CNL, Chalk River ON)

Production of $^{89}$Zr

The $^{89}$Zr-oxalate was produced at the Saskatchewan Centre for Cyclotron Sciences (SCCS), University of Saskatchewan (Saskatoon SK). Yttrium coated (10 mm diameter and 200 μm thickness) on a coin shaped niobium (24 mm diameter and 1 mm thickness) target supplied by Advanced Cyclotron Systems Inc (ACSI), was irradiated with an incident beam energy of 17.8 MeV providing a degraded transmitted energy through an aluminium degrader of 12.8 MeV and a current of 40 μA for 2 hours on an in-house beam-line on TR-24 cyclotron to produce $^{89}$Zr via the $^{nat}$Y(p, n)$^{89}$Zr reaction. During irradiation the target was cooled on the frontal side by Helium gas and on the back side by chilled water. After the irradiation, the target was left in the target station for 2-3 hours to allow decay of short-lived isotopes. Then target was released in the lead pig and transported to the hot cells on the lead shielded cart.

$^{89}$Zr was separated as $^{89}$Zr-oxalate from the irradiate yttrium coin as described by Queern et al (50). Briefly, to a dissolution vessel charged with the irradiated target 2 N trace metal HCl (4 mL) was added slowly. The resulting solution was warmed to 80° C. for 20 mins and cooled to room temperature before loading onto a pre-conditioned column of hydroxamate resin (100 mg). A dissolution vessel and target body rinsed with 2 N trace metal HCl (2 mL) and loaded onto hydroxamate resin. The hydroxamate resin was rinsed with 2 N HCl (14 mL) followed by trace select water (10 mL). Finally, $^{89}$Zr was eluted with 1.5 mL of 1.0 M Oxalic acid. $^{89}$Zr-oxalate was characterized for activity amount, half-life, radionuclidic purity, elemental impurities and specific activity. The final activity of purified $^{89}$Zr-oxalate was measured in the Capintec dose calibrator (CRC-55t PET). The $^{89}$Zr-oxalate solutions were tested for radionuclidic identity and purity using a high purity germanium (HPGe) detector (Ortec, Oak Ridge, Tenn.).

Synthesis of Radiolabeled Antibody Drug Conjugate

Synthesis of Drug Linker and Antibody Drug Conjugates

Synthesis of DM1-PEGS-NHS was achieved using a bifunctional linker mal-PEG$_6$-NHS and DM1 as previously described (36). Briefly, Maytansinoid (1) (DM1) was reacted with bifunctional linker NHS-PEG-Mal in 50 mM PBS/THF for 6 h at room temperature to generate the NHS-PEG-DM1. The NHS-PEG-DM1 was analyzed by mass spectrometry and NMR. Different fold excess of NHS-PEG-DM1 was reacted with antibody in 0.1 M HEPES pH 8.5 at room temperature for 3 h followed by 4° C. for 20 h to yield antibody-PEG6-DM1-Low (3-4 drugs per antibody) or Nmab-PEG6-DM1-High (7-8 drugs per antibody).

Synthesis of ADCs

Target specific and control antibody were conjugated with DM1-PEG$_6$-NHS. For example, a human antibody anti-maltose binding protein (MBP IgG) was used as a control antibody. DM1-PEG$_6$-NHS (20 mg/mL in DMSO stock solution) conjugation reactions were optimized for pH, buffers and reaction time.

The target antibodies, such as nimotuzumab, pertuzumab, trastuzumab, ritxumab bispecific anti-EphA2 antibody, cixutumumab, 8709-scFv-Fc and control antibody (MBP IgG) were conjugated with DM1-PEGS-NHS to generate nimotuzumab-PEG$_6$-DM1, pertuzumab-PEG$_6$-DM1, trastuzumab-PEG$_6$-DM1, ritxumab-PEG$_6$-DM1, bispecific anti-EphA2-PEG$_6$-DM1, cixutumumab-PEG$_6$-DM1, 8709-scFv-Fc-PEG$_6$-DM1 and control IgG-PEG$_6$-DM1 ADCs.

DM1 (73.8. 0.1 mmol) was dissolved in 1 mL of THF and 2-fold excess N-hydroxysuccinimide-polyethylene-glycol-6-maleimide (NHS-PEG6-Mal, 120.2 mg, 0.2 mmol) in 1.5 mL of THF:PBS (50 mM, pH 6) 2:1 v/v was added to the DM1 solution. The reaction was stirred at room temperature for 6 h and was monitored using thin layer chromatography (TLC). At the end of the reaction, the crude mixture was purified using column chromatography with silica gel eluting with ethanol/dichloromethane 6/94 v/v. The excess solvents and moistures were removed using ultra-high vacuum giving 80.1 mg (67.4%) of DM1-PEG6-NHS. H1 NMR (CDCl3, reference 7.26 ppm) δ 0.79 (6H, s), 1.21-1.34 (16H, m), 1.41-1.52 (3H, s), 1.62-1.73 (6H, s), 2.01-2.21 (1H, d), 2.22-2.64 (4H, m), 2.71-2.75 (4H, s), 2.82-3.01 (10H, m), 3.02-3.20 (5H, s), 3.31-3.42 (5H, m), 3.52-3.61 (2H, s), 3.72-3.81 (4H, d), 3.91-4.01 (4H, s), 4.2 (3H, m), 4.71-4.81 (4H, m), 5.23-

5-41 (2H, m), 5.61-5.81 (1H, m), 6.25-6.4 (2H, m), 6.45-6.61 (4H, m), 6.8 (2H, s). ESI MS: m/z found, 1340.84828 (M+H), calcd 1339.88788.

To prepare ADCs with low or high drug to antibody ratio (DAR) (low DAR 3-4), (high DAR 7-8) a 5-50 mole excess equivalent of drug linker DM1-PEG$_6$-NHS was used to optimize the conjugation of the antibodies to obtain a low (target specific antibody-PEG$_6$-DM1-Low) DAR. target specific and control antibody (5 mg/mL in PBS) were buffer exchanged in centrifugal filters (Amicon Ultra-4 Centrifugal Filter 10K NMCO, EMD Millipore, Burlington, Mass.) and allowed to react with the DM1-PEG$_6$-NHS for 3-20 h at ambient temperature. In all reactions the amount of DMSO was kept at <3%. The excess unconjugated drug linker was removed from the reaction mixture using centrifugal filters and PBS as a storage buffer. All conjugates were passed through 0.22 μm membrane filters and aliquoted into 20 μL vials. The vials were stored at −80° C. until further use. The DAR was then determined by UV spectrophotometry and bioanalyzer (Mississauga, ON).

For various antibodies described herein including nimotuzumab, immunoconjugates comprising low DAR and immunoconjugates comprising a high DAR were made. For the bispecific antibody, immunoconjugates comprising low DAR were made.

Synthesis of and Conjugation of Bifunctional Chelator Macropa-NCS (6-((16-((6-carboxypyridin-2-yl)methyl)-1,4,10,13-tetraoxa-7,16-diazacyclooctadecan-7-yl)methyl)-4-isothiocyanatopicolinic acid with Antibodies Macropa-N H$_2$ (Cornell University) was converted to 6-((16-((6-carboxypyridin-2-yl)methyl)-1,4,10,13-tetraoxa-7,16-diazacyclooctadecan-7-yl)methyl)-4-isothiocyanatopicolinic acid (12, macropa-SCN) (macropa-SCN) by modified protocol based on the protocol in Thiele et al, 2017 (46). A white suspension of macropa-NH$_2$ (116 mg, 0.211 mmol) and Na$_2$CO$_3$ (0.2540 g, 3.2 mmol) was heated at reflux in acetone (10 mL) for 30 min before the slow addition of CSCl2 (200 μL). The resulting orange suspension was heated at reflux for 8 h and then concentrated at 30° C. under reduced pressure to a pale-orange solid. The crude product was dissolved in ethyl acetate and washed with water and then finally with brine. The organic layer was dried over sodium sulfate, and the solvent was removed under reduced pressure to get a crude product that was purified by column chromatography on silica gel using chloroform: methanol (8:2). $^1$H NMR (400 MHz, DMSO-d6) δ=8.19-8.04 (m, 2H), 8.02 (br s, 1H), 7.86 (d, J=1.5 Hz, 1H), 7.83 (d, J=7.16 Hz, 1H), 4.73 (s, 2H), 4.66 (s, 2H), 3.91-3.78 (m, 8H), 3.60-3.45 (m, 16H). HRMS (m/z): 590.22600 [M+H]$^+$; Calc: 590.22791.

Conjugation of Macropa Chelator with Antibodies:

Target antibody (e.g. nimotuzumab, pertuzumab, trastuzumab, ritxumab bispecific anti-EphA2 antibody, cixutumumab, 8709-scFv-Fc) and control antibody (MBP IgG) were conjugated with macropa-NCS using a protocol which was optimized for pH, buffer, time and temperature. A stock of 20 mg/mL of macropa-NCS was used for conjugation reactions. Briefly, 1 mg each of the above antibodies were buffer exchanged with 0.1M sodium bicarbonate buffer containing 0.15M sodium chloride using a spin cap column. After buffer exchange, the desired volume of macropa-NCS was added to each antibody solution and incubated at 4° C. for 18 h. Following incubation, macropa conjugated antibody was purified using spin cap column by centrifuging at 12,000 rpm for 5 mins. PBS was used for purification, and the washing step was repeated 8-10 times. After purification, the immunoconjugates were passed through a 0.2 μM membrane filter to prevent bacterial contamination. The concentration was checked using nanodrop, and the samples were aliquoted and stored at −80° C.

Conjugation of Antibody and Antibody Drug Conjugates with p-SCN-Bz-DOTA

A stock solution of 5 mg/mL of target antibody (e.g. nimotuzumab, nimotuzumab-PEG$_6$-DM1-Low or nimotuzumab-PEG$_6$-DM1-High) in PBS was buffer exchanged to 0.1 M NaHCO$_3$ (pH 8.5) using centrifugal filters (Amicon Ultra-4 Centrifugal Filter 30K NMCO, EMD Millipore). A 25-fold excess of p-SCN-Bz-DOTA (20 mg/mL in DMSO) was added to the target antibody (e.g. nimotuzumab, nimotuzumab-PEG$_6$-DM1-Low or nimotuzumab-PEG$_6$-DM1-High and allowed to react at 37° C. on a shaker at 500 rpm for one hour. After the reaction, excess DOTA was removed using Amicon Ultra-4 Centrifugal Filter (30K cut-off, EMD Millipore) with PBS. The DOTA derivatized immunoconjugates were purified by passing through 0.2 μm hydrophilic PTFE membrane filters (Ultrafree®-CL Centrifugal filters, Millipore). Aliquots of 20 μL were prepared and stored at −80° C. The quantification of the protein concentration was done by SmartSpec Plus spectrophotometer (Bio-Rad).

Radiolabeling with $^{225}$Ac and $^{89}$Zr

Radiolabeling of macropa conjugates with $^{225}$Ac was performed as described by Thiele et al, 2017 (46). In brief, 1 MBq of $^{225}$Ac (CNL, Chalk River, Canada or Oakridge) was incubated with 1.6 mg of Macropa-target antibody (e.g. macropa-nimotuzumab, macropa-pertuzumab, macropa-trastuzumab, macropa-ritxumab macropa-bispecific anti-EphA2-low antibody, macropa-cixutumumab and macropa-8709-scFv-Fc as well as PEG$_6$-DM1 conjugates of each of the foregoing), or macropa-control IgG in 0.15 M ammonium acetate (pH 6.0) at room temperature for 30-60 min. The reaction was monitored using iTLC with 100 mM sodium citrate buffer (pH 5.0) as mobile phase. ITLC strips were measured using ScanRam (LabLogic, Brandon, Fla.). After incubation, the $^{225}$Ac-labeled conjugates were purified using 10 K cut-off Amicon Ultra-4 centrifugal filters with PBS. The purity of the radiolabeled immunoconjugates was determined using size exclusion radio-HPLC and iTLC as described earlier (46, 51). DFO-8709-scFv-Fc was radiolabeled with $^{89}$Zr using a protocol described in Chekol et al, 2018 (51).

Radiolabelling of DOTA Conjugates with $^{225}$Ac

In a typical 1-step procedure, $^{225}$Ac-nitrate (1.0 MBq) dissolved in 0.05 M HCl (Optima grade, Fisher scientific) was added to a 1.5 mL microtube, and the activity was determined exactly using a dose calibrator. To this were added, L-ascorbic acid (150 g/L; 10 μL), 150 mM ammonium acetate (pH 6.0, 25 μL), and DOTA-antibody (e.g. cixutumumab)-PEG$_6$-DM1 (125 μg, specific activity 8 kBq/μg). The pH of the reaction was determined by spotting 1 μL of the reaction mixture onto Hydrion pH paper (range, 5.0-9.0) (Sigma-Aldrich); pH of a typical reaction was 5.8. The reaction mixture was incubated at 37° C. on a shaker at 650 RPM for 2 h. After this, a small aliquot (0.5 μL) was spotted on an iTLC strip, to determine the extent of incorporation of actinium onto protein by using mobile phase of 50 mM sodium citrate (pH 5.2). Purification of the $^{225}$Ac-cixutumumab-PEG$_6$-DM1 was purified using Amicon Ultra-4 centrifugal filters (10K, EMD Millipore, Burlington, Mass.) with PBS.

Exemplary schemes and additional details are provided in Examples 7 and 8.

Characterization of Immunoconjugates and Components Thereof

Quality Control of Immunoconjugates

Quality control was done on samples of target and control antibodies and conjugates thereof including nimotuzumab, 8709-scFv-Fc, pertuzumab, trastuzumab, ritxumab bispecific anti-EphA2 antibody, cixutumumab, nimotuzumab-$PEG_6$-DM1, 8709-scFv-Fc-$PEG_6$-DM1, pertuzumab-$PEG_6$-DM1, trastuzumab-$PEG_6$-DM1, ritxumab-$PEG_6$-DM1, bispecific anti-EphA2-$PEG_6$-DM1-low, control Ab-$PEG_6$-DM1-low, cixutumumab-$PEG_6$-DM1, control IgG-$PEG_6$-DM1, macropa-nimotuzumab, macropa-8709-scFv-Fc, macropa-anti-EphA2, macropa-anti-EphA2-$PEG_6$-DM1-low, macropa-control Ab and macropa-control Ab-$PEG_6$-DM1-low. Size exclusion HPLC (SEC-HPLC) using Waters 2796 Bioseparations Module, Waters 2487 Dual λ Absorbance Detector, XBridge® BEH 200A SEC 3.5 μm 7.8×300 mm column (Waters Corporation, Milford, Mass.) was used to determine the integrity of immunoconjugates, ADCs and amount free $PEG_6$-DM1. The UV-Detector was set at 254 and 280 nm with PBS as the solvent and a flow rate of 0.6 mL/min. The size and purity of the immunoconjugates was characterized by electronic electrophoresis (bioanalyzer). The analysis of molecular weight and purity of all the conjugated samples were performed on an Agilent 2100 Bioanalyzer system using Agilent High Sensitivity Protein 250 Kit (cat #5067-1575) according to the manufacturer's protocol.

Flow Cytometry

In vitro binding to target receptor (e.g. EGFR) positive cells was performed for all immunoconjugates and compared with corresponding unconjugated antibody, and control IgG. For example, for EGFR positive cells, in vitro binding of anti-EGFR immunoconjugates to EGFR positive cells was compared to unconjugated nimotuzumab, 8709-ScFv-Fc or control IgG. Human breast cancer cells (depending on the experiment, MDA-MB-231, MCF-7 MDA-MB-468 and MDA-MB-435) were collected, washed and resuspended in PBS containing 2% FBS. Target antibodies, control IgG and their respective ADCs were titrated at a minimum of a 10-fold excess onto $1 \times 10^5$ cells. The cell-compound reactions were incubated for 30 minutes at room temperature followed by 15 minutes on ice. Cells were washed and resuspended in a 1:50 dilution of PE or FITC labeled Goat F(ab')2 fragment anti-human IgG (H+L) antibody (Beckman Coulter, IM0839) and incubated for 30 minutes on ice in the dark. Cells were washed and suspended in 2% FBS-PBS. Data was acquired using a Beckman Coulter Gallios flow cytometer and the results were analysed using FlowJoV10. The binding constant $K_D$ for each conjugate were generated using a non-linear regression curve fit with GraphPad prism 6.

Radioligand Binding, Internalization and Immunoreactivity

A saturation radioligand binding assay was performed to determine by incubating 0.5 million cells with increasing concentrations of radioimmunoconjugates (0.2-95 nmol/L in 100 μL PBS) for 4 h at 4° C. Non-specific binding (NSB) was determined in a similar assay but in the presence of a 50-fold molar excess of unlabeled antibody (relative to the highest concentration of the radioimmunoconjugates). A non-linear regression analysis with one-site binding equation was used to determine $K_D$ using GraphPad Prism 6.

Internalization of the non-radiolabeled immunoconjugates and radioimmunoconjugates was performed using an IncuCyte S3 Live cell imaging system (Essen BioScience, Ann Arbor, Mich.). In brief, 5000 cells were plated per well in a 96 well plate. Radiolabeled and non-radiolabeled immunoconjugates were mixed with Incucyte Human FabFluor pH Red antibody labeling reagent (Cat No: 4722) and incubated for 10-20 mins in the dark at room temperature. After incubation, the immunoconjugates mixed with internalization reagent were added to cells and incubated for 30 mins prior to imaging. Live cell images were captured every 2 h using a 10× objective lens using phase contrast and fluorescence channel. Internalization of unlabeled antibodies and immunoconjugates was performed at a fixed concentration (250 nM). During each scanning 5 images were acquired until the end of the experiment. All cell images were processed and analysed using IncuCyte S3 software. The immunoreactive fraction of the radioimmunoconjugate was determined as described in Lindmo et al, 1986 (52).

The binding of $^{225}$Ac-8709-scFv-Fc to EGFR was determined in MDA-MB-468 cells.

The binding of $^{225}$Ac-bispecific anti-EphA2 and $^{225}$Ac-bispecific anti-EphA2-$PEG_6$-DM1-Low to EphA2 was studied in MDA-MB-231 cells.

In Vitro Cytotoxicity

In vitro cytotoxicity of naked antibodies, immunoconjugates and radioimmunoconjugates and control IgG was tested in various cancer cell lines.

For example, 8709-scFv-Fc, nimotuzumab, control IgG, 8709-scFv-Fc-$PEG_6$-DM1, nimotuzumab-$PEG_6$-DM1, control IgG-$PEG_6$-DM1, 8709-scFv-Fc-$PEG_6$-DM1+nimotuzumab-$PEG_6$-DM1, $^{225}$Ac-8709-scFv-Fc, $^{225}$Ac-control IgG, $^{225}$Ac-8709-scFv-Fc+nimotuzumab-$PEG_6$-DM1, $^{225}$Ac-control IgG+control IgG-$PEG_6$-DM1 samples was studied in MDA-MB-231, MDA-MB-468 and TrR-1 cells using IncuCyte S3 Live cell imaging system. The number of EGFR/cell in these cell lines is in MDA-MB-648>MDA-MB-231>TrR-1 (53).

In other examples, bispecific anti-EphA2, bispecific anti-EphA2-$PEG_6$-DM1-Low, Control-Ab, Control-Ab-$PEG_6$-DM1-Low, $^{225}$Ac-bispecific anti-EphA2, $^{225}$Ac-bispecific anti-EphA2-$PEG_6$-DM1-Low, $^{225}$Ac-Control-Ab and $^{225}$Ac-Control-Ab-$PEG_6$-DM1-Low samples was studied in MDA-MB-231 cells using IncuCyte S3 Live cell imaging system (Essen BioScience, Ann Arbor, Mich.).

IGF-1R was tested in cell lines including SUM141-PT, MCF7-R18 and MCF (control) and xenographs.

Briefly, 20,000 cells were seeded 24 h prior to treatment in a 96 well clear bottom corning pre-coated with Poly-D-lysine plates. The next day, the media was removed and washed with PBS. Cells were then incubated with IncuCyte® Cytotox Red reagent diluted in complete media (1× Essen Bioscience Cat #4632) for 3 h before treatment. Cells were treated with different concentrations (3.5-500 nM) of non radiolabeled immunoconjugates and (0.01-2 nCi) for radiolabeled samples and incubated at 37° C. for 30 min prior to scanning. Live cell images were captured every 2 h using a 10× objective lens using phase contrast and fluorescence channel. During each scanning 5 images were acquired until the end of the experiment. All cell images were processed and analysed using IncuCyte S3 software. Relative fluorescent values were generated and $EC_{50}$ values for individual compounds were calculated using GraphPad prism 6.

In Vitro Domain/Epitope Specific Binding

EGFR

EGFR domain II binding of $^{225}$Ac-8709-scFv-Fc was determined by incubating the radioimmunoconjugate with or without a 100-fold excess of unlabeled 8709-scFv-Fc or domain III-binding antibody nimotuzumab. The binding assay was performed in triplicates with $2 \times 10^6$ cells/mL using different concentrations of $^{225}$Ac-8709-scFv-Fc (50, 5 and 0.5 nM). Specific binding was determined by incubating $^{225}$Ac-8709-scFv-Fc with a 100-fold excess of unlabeled 8709-scFv-Fc while non-specific binding to domain III was determined by pre-incubating EGFR-positive MDA-MB-468 cells with a 100-fold excess of nimotuzumab (domain III specific) prior to incubation with $^{225}$Ac-8709-scFv-Fc. The tubes containing the cells were incubated for 1 h at 4° C. After incubation, cell pellets were separated from the supernatants by centrifugation at 1200×g for 2 min, followed by washing three times with 1×PBS. The tubes with the pellets and supernatant were separately counted in a gamma counter (Perkin Elmer, Brea, Calif.) to determine the amount of activity bound to pellets (cells). Data was presented as counts per second (CPM) of bound activity versus concentration.

HER2

HER2 domain II binding of $^{225}$Ac-Pertuzumab-PEG6-DM1 or domain IV binding of 225Ac-trastuzumab-PEG$_6$-DM1 was determined using a corresponding assay as described above for EGFR. JIMT-1, SKBR3, MG63, 147D cell lines were used.

In Vivo Domain I/II Imaging Using $^{89}$Zr Conjugated Antibodies $^{89}$Zr-8709-scFv-Fc In vivo evaluation of domain I/II specificity of $^{89}$Zr-8709-scFv-Fc was studied in mice bearing EGFR positive MDA-MB-468 or EGFR negative MDA-MB-435 tumor. MDA-MB-468 tumor bearing mice (n=3) were injected via a tail vein with 9.02±0.2 MBq (18 ug) of $^{89}$Zr-8709-scFv-Fc followed my microPET/CT imaging at 24 h, 48 h and 120 h post injection (p.i.). To show that domain III binder nimotuzumab did not bind to the same epitope as 8709-ScFv-Fc in vivo, a second group of mice was injected with a therapeutic dose (300 μg, 15 mg/kg) of nimotuzumab prior to administration of $^{89}$Zr-8709-scFv-Fc. Mice were imaged using the same imaging protocol as for the other groups. In the control group, mice with MDA-MB-435 tumors were injected with $^{89}$Zr-8709-scFv-Fc followed by microPET/CT imaging. MicroPET/CT images were acquired using Vector4CT scanner (MILabs, Utrecht). The imaging and reconstruction parameters, and animal care during imaging. For quantification, CT and PET images were analysed using PMOD 3.8 biomedical image analysis software (PMOD, Switzerland). A 3D region-of-interest (ROI) was manually drawn to encompass the radioactivity uptake in the organ of interest. Tracer uptake was expressed as % IA/mL of tissue volume (% IA/cc). The result was reported as mean±standard deviation within each study group.

In Vivo Efficacy of (Radio)Immunoconjugates

In vivo therapy studies were done in CD-1 nude mice (Charles River Laboratories, Hartford, Conn.), aged 4-6 weeks. Mice were obtained and housed in accordance with University Animal Care Committee (UACC) guidelines (protocol #20179984). All the experiments and euthanasia were performed in accordance with UACC guidelines.

EGFR Domain I/II and Domain III Targeting

To establish MDA-MB-468 xenograft, 10×10$^6$ cells MDA-MB-468 cells were collected and washed with growth media without FBS. Cells were suspended in 50 μL of growth media without FBS plus 50 μL of matrigel membrane matrix (Corning, Corning N.Y.). Cells were injected subcutaneously into the right hind flank of the mouse and tumor volume was monitored every other day until it reached 75-100 mm$^3$ for therapy experiments.

Mice were then divided into 5 groups (n=7/group) namely; $^{225}$Ac-8709-scFv-Fc (450 nCi 1 mg/kg), $^{225}$Ac-8709-scFv-Fc (450 nCi 1 mg/kg)+nimotuzumab-PEG$_6$-DM1 (15 mg/kg), $^{225}$Ac-control IgG (450 nCi 1 mg/kg), $^{225}$Ac-control IgG (450 nCi 1 mg/kg)+control IgG-PEG$_6$-DM1 (15 mg/kg), and PBS. Mice received two doses of treatment via a tail vein on day 0 and day 15. Tumor growth was monitored by measuring the greatest length and width using a digital caliper (tumor volume=length×width$^2$/2). The study was terminated when xenograft reached a volume ≥1500 mm$^3$ and this was used to determine survival in the different groups using Kaplan Meier curves. Individual body weight of mouse was recorded during the quarantine (every other day) and experimental period.

HER2 Domain II and Domain III Targeting

The method described for EGFR was used for HER2 domain II and IV targeting with the following modifications. Various combinations of $^{225}$Ac-Pertuzumab-PEG6-DM1, $^{225}$Ac-trastuzumab-PEG$_6$-DM1 and trastuzumab-PEG$_6$-DM1 and Pertuzumab-PEG6-DM1 were tested for internalization, cytotoxicity and therapeutic application in mice bearing HER2 positive xenografts using methods as described herein.

EphA2 Targeting

Mice were divided into 9 groups, Group 1: $^{225}$Ac-anti-EphA2, Group 2: $^{225}$Ac-anti-EphA2-PEG$_6$-DM1-Low, Group 3: $^{225}$Ac-Control Ab, Group 4: $^{225}$Ac-Control-Ab-PEG$_6$-DM1-Low, Group 5: anti-EphA2, Group 6: anti-EphA2-PEG$_6$-DM1-Low, Group 7: Control Ab, Group 8: Control Ab-PEG$_6$-DM1-Low, Group 9: PBS each group containing 7 mice. For xenograft preparation, 10×10$^6$ cells MDA-MB-231 were collected and washed with growth media without FBS. Cells were suspended in 100 μL of growth media without FBS and injected subcutaneously into the right hind flank of the mouse. Tumour size was monitored weekly until they reached 75-100 mm$^3$. For therapy studies, mice were then intravenously injected through the tail vein with 3 doses (300 nci/dose) of radiolabelled immunoconjugates given at an interval of 10 days. Mice belonging to group 5-8 were given 20 ug (1 mg/kg of mice) of non-radiolabelled anti-EphA2, anti-EphA2-PEG$_6$-DM1-Low, Control-Ab and Control-Ab-PEG$_6$-DM1-Low respectively. All the mice were monitored for a span of 90 days.

IGF-1R

Mice bearing IGF-1R positive SUM149-PT and MCR-7-HER18 xenografts were used for the study. When xenografts average size measured 100-150 mm$^3$ in volume, mice were randomized into different groups (n=≤8 per group). Each mouse received normal saline or 2 doses of 50 μg/mouse (~2.5 mg/kg) of cixutumumab-PEG$_6$-DM1-Low, $^{225}$Ac-cixutumumab (~2.5 mg/kg), $^{225}$Ac-cixutumumab-PEG6-DM1-Low (~2.5 mg/kg) and a PBS control group with $^{225}$Ac-control-IgG-PEG$_6$-DM1 (~2.5 mg/kg) via a tail vein on day 0, and 14. The tumor growth was monitored by measuring the greatest length and the greatest width from each tumor using an external caliper. Then tumor volume was calculated using the formula: tumor volume=length× width$^2$/2. The study was terminated when xenograft reached a volume ≥2000 mm$^3$ and this was used to determine survival in the different groups using Kaplan Meier curves. Individual body weight of mouse was recorded during the quarantine period (every other day) and experimental period.

Biodistribution Studies

All animal studies were approved by the University of Saskatchewan Animal Care and Use Committee in accordance with the guidelines set forth in Use of Laboratory Animals. The mice were housed under standard conditions in approved facilities with 12-h light/dark cycles and given food and water and libitum throughout the duration of the studies. Female nude mice were purchased from the Charles River Laboratory (Sonneville, QC). For inoculation in mice, MDA-MB-231 cells were resuspended at $1 \times 10^7$ cells/mL in growth media without FBS. Each mouse was injected in the right flank with 0.20 mL of the cell suspension. The mice were used for tissue distribution studies when the tumors reached at least 100 mm$^3$.

Purified $^{225}$Ac-anti-EphA2, $^{225}$Ac-anti-EphA2-PEG$_6$-DM1-Low, $^{225}$Ac-Control-Ab and $^{225}$Ac-Control-Ab-PEG$_6$-DM1-Low was passed through 0.22 mm Ultrafree MC filter and 650nCi (specific activity of 0.8 kBq/mg) was injected via tail vein to female CD-1 athymic nude mice bearing an MDA-MB-231 tumor. Groups of mice (n=3 per group) were anaesthetized using isoflurane and sacrificed at 24 and 168 h post injection. The mean percentage injected activity per gram organ weight (% IA/g) was then calculated for all the organs.

Statistical Analysis

All data was expressed as the mean±SD or SEM of at least 3 independent experiments. Statistical comparisons between the experimental groups were performed by 1-way ANOVA with Bonferoni multiple comparison post hoc test (multiple-group comparison). Survival was described as median, and survival curves were compared with the log-rank (Mantel-Cox) test. Graphs were prepared and p values calculated by using GraphPad Prism (version 5.03; GraphPad, La Jolla, Calif.). P values of less than 0.5 were considered significant.

Example 7

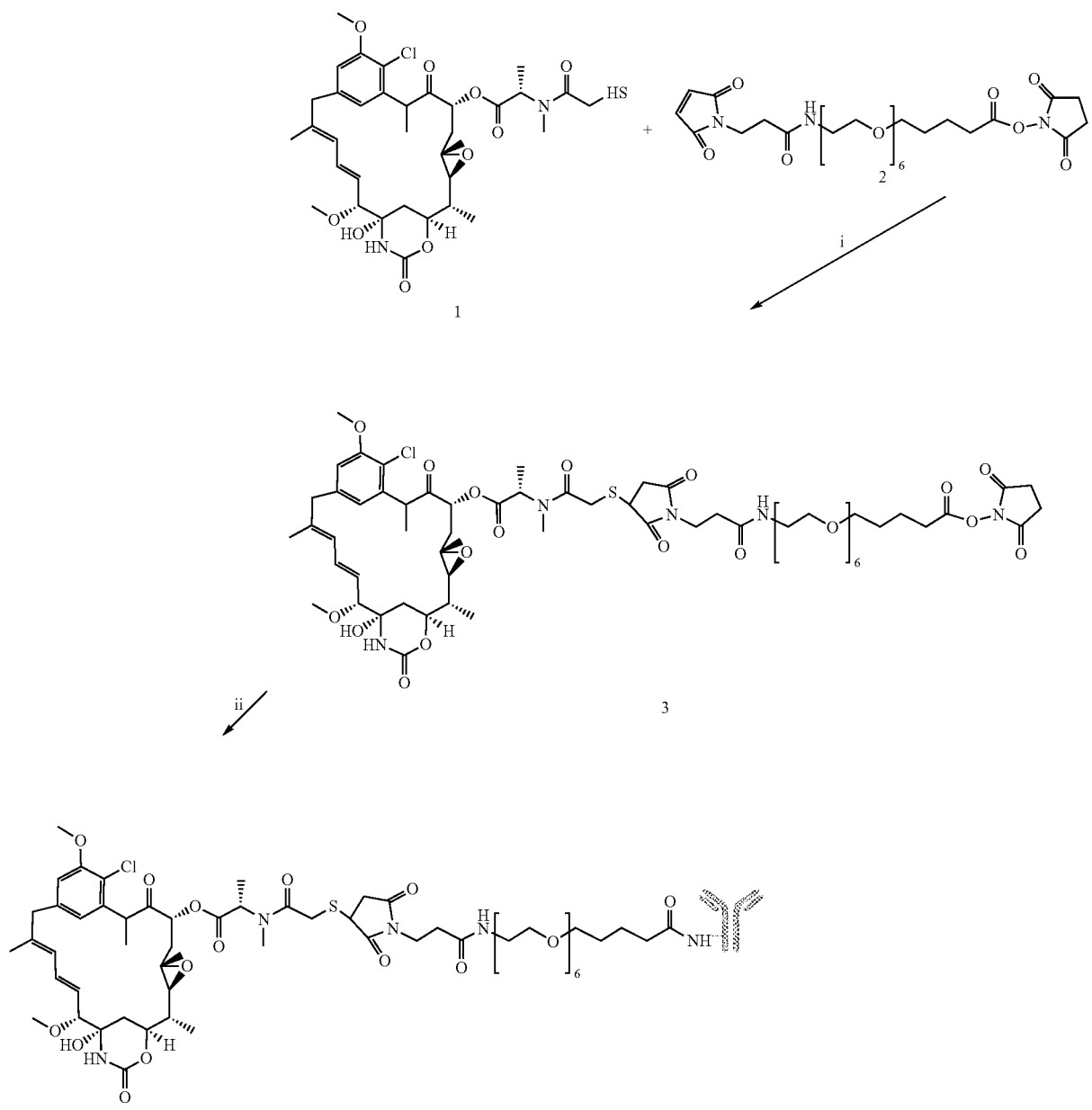

Scheme 1: Maytansine (1) (DM1) is reacted with bifunctional linker NHS-PEG$_6$-Mal (2) in 50 mM PBS/THF for 6 h at room temperature to generate the NHS-PEG$_6$-DM1. The NHS-PEG$_6$-DM1 was analyzed by mass spectrometry and NMR. Different fold excess of NHS-PEG$_6$-DM1 was reacted with antibody in 0.1 M HEPES pH 8.5 at room temperature for 3 h followed by 4° C. for 20 h to yield antibody-PEG$_6$-DM1-Low (3-4 drugs per antibody) or antibody-PEG$_6$-DM1-High (7-8 drugs per antibody).

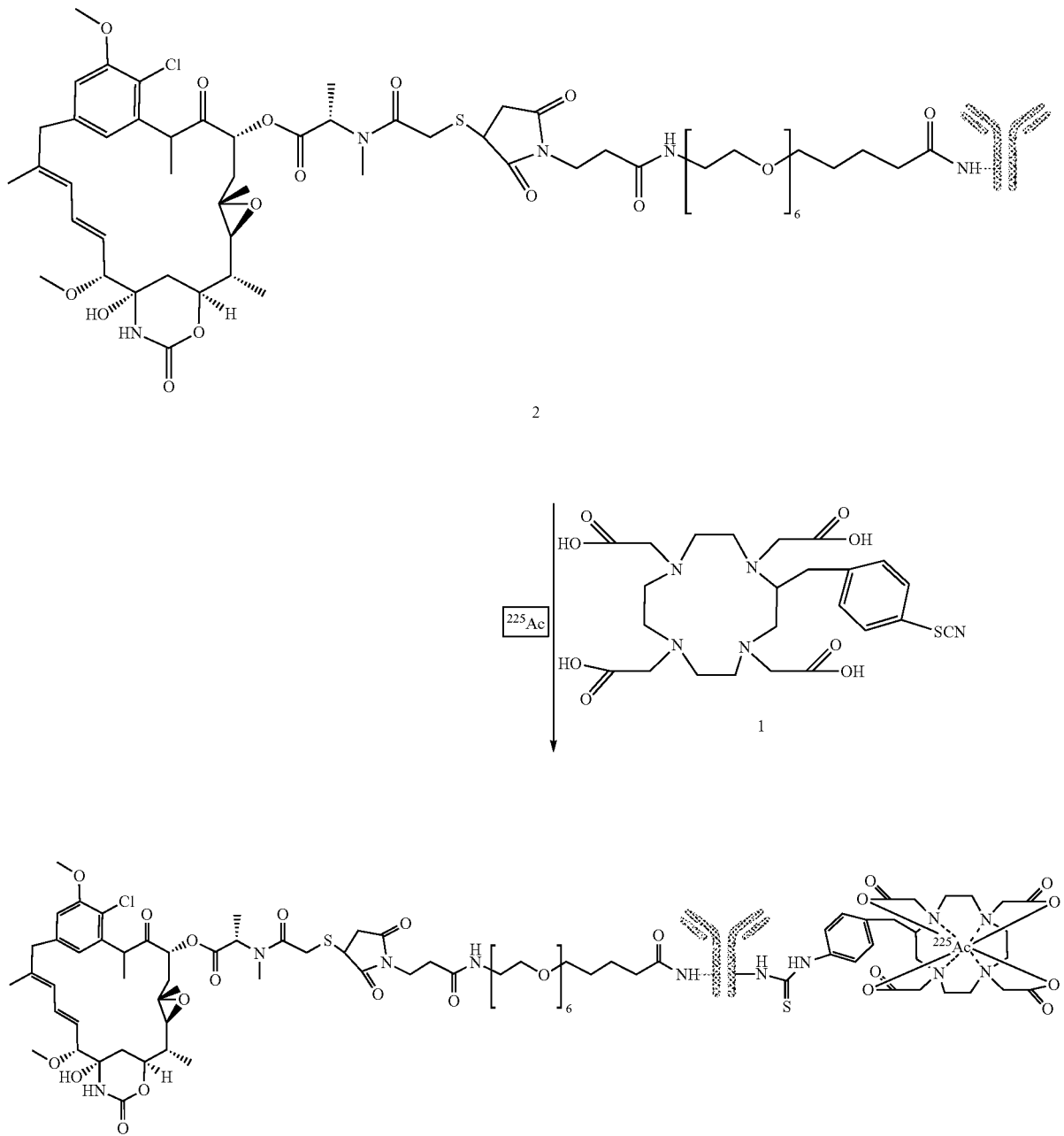

Scheme 2: antibody-PEG$_6$-DM1-Low/High was reacted with excess p-Bn-SCN-DOTA chelator in bicarbonate buffer, pH 8.5 followed by purification and quality control. The DOTA conjugated antibody-PEG$_6$-DM1-Low/High was then radiolabeled with $^{225}$Ac or $^{111}$In to obtain $^{225}$Ac-antibody-PEG$_6$-DM1-Low/High or $^{111}$In-antibody-PEG$_6$-DM1-Low/High. In a similar manner antibody was reacted with DOTA followed by radiolabeling to obtain $^{225}$Ac-antibody or $^{111}$In-antibody.

Example 8

Synthesis of Antibody Drug Conjugates and Radiolabeling of the Immunoconjugates

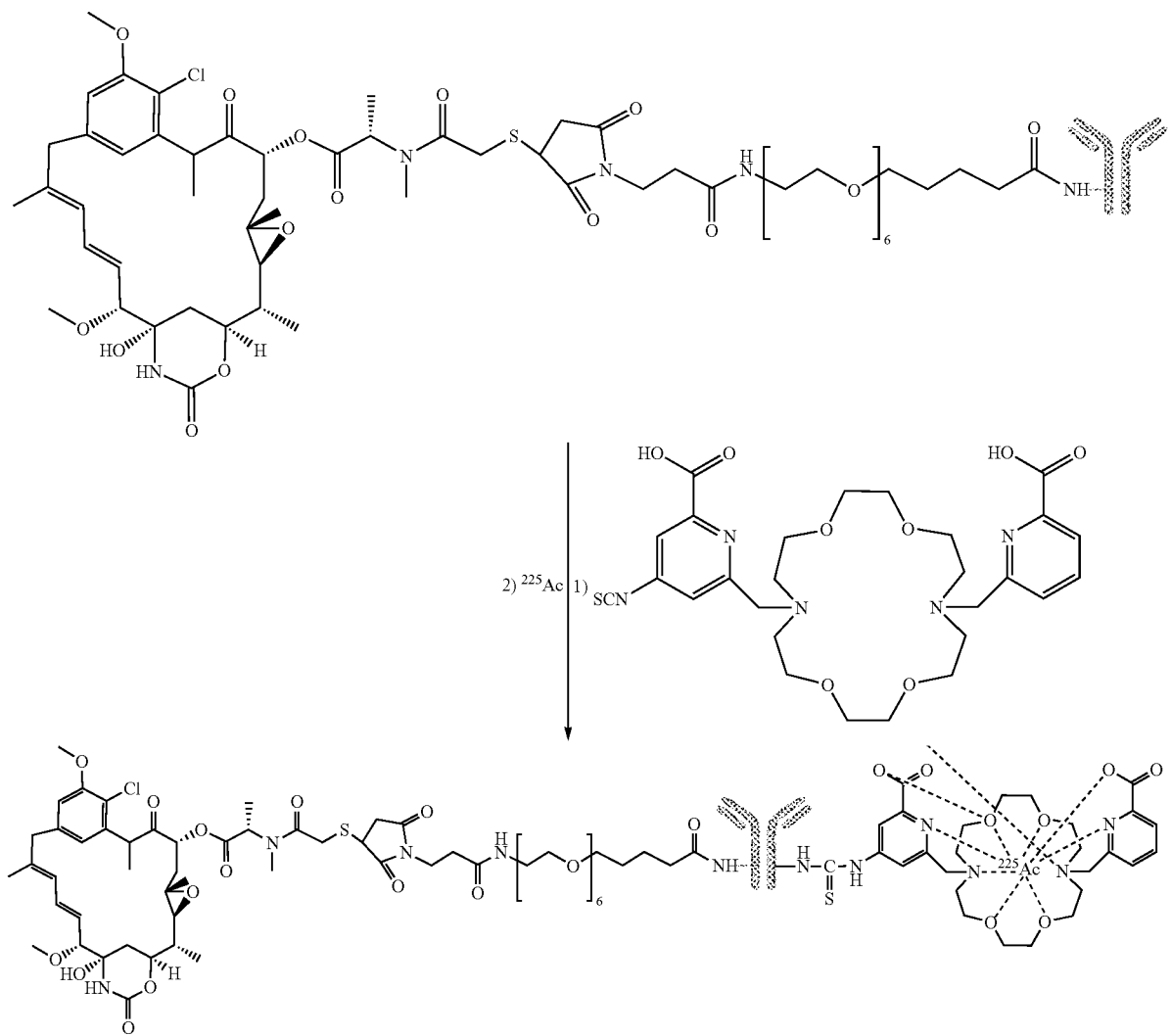

Scheme: Conjugation of macropa to antibody-cytotoxin conjugate and radiolabeling with 225Ac.

Synthesis of Bifunctional Chelator Macropa-NCS (6-((16-(((6-carboxypyridin-2-yl)methyl)-1,4,10,13-tetraoxa-7,16-diazacyclooctadecan-7-yl)methyl)-4-isothiocyanatopicolinic acid Macropa-NCS was synthesized as reported by Thiele et al, 2017 (46). The NMR spectra of the final product: $^1$H NMR (400 MHz, DMSO-d6) δ=8.19-8.04 (m, 2H), 8.02 (br s, 1H), 7.86 (d, J=1.5 Hz, 1H), 7.83 (d, J=7.16 Hz, 1H), 4.73 (s, 2H), 4.66 (s, 2H), 3.91-3.78 (m, 8H), 3.60-3.45 (m, 16H). HRMS (m/z): 590.22600 [M+H]$^+$; Calc: 590.22791.2.5

Conjugation of Macropa Chelator with Antibodies:

Bispecific anti-EphA2 and control antibody were conjugated with macropa-NCS using a protocol which was optimized for pH, buffer, time and temperature. A stock of 20 mg/mL of macropa-NCS was used for conjugation reactions. Briefly, 1 mg each of the above antibodies were buffer exchanged with 0.1M sodium bicarbonate buffer containing 0.15 M sodium chloride using a spin cap column. After buffer exchange, the desired volume of macropa-NCS was added to each antibody solution and incubated at 4° C. for 18 h. Following incubation, macropa conjugated antibody was purified using spin cap column by centrifuging at 12,000 rpm for 5 mins. PBS was used for purification, and the washing step was repeated 8-10 times. After purification, the immunoconjugates were passed through a 0.2 μM membrane filter to prevent bacterial contamination. The concentration was checked using nanodrop, and the samples were aliquoted and stored at −80° C.

Radiolabeling of Immunoconjugates with $^{225}$Ac

Radiolabeling of Macropa conjugates with $^{225}$Ac was performed as per the protocol described by Thiele et al 2017 (46). In brief, 1 MBq of $^{225}$Ac (Oakridge) was reacted with 1.6 mg of Macropa-Bispecific anti-EphA2, Macropa-Bispecific anti-EphA2PEG$_6$-DM1-Low, Macropa-Control-Ab, and Macropa-Control-Ab-PEG$_6$-DM1-Low in 0.15 M ammonium acetate (pH 6.0) at room temperature for 30-60 min. The reaction was monitored using ITLC with 100 mM sodium citrate buffer (pH 5.0) as mobile phase. ITLC strips were measured using ScanRam (LabLogic, Brandon, Fla.). After incubation, the $^{225}$Ac-labeled conjugates were purified using Amicon Ultra-4 centrifugal filters (10K, EMD Millipore, Burlington, Mass.) with PBS. The purity of the radiolabelled immunoconjugates was determined using size exclusion radio-HPLC and iTLC as described earlier.

Example 9

Stability and Specific Activity

Improved stability of the antibody cytotoxin radioisotope complex, radiochemistry and specific activity (defined for example as MBq/mmol of antibody; MBq/microgram of antibody; mCi/mmol of antibody; mCi/microgram of antibody) was obtained when the cytotoxin was coupled to the antibody prior to addition of the chelator and the radionuclide.

Stability can be measured by the % of radionuclide loss from the antibody complex following radiolabelling. When the cytotoxin was coupled to the antibody prior to addition of the chelator and the radionuclide, the complex less than 8% of the radionuclide was lost (ie., the complex was >=92% stable) at 7 days post preparation. In contrast, when the cytotoxin was coupled to the antibody after the addition of the chelator and the radionuclide, a rapid degradation of the complex was observed with more than 50% of the radionuclide at 48 hours post preparation. This demetallation can result in non-specific toxicity and poor tumor targeting.

When the cytotoxin was coupled to the antibody prior to addition of the chelator and the radionuclide, the specific activity of the antibody cytotoxin radioisotope complex with=95% purity was up to 6 kBq/microgram for the $^{225}$Ac, and 0.5-1 MBq/microgram for beta and gamma emitters, as measured 1-3 days after preparation of the cytotoxic agent. In contrast, when the cytotoxin was coupled to the antibody after the addition of the chelator and the radionuclide, the specific activity of the complex quickly decreased to half of these values.

Example 10

Cetuximab Conjugates

Cetuximab is linked to DM1 and radiolabeled with actininum-225 in accordance with the methods set out in Examples 6-8. Cetuximab comprising both cytotoxin and radionuclide shows internalization and cytotoxicity compared to Cetuximab comprising cytotoxin or radionuclide alone and demonstrates a significant synergistic advantage of the combination.

Anti-HER2 Conjugates

Trastuzumab and pertuzumab are linked to DM1 and radiolabeled with actininum-225 in accordance with the methods set out in Examples 6-8. Trastuzumab and pertuzumab comprising both cytotoxin and radionuclide shows internalization and cytotoxicity compared to Trastuzumab and pertuzumab comprising cytotoxin or radionuclide alone and demonstrates a significant synergistic advantage of the combination.

Anti-HER3 Conjugates

Anti-HER3 antibodies including Patritumab, Duligotumab, Seribantumab, HER3-3 and HER3-10 (HER3-3 and HER3-10 are described in PCT/CA2018050965) are linked to DM1 and radiolabeled with actininum-225 in accordance with the methods set out in Examples 6-8. Antibodies comprising both cytotoxin and radionuclide shows internalization and cytotoxicity compared to antibodies comprising cytotoxin or radionuclide alone and demonstrates a significant synergistic advantage of the combination.

REFERENCES

1. Carey L A, Perou C M, Livasy C A, Dressler L G, Cowan D, Conway K, et al. Race, breast cancer subtypes, and survival in the Carolina Breast Cancer Study. JAMA. 2006; 295(21):2492-502.
2. Changavi A A, Shashikala A, Ramji A S. Epidermal Growth Factor Receptor Expression in Triple Negative and Nontriple Negative Breast Carcinomas. J Lab Physicians. 2015; 7(2):79-83.
3. Corkery B, Crown J, Clynes M, O'Donovan N. Epidermal growth factor receptor as a potential therapeutic target in triple-negative breast cancer. Ann Oncol. 2009; 20(5): 862-7.
4. Tanei T, Choi D S, Rodriguez A A, Liang D H, Dobrolecki L, Ghosh M, et al. Antitumor activity of Cetuximab in combination with Ixabepilone on triple negative breast cancer stem cells. Breast Cancer Res. 2016; 18(1):6.
5. Baselga J, Gomez P, Greil R, Braga S, Climent M A, Wardley A M, et al. Randomized phase II study of the anti-epidermal growth factor receptor monoclonal antibody cetuximab with cisplatin versus cisplatin alone in patients with metastatic triple-negative breast cancer. J Clin Oncol. 2013; 31(20):2586-92.
6. Wykosky J, Debinski W. The EphA2 receptor and ephrinA1 ligand in solid tumors: function and therapeutic targeting. Mol Cancer Res. 2008; 6(12):1795-806.
7. Song W, Hwang Y, Youngblood V M, Cook R S, Balko J M, Chen J, et al. Targeting EphA2 impairs cell cycle progression and growth of basal-like/triple-negative breast cancers. Oncogene. 2017; 36(40):5620-30.
8. Sharkey R M, Karacay H, Govindan S V, Goldenberg D M. Combination radioimmunotherapy and chemoimmunotherapy involving different or the same targets improves therapy of human pancreatic carcinoma xenograft models. Mol Cancer Ther. 2011; 10(6):1072-81.
9. Crozier J A, Advani P P, LaPlant B, Hobday T, Jaslowski A J, Moreno-Aspitia A, Perez E A. N0436 (Alliance): A Phase II Trial of Irinotecan With Cetuximab in Patients With Metastatic Breast Cancer Previously Exposed to Anthracycline and/or Taxane-Containing Therapy. Clin Breast Cancer. 2016; 16(1):23-30.
10. Baselga J, Gómez P, Greil R, Braga S, Climent M A, Wardley A M, Kaufman B, Stemmer S M, Pêgo A, Chan A, Goeminne J C, Graas M P, Kennedy M J, Ciruelos Gil E M, Schneeweiss A, Zubel A, Groos J, Melezínková H, Awada A. Randomized phase II study of the anti-epidermal growth factor receptor monoclonal antibody cetuximab with cisplatin versus cisplatin alone in patients with metastatic triple-negative breast cancer. J Clin Oncol. 2013; 31(20):2586-92.
11. Parker C, Nilsson S, Heinrich D, Helle S I, O'Sullivan J M, Fossa S D, et al. Alpha emitter radium-223 and survival in metastatic prostate cancer. N Engl J Med. 2013; 369(3):213-23.
12. Kratochwil C, Bruchertseifer F, Giesel F L, Weis M, Verburg F A, Mottaghy F, et al. 225Ac-PSMA-617 for PSMA-Targeted alpha-Radiation Therapy of Metastatic Castration-Resistant Prostate Cancer. J Nucl Med. 2016; 57(12):1941-4.
13. Meredith R, Torgue J, Shen S, Fisher D R, Banaga E, Bunch P, et al. Dose escalation and dosimetry of first-in-human alpha radioimmunotherapy with 212Pb-TCMC-trastuzumab. J Nucl Med. 2014; 55(10):1636-42.

14. Robinson D R, Wu Y M, Lin S F: The protein tyrosine kinase family of the human genome. Oncogene 2000, 19(49):5548-5557.
15. Chung C H, Ely K, McGavran L, Varella-Garcia M, Parker J, Parker N, Jarrett C, Carter J, Murphy B A, Netterville J et al: Increased epidermal growth factor receptor gene copy number is associated with poor prognosis in head and neck squamous cell carcinomas. Journal of clinical oncology: official journal of the American Society of Clinical Oncology 2006, 24(25):4170-4176.
16. Alshenawy H A: Immunohistochemical expression of epidermal growth factor receptor, E-cadherin, and matrix metalloproteinase-9 in ovarian epithelial cancer and relation to patient deaths. Annals of diagnostic pathology 2010, 14(6):387-395.
17. Cunningham D, Humblet Y, Siena S, Khayat D, Bleiberg H, Santoro A, Bets D, Mueser M, Harstrick A, Verslype C et al: Cetuximab monotherapy and cetuximab plus irinotecan in irinotecan-refractory metastatic colorectal cancer. The New England journal of medicine 2004, 351(4):337-345.
18. Giltnane J M, Ryden L, Cregger M, Bendahl P O, Jirstrom K, Rimm D L: Quantitative measurement of epidermal growth factor receptor is a negative predictive factor for tamoxifen response in hormone receptor positive premenopausal breast cancer. Journal of clinical oncology: official journal of the American Society of Clinical Oncology 2007, 25(21):3007-3014.
19. Bellone S, Frera G, Landolfi G, Romani C, Bandiera E, Tognon G, Roman J J, Burnett A F, Pecorelli S, Santin A D: Overexpression of epidermal growth factor type-1 receptor (EGF-R1) in cervical cancer: implications for Cetuximab-mediated therapy in recurrent/metastatic disease. Gynecologic oncology 2007, 106(3):513-520.
20. Siwak D R, Carey M, Hennessy B T, Nguyen C T, McGahren Murray M J, Nolden L, Mills G B: Targeting the epidermal growth factor receptor in epithelial ovarian cancer: current knowledge and future challenges. Journal of oncology 2010, 2010:568938.
21. Bonner J A, Harari P M, Giralt J, Azarnia N, Shin D M, Cohen R B, Jones C U, Sur R, Raben D, Jassem J et al: Radiotherapy plus cetuximab for squamous-cell carcinoma of the head and neck. The New England journal of medicine 2006, 354(6):567-578.
22. Addeo R, Caraglia M, Cerbone D, Frega N, Cimmino G, Abbruzzese A, Del Prete S: Panitumumab: a new frontier of target therapy for the treatment of metastatic colorectal cancer. Expert review of anticancer therapy 2010, 10(4):499-505.
23. Ramos T C, Figueredo J, Catala M, Gonzalez S, Selva J C, Cruz T M, Toledo C, Silva S, Pestano Y, Ramos M et al: Treatment of high-grade glioma patients with the humanized anti-epidermal growth factor receptor (EGFR) antibody h-R3: report from a phase I/II trial. Cancer biology & therapy 2006, 5(4):375-379.
24. Crombet T, Osorio M, Cruz T, Roca C, del Castillo R, Mon R, Iznaga-Escobar N, Figueredo R, Koropatnick J, Renginfo E et al: Use of the humanized anti-epidermal growth factor receptor monoclonal antibody h-R3 in combination with radiotherapy in the treatment of locally advanced head and neck cancer patients. Journal of clinical oncology: official journal of the American Society of Clinical Oncology 2004, 22(9):1646-1654.
25. Patel D, Lahiji A, Patel S, Franklin M, Jimenez X, Hicklin D J, Kang X: Monoclonal antibody cetuximab binds to and down-regulates constitutively activated epidermal growth factor receptor vIII on the cell surface. Anticancer research 2007, 27(5a):3355-3366.
26. Sickmier E A, Kurzeja R J, Michelsen K, Vazir M, Yang E, Tasker A S: The Panitumumab EGFR Complex Reveals a Binding Mechanism That Overcomes Cetuximab Induced Resistance. PloS one 2016, 11(9):e0163366.
27. Keating G M: Panitumumab: a review of its use in metastatic colorectal cancer. Drugs 2010, 70(8):1059-1078.
28. Molinari E, De Quatrebarbes J, Andre T, Aractingi S: Cetuximab-induced acne. Dermatology (Basel, Switzerland) 2005, 211(4):330-333.
29. Lacouture M E: Mechanisms of cutaneous toxicities to EGFR inhibitors. Nature reviews Cancer 2006, 6(10):803-812.
30. Rojo F, Gracias E, Villena N, Cruz T, Corominas J M, Corradino I, Cedeno M, Campas C, Osorio M, Iznaga N et al: Pharmacodynamic trial of nimotuzumab in unresectable squamous cell carcinoma of the head and neck: a SENDO Foundation study. Clinical cancer research: an official journal of the American Association for Cancer Research 2010, 16(8):2474-2482.
31. Miersch S, Maruthachalam B V, Geyer C R, Sidhu S S: Structure-Directed and Tailored Diversity Synthetic Antibody Libraries Yield Novel Anti-EGFR Antagonists. ACS chemical biology 2017, 12(5):1381-1389.
32. Bernhard W, El-Sayed A, Barreto K, Gonzalez C, Fonge H, Geyer C R: Near infrared imaging of epidermal growth factor receptor positive xenografts in mice with domain I/II specific antibody fragments. Theranostics 2019, 9(4):974-985.
33. Nakai K, Hung M C, Yamaguchi H: A perspective on anti-EGFR therapies targeting triple-negative breast cancer. American journal of cancer research 2016, 6(8):1609-1623.
34. Hamblett K J, Kozlosky C J, Siu S, Chang W S, Liu H, Foltz I N, Trueblood E S, Meininger D, Arora T, Twomey B et al: AMG 595, an Anti-EGFRvIII Antibody-Drug Conjugate, Induces Potent Antitumor Activity against EGFRvIII-Expressing Glioblastoma. Molecular cancer therapeutics 2015, 14(7):1614-1624.
35. LoRusso P M, Weiss D, Guardino E, Girish S, Sliwkowski M X: Trastuzumab emtansine: a unique antibody-drug conjugate in development for human epidermal growth factor receptor 2-positive cancer. Clinical cancer research: an official journal of the American Association for Cancer Research 2011, 17(20):6437-6447.
36. Verma S, Miles D, Gianni L, Krop I E, Welslau M, Baselga J, Pegram M, Oh D Y, Dieras V, Guardino E et al: Trastuzumab emtansine for HER2-positive advanced breast cancer. N Engl J Med 2012, 367(19):1783-1791.
37. Holland J P, Sheh Y, Lewis J S: Standardized methods for the production of high specific-activity zirconium-89. Nuclear medicine and biology 2009, 36(7):729-739.
38. Sharma P, Hu-Lieskovan S, Wargo J A, Ribas A: Primary, Adaptive, and Acquired Resistance to Cancer Immunotherapy. Cell 2017, 168(4):707-723.
39. Babina I S, Turner N C: Advances and challenges in targeting FGFR signalling in cancer. Nature reviews Cancer 2017, 17(5):318-332.
40. Ritter C A, Perez-Torres M, Rinehart C, Guix M, Dugger T, Engelman J A, Arteaga C L: Human breast cancer cells selected for resistance to trastuzumab in vivo overexpress epidermal growth factor receptor and ErbB ligands and remain dependent on the ErbB receptor network. Clinical 40. cancer research: an official journal of the American Association for Cancer Research 2007, 13(16):4909-4919.
41. Barok M, Joensuu H, Isola J: Trastuzumab emtansine: mechanisms of action and drug resistance. Breast cancer research: BCR 2014, 16(2):209.
42. Shefet-Carasso L, Benhar I: Antibody-targeted drugs and drug resistance—challenges and solutions. Drug resistance updates: reviews and commentaries in antimicrobial and anticancer chemotherapy 2015, 18:36-46.
43. Kovtun Y V, Audette C A, Mayo M F, Jones G E, Doherty H, Maloney E K, Erickson H K, Sun X, Wilhelm S, Ab O et al: Antibody-maytansinoid conjugates designed to bypass multidrug resistance. Cancer research 2010, 70(6):2528-2537.
44. Zhao R Y, Wilhelm S D, Audette C, Jones G, Leece B A, Lazar A C, Goldmacher V S, Singh R, Kovtun Y, Widdison W C et al: Synthesis and evaluation of hydrophilic linkers for antibody-maytansinoid conjugates. Journal of medicinal chemistry 2011, 54(10):3606-3623.
45. Hartimath S V, El-Sayed A, Makhlouf A, Bernhard W, Gonzalez C, Hill W, Parada A C, Barreto K, Geyer C R, Fonge H: Therapeutic potential of nimotuzumab PEGylated-maytansine antibody drug conjugates against EGFR positive xenograft. Oncotarget 2019, 10(10):1031-1044.
46. Thiele N A, Brown V, Kelly J M, Amor-Coarasa A, Jermilova U, MacMillan S N, Nikolopoulou A, Ponnala S, Ramogida C F, Robertson A K H et al: An Eighteen-Membered Macrocyclic Ligand for Actinium-225 Targeted Alpha Therapy. 2017, 56(46):14712-14717.
47. Erickson H K, Park P U, Widdison W C, Kovtun Y V, Garrett L M, Hoffman K, Lutz R J, Goldmacher V S, Blattler W A: Antibody-maytansinoid conjugates are activated in targeted cancer cells by lysosomal degradation and linker-dependent intracellular processing. Cancer research 2006, 66(8):4426-4433.
48. Hartimath S V, Alizadeh E, Solomon V R, Chekol R, Bernhard W, Hill W, Casaco A P, Barreto K, Geyer C R, Fonge H: Preclinical Evaluation of (111)In-labeled PEGylated Maytansine Nimotuzumab Drug Conjugates in EGFR-positive Cancer Models. J Nucl Med 2019 doi: 10.2967/jnumed.118.220095. [Epub ahead of print].
49. Mazorra Z, Lavastida A, Concha-Benavente F, Valdes A, Srivastava R M, Garcia-Bates T M, Hechavarria E, Gonzalez Z, Gonzalez A, Lugiollo M et al: Nimotuzumab Induces N K Cell Activation, Cytotoxicity, Dendritic Cell Maturation and Expansion of EGFR-Specific T Cells in Head and Neck Cancer Patients. Front Pharmacol 2017, 8:382.
50. Queern S L, Aweda T A, Massicano A V F, Clanton N A, El Sayed R, Sader J A, Zyuzin A, Lapi S E: Production of Zr-89 using sputtered yttrium coin targets (89)Zr using sputtered yttrium coin targets. Nuclear medicine and biology 2017, 50:11-16.
51. Chekol R, Solomon V R, Alizadeh E, Bernhard W, Fisher D, Hill W, Barreto K, DeCoteau J F, Parada A C, Geyer C R et al: (89)Zr-nimotuzumab for immunoPET imaging of epidermal growth factor receptor I. Oncotarget 2018, 9(24):17117-17132.
52. Lindmo T, Bunn P A, Jr.: Determination of the true immunoreactive fraction of monoclonal antibodies after radiolabeling. Methods in enzymology 1986,121:678-691.
53. Fasih A, Fonge H, Cai Z, Leyton J V, Tikhomirov I, Done S J, Reilly R M: (1)(1)(1)In-Bn-DTPA-nimotuzumab with/without modification with nuclear translocation sequence (NLS) peptides: an Auger electron-emitting radioimmunotherapeutic agent for EGFR-positive and trastuzumab (Herceptin)-resistant breast cancer. Breast Cancer Res Treat 2012, 135(1):189-200.

The invention claimed is:

1. A package or composition comprising a cytotoxic agent comprising a first antibody that specifically binds a target disease cell surface receptor, a cytotoxin, and a radiolabel,
wherein the cytotoxin is linked directly to the antibody, and
wherein the radiolabel comprises a radionuclide and optionally a scaffold, wherein the scaffold is directly coupled to the antibody,
and a second cytotoxic agent,
the second cytotoxic agent comprising a second antibody that specifically binds the target disease cell surface receptor,
wherein the second cytotoxic agent comprises a second cytotoxin, wherein the second cytotoxin is linked directly to the second antibody and a second radiolabel, wherein the second radiolabel comprises a second radionuclide and a second scaffold, wherein the second scaffold is directly coupled to the second antibody,
wherein the first antibody is trastuzumab and the second antibody is pertuzumab.

2. A composition comprising:
(a) a first cytotoxic agent comprising a first antibody thereof that specifically binds a first epitope of a target disease cell surface receptor, and
(b) a second cytotoxic agent comprising a second antibody that specifically binds a second epitope of the target disease cell surface receptor,
wherein at least one of the first and second cytotoxic agent comprises a cytotoxin, wherein the cytotoxin is linked directly to the antibody,
wherein at least one of the first and second cytotoxic agent comprises a radiolabel, wherein the radiolabel comprises a radionuclide and optionally a scaffold, wherein the scaffold is directly coupled to the antibody,
wherein the first antibody is trastuzumab and the second antibody is pertuzumab.

3. The composition of claim 2, wherein the radionuclide is $^{225}$Ac and/or the cytotoxin is N(2')-deacetyl-N(2')-(3-mercapto-1-oxopropyl)-maytansine (DM1).

4. A method of treating a disease comprising administering an effective amount of the composition of claim 2, wherein the disease is a cancer that overexpresses the cell surface receptor.

* * * * *

SEQUENCE LISTING

```
<160> NUMBER OF SEQ ID NOS: 8

<210> SEQ ID NO 1
<211> LENGTH: 6
<212> TYPE: PRT
<213> ORGANISM: Artificial Sequence
<220> FEATURE:
<223> OTHER INFORMATION: Synthetic construct

<400> SEQUENCE: 1

Gln Ser Val Ser Ser Ala
1               5

<210> SEQ ID NO 2
<211> LENGTH: 3
<212> TYPE: PRT
<213> ORGANISM: Artificial Sequence
<220> FEATURE:
<223> OTHER INFORMATION: Synthetic construct

<400> SEQUENCE: 2

Ser Ala Ser
1

<210> SEQ ID NO 3
<211> LENGTH: 8
<212> TYPE: PRT
<213> ORGANISM: Artificial Sequence
<220> FEATURE:
```

```
<223> OTHER INFORMATION: Synthetic construct

<400> SEQUENCE: 3

Gln Gln Ser Tyr Trp Leu Ile Thr
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic construct

<400> SEQUENCE: 4

Gly Phe Asn Leu Tyr Ser Ser Ser
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic construct

<400> SEQUENCE: 5

Ile Tyr Pro Tyr Ser Gly Tyr Thr Tyr
1               5

<210> SEQ ID NO 6
<211> LENGTH: 15
<212> TYPE: PRT
<213> ORGANISM: Artificial Sequence
<220> FEATURE:
<223> OTHER INFORMATION: Synthetic construct

<400> SEQUENCE: 6

Ala Arg Tyr Pro Phe Gly Val Ser Ala Tyr Tyr Ala Met Asp Tyr
1               5                   10                  15

<210> SEQ ID NO 7
<211> LENGTH: 230
<212> TYPE: PRT
<213> ORGANISM: Artificial Sequence
<220> FEATURE:
<223> OTHER INFORMATION: Synthetic construct

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Ser Ser
            20                  25                  30

Ser Met His Trp Val Arg Gln Ala Pro Gly Lys Gly Leu Glu Trp Val
        35                  40                  45

Ala Ser Ile Tyr Pro Tyr Ser Gly Tyr Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Pro Phe Gly Val Ser Ala Tyr Tyr Ala Met Asp Tyr Trp
            100                 105                 110

Gly Gln Gly Thr Leu Val Thr Val Ser Ser Ala Ser Thr Lys Gly Pro
        115                 120                 125
```

```
Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr
225             230

<210> SEQ ID NO 8
<211> LENGTH: 224
<212> TYPE: PRT
<213> ORGANISM: Artificial Sequence
<220> FEATURE:
<223> OTHER INFORMATION: Synthetic construct

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Trp Leu Ile Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Ser Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Gly Ser Asp Tyr Lys Asp Asp Asp Lys
    210                 215                 220
```